US011365420B2

(12) United States Patent
Trafford et al.

(10) Patent No.: US 11,365,420 B2
(45) Date of Patent: Jun. 21, 2022

(54) PLANT GENE FOR GRANULE DEVELOPMENT, MODIFIED CEREAL PLANTS AND GRAIN

(71) Applicant: NIAB, Cambridge (GB)

(72) Inventors: Kay Trafford, Cambridge (GB); Cristobal Uauy, Norwich (GB)

(73) Assignee: NIAB, Cambridge (GB)

( * ) Notice: Subject to any disclaimer, the term of this patent is extended or adjusted under 35 U.S.C. 154(b) by 36 days.

(21) Appl. No.: 16/058,683

(22) Filed: Aug. 8, 2018

(65) Prior Publication Data

US 2019/0233838 A1 Aug. 1, 2019

Related U.S. Application Data

(63) Continuation-in-part of application No. PCT/IB2017/050690, filed on Feb. 8, 2017.

(30) Foreign Application Priority Data

Feb. 8, 2016 (GB) ..................................... 1602262

(51) Int. Cl.

*A01H 5/10* (2018.01)
*A01H 1/00* (2006.01)
*C12N 15/82* (2006.01)
*A01H 6/46* (2018.01)

(52) U.S. Cl.

CPC ........... *C12N 15/8261* (2013.01); *A01H 5/10* (2013.01); *A01H 6/46* (2018.05); *A01H 6/4678* (2018.05)

(58) Field of Classification Search

None

See application file for complete search history.

(56) References Cited

FOREIGN PATENT DOCUMENTS

| | | | |
|---|---|---|---|
| CN | 103554238 | A | 2/2014 |
| WO | 03/035874 | A1 | 5/2003 |
| WO | 2004/112468 | A1 | 12/2004 |
| WO | 2014/066497 | A2 | 5/2014 |
| WO | 2017137907 | A | 8/2017 |

OTHER PUBLICATIONS

Konik-Rose et al., Euphytica, May 2009, vol. 167, No. 2, pp. 203-216.*

Suh et al., "Characterization of Nubet and Franubet Barley Starches," Carbohydrate Polymers 56:85-93 (2004).

Wei et al., "Physicochemical Properties and Development of Wheat Large and Small Starch Granules During Endosperm Development," Acta. Physiol. Plant 32:905-16 (2010).

Bathgate et al., "The Significance of Small Starch Granules," European Brewing Convention, The Proceedings of the 14th Congress, Salzburg, Elsevier Scientific Publishing, pp. 183-196 (1974).

Chiotelli et al., "Effect of Small and Large Wheat Starch Granules on Thermomechanical Behavior of Starch," Cereal Chem. 79(2):286-93 (2002).

Evers et al., "Studies on the Biosynthesis of Starch Granules. Part 8. A Comparison of the Properties of the Small and the Large Granules in Mature Cereal Starches," Starch 26(2):42-6 (1974).

Fulton et al., "Microprep Protocol for Extraction of DNA from Tomato and other Herbaceous Plants," Plant Mol. Biol. Reporter 13(3):207-9 (1995).

Takeda et al., "Structures of Large, Medium and Small Starch Granules of Barley Grain," Carbohydrate Polymers 38:109-14 (1999).

Chia et al., Transfer of a starch phenotype from wild wheat to bread wheat by deletion of a locus controlling B-type starch granule content, Journal of Experimental Botany (2017), 1-13.

Howard et al., Identification of a major QTL controlling the content of B-type starch granules in Aegilops, Journal of Experimental Botany (2011), 62(6):2217-2228.

Igrejas et al., Genetic Analysis of the Size of Endosperm Starch Granules in a Mapped Segregating Wheat Population, Journal of Cereal Science (2002), 35:103-107.

International Search Report and Written Opinion of the International Searching Authority dated Aug. 17, 2017.

Al-Kaff et al. "Detailed Dissection of the Chromosomal Region Containing the Ph1 Locus in Wheat Triticum aestivm With Deletion Mutants and Expression Profiling" Annals of Botany 101(6):863-872 (2008).

Myllarinen et al. "Heat Induced Structural Changes of Small and Large Barley Starch Granules" J. Institute of Brewing 104:343-349 (1998).

Park et al. "Starch Granule Size Distribution of Hard Red Winder and Hard Red Spring Wheat: Its Effects on Mixing and Bread Making Quality" J. Cereal Science 49(1):98-105 (2009).

Peng et al. "Floury ENDOSPERM6 Encodes a CBM48 Domain-containing Protein Involved in Compound Granual Formation and Starch Synthesis in Rice Endosperm" Plant J. 77(6):917-930 (2014).

Peng et al. "Separation and Characterization of A- and B-Type Starch Granules in Wheat Endosperm" Cereal Chemistry 76(3):375-379 (1999).

(Continued)

*Primary Examiner* — Phuong T Bui

(74) *Attorney, Agent, or Firm* — Troutman Pepper Hamilton Sanders LLP (Rochester)

(57) ABSTRACT

There is provided a plant of domesticated Triticeae species able to produce a grain with a modified (i.e. decreased or increased) level of B-type granules within the endosperm relative to the unmodified form of the grain. The level of B-type granules can be assessed by number or content by weight or volume. Whilst the level of B-type granule within the grain can be increased or decreased, optionally the grain contains substantially no B-type granules. The plant can contain a wheat Flo6 gene which is genetically modified. The plant of domesticated Triticeae species can be common wheat, barley, rye, durum wheat, spelt wheat, triticale, einkorn wheat or oat. Grain produced the plants, and flour and compositions of matter formed from the grain are also provided.

12 Claims, 13 Drawing Sheets

Specification includes a Sequence Listing.

(56) References Cited

OTHER PUBLICATIONS

Saccomanno et al. "Starch Granule Morphology in Oat Endosperm" J. Cereal Science 73(A1-A2):46-54 (2017).
Soh et al. "Effect of Starch Granule Size Distribution and Elevated Amylose Content on Durum Dough Rheology and Spaghetti Cooking Quality" Cereal Chemistry 83(5):513-519 (2006).
Stoddard et al. "Characterization of Starch in Aegilops Species" Cereal Chemistry 77(4):445-447 (2000).

* cited by examiner

```
                              1            10           20           30           40           50           60
                              |            |            |            |            |            |            |
SEQ ID NO:54  Wheat 4A    ------------------------------------------------------------
SEQ ID NO:56  Wheat 4B    -----------------------------------------------------MPPPRQP
SEQ ID NO:59 Barley FLO6  ------MPPFLLPSLLLPALTLPLPHAPARRRHRVFAAPPAAHSCGRRVCAAHRPPPRQP
SEQ ID NO:60   Rice FLO6  ---------MLPLLLPLPVTPPPPLPSPTLTLAPASAPRRRLVLLAAAAPHHHHHHRRRR
SEQ ID NO:61   At1g27070  MVSINSGPISSFVSRYSMIDSDTLLHLSSFGSTFNPNYKAKACIRFARKVCGSTVLGFLE

                Wheat 4A  -----------------------------------------MRRSDKPGAFPTRAELLAA
                Wheat 4B  Y-RRPAPAPAPAPRPSNAPAPAPPQRGPRDQEELEAAIYDFMRRSDKPGAFPTRAELLAA
             Barley FLO6  YRRRPAPAQVPRSSQSNAPPPPPQQGGPRGQEELEAAIYDFMRRSDKPGAFPTRAELLA-
               Rice FLO6  VYRRQRAAPTQTRAPRRTLSASN---AARGEEDLEEAIYEFMRRSDKPGAFPTRAELVAA
               At1g27070  VKPRKKSCCSRCNGVSRMCNKRNLGWDSEGSKDLETEILEFMKNSEKPGMFPSKKDLIRS

                Wheat 4A  GRADLAAAVESSGGWLSLGWSWSS-DD-DARRPAAST-AGPGVHPEYPPEAGP---SGRP
                Wheat 4B  GRADLAAAVESSGGWLSLGWSWSS-DD-DARRPAAST-AGPGVHPDYPPEAGA---SGRA
             Barley FLO6  GRNDLAAAVESSGGWLSLGWSWSSSDDGDARRPAASS-AGPGAHPDYPPEAGP---SGRA
               Rice FLO6  GRADLAAAVDACGGWLSLGWS----SGGAEAGRASSS---VGVHPDYPPEAGAAAAAGGA
               At1g27070  GRFDLVERIVNQGGWLSMGWDLDEQEE-KVRVNENV--TPQDLHIEKQLP------NCNS

                Wheat 4A  PNSAADSV---REQQEPAPSGRQPETEETE-EAGSGAGLEGMLARLRRERERARPP-PRS
                Wheat 4B  PNATADSV---REQQEPTPSGRQPETEETQ-EAGSGAGLEGMLTRLRRERERARPP-PRS
             Barley FLO6  PNASADSV---REQQEPTPSGRQPVTEETA-EAGSGAGLEGMLTRLRRERERARPP-PHS
               Rice FLO6  SDLAQGAVWASSREAEASPSGRQPETEEEETETKFGTGLDGMLTRLQRERERVRPPLPRS
               At1g27070  PEMDKTL-----NHGDLDLSSNLSSSTEQV--ESRNDSGIEGILTRLEKERNLSLGISVRE

                Wheat 4A  KNQAGG--R--GQNGALMNHNGAPSRSPTNGMYTRRIPVNGNIHRSHSQNGIPEDNKSSS
                Wheat 4B  KNRAGG--Q--GQNGALMNHNGAPSRSPTDGMYTRRIPVNGNIHRSHSQNGIPEDNKSSS
             Barley FLO6  KNQAGR--Q--GQNGALMNHNGAPGRSPTDGIYTRRVPDNGNIRSSYSQNGILEDNKPST
               Rice FLO6  SDGAGGE----RDNVALMGQSGAPSHSATGGRYTPKVPDNGNIHSYHPQNGALEHNKSSK
               At1g27070  NGKSNGAMHDISPNGSVPWSSRIVTASEIQEVDGSRGSGEYAQSRYQGAKSVSGKPGLSD

                                * K2244 W/STOP
                Wheat 4A  S-ANDAWRTWSLDKSRFSD--FEAAEIHPL-SRKPPKHVDLNTVLIEDDVPGPSNGVVIN
                Wheat 4B  S-ANDAWRTWSLDKSRFSD--FEAAEIHPL-SRKPPKRADLDTVLIEDDVPGPSNGVVIN
             Barley FLO6  S-AKDAWRTWSLDNSRFSD--FQAAEIDPW-SRELPKRVDLDTVLMQDDVPGPSNGVAIN
               Rice FLO6  SLTNDAWRTWSLDKGGFSD--FQAAEIHSTNSRKSFRHDGLDI-LAQDDVHGPSNGVAVH
               At1g27070  SPTSETWRTWSMRRAGFTDEDFEAAEISSSGLTGVKKDD------TKKDSGDSMNGK--D

                                                                     K3145/HvFlo6 W/STOP *
                Wheat 4A  DYPSDHVDSERDEIHARFQNLEFDLADSLKTLRSRFDGVSSYMSNGEEADVVNGFSDDWE
                Wheat 4B  DYPSDHVDSERDEIHARFQNLEFDLADSLKTLRSRFDGVSSYMSNGEEADVVNGFSDDWE
             Barley FLO6  GYSSDHVDSGRDEIHARLQNLELDLTDALKTLKSRFDGVSLDMSNGETADVVNGLSDDWE
               Rice FLO6  DYDINDVDSERDDIHARLQNLELDLTAALHTLRSRFDKVISDMSEGDGAKAPNGLSDDWE
               At1g27070  RIASSSEDVNKTHIKHRLQQLQSELSSVLHSLRSPPDKVVTSKDSETTAGNLENLSDDWE

                Wheat 4A  FEETKVMHAQEELRTIRAKIAVLEGKVALEIIEKNKIIEEKQTRLDEVEKALSELRTVSV
                Wheat 4B  FEETKVMHAQEELRTIRAKIAVLEGKVALEIIDKNKIIEEKQTRLDEVEKALSELRTVSV
             Barley FLO6  FEETKVMHAQEELRSIRAKIAVLEGKMALEIIEKNRVIEEKQTRLDEVEKALSELRTVYI
               Rice FLO6  FEETKVMQAQEELRSIRAKIAVLEGKMALEIIEKNKIIEEKQRRLDEAEKALSELRTVYI
               At1g27070  YKENEIIHAQNKLRSTRAKLAVLEGKMAMAIIDAQRIVREKQRRIDHASRALRLLRTASI

                       K0456 E/K  KI  K3239 V/I
                Wheat 4A  VWPNPASEVLLTGSFDGWTSQRRMEQSESGIFSYNLRLYPGRYEVMACYSAFIVTAFSSS
                Wheat 4B  VWPNPASEVLLTGSFDGWTSQRRMEQSEGGIFSYNLRLYPGRYE----------------
             Barley FLO6  VWSNPASEVLLTGSFDGWTSQRRMEKSERGIFSLNLRLYPGRYE----------------
               Rice FLO6  VWSNPASEVLLTGSFDGWTSQRRMERSERGTFSLNLRLYPGRYE----------------
               At1g27070  VWPNSASEVLLTGSFDGWSTQRKMKKAENGVFSLSLKLYPGKYE----------------

                Wheat 4A  DSGCWFVLQIKFIVDGVWKNDPLRPSVNNHGNENNLMIVT*
                Wheat 4B  ----------IKFIVDGVWKNDPLRPTVNNNGNENNLMIVT*
             Barley FLO6  ----------IKFIVDGVWKNDPLRPTVNNHGNENNLVIVT*
               Rice FLO6  ----------IKFIVDGVWRNDPLRPLVSNNGHENNLLTVT*
               At1g27070  ----------IKFIVDGQWKVDPLRPIVTSGGYENNLLIIS*
```

FIG. 10

SEQUENCE LISTING

<160> NUMBER OF SEQ ID NOS: 117

<210> SEQ ID NO 1
<211> LENGTH: 6319
<212> TYPE: DNA
<213> ORGANISM: Aegilops sp.
<220> FEATURE:
<223> OTHER INFORMATION: KU37

<400> SEQUENCE: 1
caagaccata cgtacacata aataaatcag taaatcataa agaagaagaa gaagaagagc 60
agaggaggag ggtccagaag agtagttggc ggtgggaaga tccagaggct gcgcactgcc 120
tgcccggccg cctccacggc catggccagc agcaggcagg aggggaacct cgacgccgtc 180
ctcaaggagg ccgtcgacct ggtaatcact cagttcatca atcaactccc tgctcttggg 240
gtagtatagt gcttcctctc tggtttttag ttagcgttgc gcttcttggg gaaatcacca 300
tgtggctcgg ccgtcggccg ctggggtttc tttccgcgct tcgggcgtcg cagttgcatt 360
gcagggtggt ggagttggcc tgccagcgcc tcttcttgta ggtcaatttg ggagcgtcga 420
tctccctccc ctgcctagtg taccgcactg ctctaaaatc tcacccccca aatcttacta 480
agcaaaattt cacccaggct acaactttga gctactattt tttcccaggg cttacaaaaa 540
ctgcagttta gttttaaatt ttaaaatctc gcagttttat atatagcttt gatttttctt 600
ttgtctggac agcgtgtgag ggctgcttgt aaatgtattt gctctagctt cggattattt 660
tgatttttct tttgtctgga cagtgtatga gggctgatca caagaagtac atactttttc 720
ctctgtttga ttagaatttt tatgatcctc tgtttgatta attttttttt tttgtctctt 780
ggttctctct tctgggttcc ttagagtagc aggctgcagc tagcatactt gctcgttcag 840
attttgctca tgctaatggt acttgtttgg ttttgttaaa agagattgcc gtaacaaaat 900
ttcaggagca catcccaatt gatgaagtgt ttgagaacct tcggtgcagc cacgaggggc 960
tcgcttccga gcaggcgcag cagcggctac agatctttgg cccgaacaag ctcgaggaga 1020
aggaggtcag gttctttcag cccatttgat tatggggaag attttgtcct tgctcttctt 1080

-continued

```
gagagcagta atgttcttct cattgatgtt atgcacttga gtaagttgga gtgtttgatg   1140
gctgcaggag agcaagttcc tcaagtttct ggggttcatg tggaatccac tgtcatgggt   1200
catggaggct gcggcgatca tggccatcgc gctggcgaac ggaggggtaa gacccagcac   1260
atagtattgc agaatttgtg gtgatgagtg atgttgtatg tcctgctctg ttctcaatat   1320
atatgtggga tgtgttctgt caccaccagg ggaagccacc agattggcaa gactttgtcg   1380
gtatcatcac gctgctactt ataaactcca ccatcagttt catcgaggaa aacaatgccg   1440
gaaatgctgc cgccgcgctt atggcacgtc ttgcgccaaa agccaaggtc catatattca   1500
cttaatttgt ggcatttccc ctgtttctgc acgtatcacc ttgttggagt ccattttaat   1560
ttgtgaaact cattattata ttgctaagta ggttctccgt gacggtcgtt ggaccgagga   1620
ggaggcagcc gtccttgtgc ctggggacat catcagcatc aaacttggag atatcattcc   1680
tgccgacgcc cgcctcctag acggcgatcc tttgaagatt gatcaggttt tttctgtcct   1740
tcacatccga gtcaccttca gctttgcttt tacttattta gatttcctat ttcctcatct   1800
cactacttgg tctcttattt atagtctgcc ctgactggag aatcgctgcc agccaccaaa   1860
ggtcctggtg acggcgtcta ctctggttcg acggtcaagc agggcgagat cgaggctgtt   1920
gtcatagcaa ctggtgtgca cactttcttt gggaaggccg cacatctcgt cgactccacc   1980
aaccaagttg gccatttcca acaggcaagc ttgacaagcc tcggatactt ttatcgaatt   2040
gtatcatcgc tacattgatg ttttcattat catgcgattg acgcaggtgt tgacagccat   2100
cgggaacttt tgcatttgct cgattggtgt ggggatgttc atagagatca ttgtcatgta   2160
tcctatccag cacagggcgt accgccctgg gatcgacaac cttttggtgc ttctcattgg   2220
aggcattccc atagcgatgc ccacagtctt gtcggtcacc atggcgattg ggtctcatcg   2280
cttgtctcaa caggtatgca tcattccagg gacagtgtct cttaaccata ttgtgaccag   2340
acctgaactt ctgcactatg caatcaattc ctgagttttc ttcctgcagg gagctataac   2400
aaagagaatg actgcaatcg aagagatggc cggcatggat gttctttgca gtgataagac   2460
tggaaccctg actctaaata agctcagcgt ggacaagaac ctaatcgagg taaggttcac   2520
ttgaacactc actttttgtt atctcatatg taacctcaga gcacttacat acttttttttg   2580
gtgcaggttt ttgaaaaagg agtgactcag gaccaggtga ttctgatggc tgctagagca   2640
tcccggatag aaaatcaaga tgccattgat acggcgattg ttgggatgct aggcgatcca   2700
aaagaggtac attgatttgt cgaataatga gacgtacagc tatcacgttt atttgctaaa   2760
atggatacct gttaactctc cccgtaggcg cgtgccggta ttcaagaggt tcactttctg   2820
ccgttcaatc ctaccgacaa aagaaccgcg ttgacataca ttgatggcga tggaaagatg   2880
taccgtgtta gcaaaggtgc accagagcag gtataatctt tttttactgc aaaaagctta   2940
aaaaacattt gcataatgat gtaaattgat ttcacaaatt gacctgcaga ttcttaacct   3000
ggcctacaac aagtcagaga tcgcacaaaa agtccacact gtcatcgaca agttcgcgga   3060
acgtggactt cggtcacttg gtgtagcata tcaggtgaga aaggttctgg gtgtgcccct   3120
tcacagtgca gttgaagctt gcaaggcagg aacttagtgg tggtcattct tttctgcctt   3180
gtaggacgtg ccagatagga ggaaagagag cccgggtagc ccgtggcatt ttgttgctct   3240
cttgccactc tttgatccac cgaggcacga cagcgcagaa acaattcaaa gggcacttaa   3300
ccttggtgtg aatgtgaaga tgatcacagg tacactgcca attgggttgt tactactttt   3360
ttgctctgtt cttaaatatc caattcgatg aagatgatca caagtaaatg cactaccggt   3420
tgaattctat tttgttctct tctctctatt cttaaatctc ccaattttta tgagcaccat   3480
```

gtctttgatg tttactattt tttatttgtg atgtcatgta aggacccctt aaaaagctgt 3540
gccataagta gagttggaac attgaacata tgctgtatct tatcttgttt tattataatt 3600
tcagtttcaa taattttggt aatacatctt attgtgcttt tccccccctaa ggcgaccagc 3660 tagcgattgg gaaggaaaca gggcgtcgtc taggaatggg tacaaacatg tacccatcat 3720
ctgctttgct ggggcagaac aaggatgagt ctattgctga tttaccagtc gatgatctaa 3780
ttgagaaagc cgatggtttt gctggcgtat tcccaggtat gtgctgtaat cagttagaag 3840
aaaataaaat caaagaaatg aaaaaggaac ataacaataa taatataatg gtaacatttg 3900
ttctttgctc agaacacaaa tatgagattg tgaaacgcct acaagcacgg aagcacattt 3960
gtggaatgac tggtgatggc gtaaatgatg caccagccct aaagaaagct gatattggta 4020
tagcggttgc cgatgcgaca gatgcagcga ggagtgcttc tgatatcgta ctaaccgaac 4080
ctggtctaag tgtgatcatt agtgccgtcc ttaccagtcg agccattttc cagcggatga 4140
agaactacac tgtatgtcag attgacccca gtggatgaga attttctttg cccccattta 4200
tttgaagagt tattcctaca tttatgcttg tgtcatttag cccatatgct aatccaattt 4260
catgcttgca gatctatgcg gtttcaatta cgatacgtat tgtggtatgt ttgattgaca 4320
ctataaaagt ttgccaaagt gcattggctc atgctctgtt ttacatagtt gatgattctc 4380
ttacgtgtca attataacta ttcgtttaat gaatttttc ttttaacatt gatgttccag 4440
tatatgatgt tttcatcttg atctgtgaaa ttatgtccat gaagctaaca tttttttatt 4500
ttgtgattat gcatctgatt cctctttacc ccctaacagc ttggatttat gctacttgcc 4560
ctcatatggg agtttgattt cccgccattt atggtcctga tcatagcaat tttgaatgat 4620
ggtacaattc tttcttttcc ttccattctc cccgcgcttc ccgtgcctac aatatcaccg 4680
tattaagtag aaaattatat tatagtgctc accctgaagg cctgaaccat tttgtggcat 4740
gaacaggtac cataatgaca atatcgaagg atcgagtaaa gccttcccca ctacctgaca 4800
gctggaagtt ggctgaaatt ttcacaactg gggtggttct tggcggatac ttggcaatga 4860
tgactgtcat tttcttctgg gctgcataca agactaactt tttccctgta aggagtacct 4920
aagtgaaatt aaattctgtt tttttttcta aaacattgat tgcagataat gaagtaacct 4980
cttgatatgt ggcccacgaa gctaccaact attaggacca atatgctagt ttgtgatctg 5040
atcctcagac atgcattgac acttgttgtt caataaattt tcagagggtc tttcatgtga 5100
aaagccttga gaagacagct caagatgact tcaaaatgct tgcctctgct gtataccttc 5160
aagtcagcac catcagccaa gctctcatct tcgttacaag gtctcgaagt tggtcgttcg 5220
tcgagcgccc tggctttctc ctggtcttcg ctttctttgt cgcgcagctg gtattttttc 5280
tcacggtctc acccactgtt tgctttacat gtaagtacac aagtcaagtt ccagtgagca 5340
agtttcaagt ttcaccaccc ccttcaaaaa atgcagatag ctacactgat cgctgtatac 5400
gccgactggg gattcacttc gatcaaaggc atcggatggg gctgggctgg catcgtgtgg 5460
ctctacaaca tcgtcttcta cttcccgctt gacatcatca agttcttcat ccgatacgct 5520
ctgagcggca aagcatggga tcttgtcatt gaccaaagag tagttcaaaa tttcaaattg 5580
caccaccata tttttccttg tctttttag ctattgagaa cccaatacat tctatgcatc 5640
ttgtaaatga tggttcattt ctccttttc tttatagatc gcatttacaa ggaagaagca 5700
ctttggtaag gaagagaggg agctcaagtg ggcccatgca cagaggacac tccatgggct 5760
gcagccgccg gatgccaagc tgtttcctga gaaggcaggc tacaacgagc tgaatcaaat 5820

-continued ggccgaggag gcgaagcgga gggctgagat tgcaaggtat gtaggacctg attcccagca 5880
ggcacttgca tgaaattcca cgtatgggat gcattccaag atcaccctat ttcttgacaa 5940
ttatgaatcc aacttatgtg cttattaatg acggtacatg gcatgcaggc tcagggagct 6000
ccacactctc aaggggcatg tggagtcagt tgtgaagctg aagggcctcg acatcgacac 6060
cattcagcaa tcttacaccg tgtgatagat tcaagtatcc ttaaaagtta ctgtagaaga 6120
gagagtatat ccttgctgcc taggaataac agacttttga taggttgctt ttgccccctc 6180
ttatatagtt gactgctgat acgtcgtggg aataaaacgg ttactacaca tctcagctgc 6240
tctccagtcg ctggttcgtt gtgcttcatg taaaggaata cagttatcct gtctcttgct 6300
tctgcaactg ggggtttta 6319

<210> SEQ ID NO 2
<211> LENGTH: 6297
<212> TYPE: DNA
<213> ORGANISM: Aegilops peregrina
<220> FEATURE:
<221> NAME/KEY: misc_feature
<222> LOCATION: (5380)..(5380)
<223> OTHER INFORMATION: Single nucleotide mutation creating amino acid change and non-functional protein

<400> SEQUENCE: 2
caagaccata cgtacacata aataaatcat tgaatcccaa agaagaagaa gaagaagagc 60
agaggaggag ggtccagaag agtagttggc ggtgggaaga tccagaggct gcgcactgcc 120
tgcccggccg cccccgtcgc catggccagc agcaggcagg aggggaacct cgacgccgtc 180
ctcaaggagg ccgtcgacct ggtaatcact cagttcatca atcaactccc tgctcttggg 240
gtagtatagt gcttcctctc tggtttttag ttagcgttgc gcttcttggg gaaatcacca 300
tgtggctcgg ccgtcggccg ctggggtttc tttccgcgct tcgggcgtcg cagttgcatt 360
gcagggtggt ggagttggcc tgccagcgcc tcttcttgta ggtcaatttg ggagcgtcga 420
tctccctccc ctgcctagtg taccgcactg ctctaaaatc tcacccccca aatcttacta 480
agcaaaattt cacccaggct acaactttga gctactattt tttcccaggg cttacaaaaa 540
ctgcagttta gttttaaatt ttaaaatctc gcagttttat atatagcttt gatttttatt 600
ttgtctggac agcgtatgag ggctgcttgt aaatgtattt gctctagctt cggattattt 660
tgatttttct tttgtctgga cagtgtatga cggctgatca caagaagtac atactttttc 720
ctctgtttga ttagaatttt tatgatcctc tgtttgatta gaattttttt tttgtctctt 780
ggttctctct tctgggttcc ttagagtagc aggctgcagc tagcatactt gcacgttcag 840
attttgctca tgctaatggt acttgtttgg ttttgataaa agagattgcc gtaacaaaat 900
ttcaggagca catcccaatt gatgaagtgt ttgagaacct tcggtgcagc cacgaggggc 960
tcgcttccga gcaggcgcag cagcggctgc agatctttgg cccgaacaag ctcgaggaga 1020
aggaggtcag gttctttcag cccatttgat tatggggaag attttgtcct tgctcttctt 1080
gagagcagta atgttcttct cattgatgtt atgcacttga gtaagttgga gtgtttgatg 1140
gctgcaggag agcaagttcc tcaagtttct ggggttcatg tggaatccac tgtcatgggt 1200
catggaggct gcggcgatca tggccatcgc gctggcgaac ggaggggtaa gacccagcac 1260
atagtattgc agaatttgtg gtgatgagtg atgttgtatg tcctgctctg ttctcaatat 1320
atatgtggga tgtgttctgt caccaccagg ggaagccacc agattggcaa gactttgtcg 1380
gtatcatcac gctgctactt ataaactcca ccatcagttt catcgaggaa aacaatgccg 1440

-continued

```
gaaatgctgc cgccgcgctt atggcacgtc ttgcaccaaa agccaaggtc catatattca   1500
cttaatttgt ggcatttccc ctgtttctgc acgtatcacc ttgttggagt ccattttaac   1560
ttgtgaaact cattattata ttgctaagta ggttctccgt gacggtcgtt ggaccgagga   1620
ggaggcagcc gtccttgtgc ctggggacat catcagcatc aaacttggag atatcattcc   1680
tgccgacgcc cgcctcctag acggcgatcc tttgaagatt gatcaggttt tttctgtcct   1740
tcacatccga gtcaccttca gctttgcttt tacttattta gatttcctat ttcctcatct   1800
cactacttgg tcttttattt atagtctgcc ctgactggag aatcgctgcc agccaccaaa   1860
ggtcctggtg acggcgtcta ctctggttcg acggtcaagc agggcgagat cgaggctgtt   1920
gtcatagcaa ctggtgtgca cactttcttt gggaaggccg cacatctcgt cgactccacc   1980
aaccaagttg gccatttcca acaggcaagc ttgacaagcc tcggatactt ttatcgaatt   2040
gtatcatcgc tacattgatg ttttcattat catgcgattg acgcaggtgt tgacagccat   2100
cgggaacttt tgcatttgct cgattggtgt ggggatgttc atagagatca ttgtcatgta   2160
tcctatccag cacagggcgt accgccctgg gatcgacaac cttttggtgc ttctcattgg   2220
aggcattccc atagcgatgc ccacagtctt gtcggtcacc atggcgattg ggtctcatcg   2280
cttgtctcaa caggtatgca tcattccagg gacagtgtct cttaaccata ttgtgaccag   2340
acctgaactt ctgcaccatg caatcaattc ctgagttttc ttcctgcagg gagctataac   2400
aaagagaatg actgcaatcg aagagatggc cggcatggat gttctttgca gtgataagac   2460
tggaaccctg actctaaata agctcagcgt ggacaagaac ctaatcgagg taaggttcac   2520
ttgaacactc actttttgtt atctcatatg taacaccaaa gcacttgcat actttcttgg   2580
tccaggtttt tgaaaaagga gtgactcagg accaggtgat tctgatggct gctagagcat   2640
cccggataga aaatcaagat gccattgata cggcgattgt tgggatgcta ggcgatccaa   2700
aagaggtaca ttgattcgtc gaataatgag acgtacagct atcacgttta tttgctaaaa   2760
tggatacctg ttaactctcc ccgtaggcgc gtgccggtat tcaagaggtt cattttctgc   2820
cgtttaatcc taccgacaaa agaactgcgt tgacatacat tgatggcgat ggaaagatgt   2880
accgtgttag caaaggtgca ccagagcagg tataatcttt tcttactgca aaaagcttaa   2940
aaaacatttg cataatgatg taaattgatt tcacaaattg acctgcagat tcttaacctg   3000
gcctacaaca agtcagagat cgcacaaaaa gtccacactg tcatcgacaa gttcgcggaa   3060
cgtggacttc ggtcacttgg tgtagcatat caggtgagaa aggttctggg tgtgcccctt   3120
cacagtgcag ttgaagtttg caaggcagga acttagtggt ggtcattctt ttctgccttg   3180
taggacgtgc cagataggag gaaagagagc ccgggtagcc cgtggcattt tgttgctctc   3240
ttgccactct ttgatccacc gaggcacgac agcgcagaaa caattcaaag ggcacttaac   3300
cttggtgtga atgtgaagat gatcacaggt acactgccaa ttgggttgtt actacttttt   3360
tgctctgttc ttaaatatcc aattcgatga agatgatcac aagtaaatgc actaccggtt   3420
gaattctatt ttgttctctt ctctctattc ttaaatctcc caatttttat gagcaccatg   3480
tctttgatgt ttactatttt ttatttgtga tgtcatgtaa gtacccctta aaaagctgtg   3540
ccataagtaa ttgaacatat gctgtatctt atcttgtttt attataattt cagtttcagt   3600
aattttggta atacatctta ttgtgctttt cccccctaag gcgaccagct agcgattggg   3660
aaggaaacag ggcgtcgtct aggaatgggt acaaacatgt acccatcatc tgctttgctg   3720
gggcagaaca aggatgagtc tattgctgat ttaccagtcg atgatctaat tgagaaagcc   3780
gatggttttg ctggcgtatt cccaggtatg tgttgtaatc agttagaaga aaataaaatc   3840
```

-continued

```
aaagaaatga aaaaggaaca taacaataat aatataatgg taacatttgt tctttgctca   3900
gaacacaaat atgagattgt gaaacgccta caagcacgga agcacatttg tggaatgact   3960
ggtgatggcg taaatgatgc accagcccta aagaaagctg atattggtat agcggttgcc   4020
gatgcgacag atgcagcgag gagtgcttct gatatcgtac taaccgaacc tggtctaagt   4080
gtgatcatta gtgccgtcct taccagtcga gccattttcc agcggatgaa gaactacact   4140
gtatgtcaga ttgaacccag tggatgagaa ttttctgtgc cccatttat ttgaagagtt   4200
attcctacat ttatgcttgt gtcatttagc ccatatgcta atccaatttc atgcttgcag   4260
atctatgcgg tttcaattac gatacgtatt gtggtatgtt tgattgacac tataaaagtt   4320
tgccaaagtg cattggctca tgctctgttt tacatagttg atgattctct taggtgtcaa   4380
ttataactat tcgtttaatg aatttttct tttaacactg atgttccagt atatgatgtt   4440
ttcatcttga tctgtgaaat tatgtccatg aagctaacat ttttttattt tgtgattatg   4500
catctgattc ctctttaccc cctaacagct tggatttatg ctacttgccc tcatatggga   4560
gtttgatttc ccgccattta tggtcctgat catagcaatt ttgaatgatg gtacaattct   4620
ttcttttcct tccattctcc ccgcgcttcc cgtgcctaca atatcaccgt attaagtaga   4680
aaattatatt atagtgctca ccctgaaggc ctgaaccatt ttgtggcatg aacaggtacc   4740
ataatgacaa tatcgaagga tcgagtaaag ccttccccac tacctgacag ctggaagttg   4800
gctgaaattt tcacaactgg ggtggttctt ggcggatact tggcaatgat gactgtcatt   4860
ttcttctggg ctgcatacaa gactaacttt ttccctgtaa ggagtaccta agtgaaatta   4920
aattctgttt tttttctaaa acattgattg cagataatga agtaacctct tgatatctgg   4980
cccacgaagc taccaactat taggaccaat atgctagttt gtgatctgat cctcagacat   5040
gcattgacac ttgttgttca ataaattttc agagggtctt tcatgtgaaa agccttgaga   5100
agacagctca agatgacttc aaaatgcttg cctctgctgt ataccttcaa gtcagcacca   5160
tcagccaagc tctcatcttc gttacaaggt ctcgaagctg gtcgttcgtc gagcgccctg   5220
gctttctcct ggtcttcgct ttctttgtcg cgcagctggt attttttctc acggtctcac   5280
ccactgtttg ctttacatgt aagtacacaa gtcaagttcc agtgagcaag tttcaagttt   5340
caccaccccc ttcaaaaaat gcagatagct acactgatcc ctgtatacgc cgactgggga   5400
ttcacttcga ttaaaggcat cggatggggc tgggctggca tcgtgtggct ctacaacatc   5460
gtcttctact tcccgcttga catcatcaag ttcttcatcc gatacgctct gagcggcaaa   5520
gcatgggatc ttgtcattga ccaaagagta gttcaaaatt tcaaattgca ccaccatatt   5580
tttccttctc ttttttagct attgagaacc caatacattc tatgcatctt gtaaatgatg   5640
gttcatttct cctttttctt tatagatcgc atttacaagg aagaagcact ttggtaagga   5700
agagagggag ctcaagtggg cccatgcaca gaggacactc catgggctgc agccgccgga   5760
tgccaagctg tttcctgaga aggcaggcta caacgagctg aatcaaatgg ccgaggaggc   5820
gaagcggagg gctgagattg caaggtatgt aggacctgat tcccagcagg cacttgcatg   5880
aaattccacg tatgggatgc attccaagac cagcctattt cttgacaatt atgaatccaa   5940
cttatgtgct tattaatgac ggtacatggc aggctcaggg agctccacac tctcaagggg   6000
catgtggagt cagttgtgaa gctgaagggc ctcgacatcg acaccattca gcaatcttac   6060
accgtgtgat agattcaagt atccttaaaa gttactgtag aagagagagt atgtccttgc   6120
tgcctaggaa taacagactt ttgataggtt gcttttgccc cctctttgtt gactgctgat   6180
```

acatcgtggg aataaaacgg ttactacatc tcagttgctc tccaattgct ggttcgttgt 6240
gcttcatgta aaggaataca gttatcctgt ctcttgcctc tgcaactggg ggtttta 6297

<210> SEQ ID NO 3
<211> LENGTH: 5756
<212> TYPE: DNA
<213> ORGANISM: Aegilops crassa
<220> FEATURE:
<221> NAME/KEY: misc_feature
<222> LOCATION: (2933)..(2933)
<223> OTHER INFORMATION: Single nucleotide mutation creating amino acid change and non-functional protein
<220> FEATURE:
<221> NAME/KEY: modified_base
<222> LOCATION: (4344)..(4344)
<223> OTHER INFORMATION: a, c, g, or t

<400> SEQUENCE: 3
ggccgtcgac ctggtaatta accaacgccc tgctcttggg gtggcgcttc ctgtggtttc 60
tagtggccgc ggtgcttgga tgtggatggg ttgccgttgc gcgcagctgg gcttttttac 120
cggggcttag cagtgttctt ctagttctat aggtcaattc ttgttcggca tcgccctttg 180
ttttgttact aattattacg aatcccgcaa ctctagatca ccatcttcta ggcctgctct 240
gttttgttgc caacagagga tcccctgcct cgttggttta ctcacattag ttcctgagaa 300
tctcacacta gaacttctga ttgtttttttg cgtgccgtgt aggagggctg ccctgtcaat 360
gtatttactc tagctttgta gtattatttt gtatcttttt tttgttctaa cttaaggtga 420
ctggaccgtg ggaaaaagtg tgtactcatg atcctctgtt taattggatt tgattttttt 480
tttggcctct tagcttggtt ctctcttctg ggttccttgg agtagtaggc tgcagctagc 540
atgcttgcac gttcagaatt gctcatggta atggtacttg tttggtttgc taaaagcgat 600
cgtcgcaaca aaatttcagg agcacatccc gatcgatgaa gtgttcgaga agcttcggtg 660
cagccaccag gggctcactt ccgagcaggc gcagcagcgg ctgcagatct tcggcccgaa 720
caagctcgag gagaaggagg tcaggttcat tcggcccatt tgattgtggg gaagattttg 780
tctttgctct tcttgagagc agtaatgttc ttctcattga tgttatgcac ttgattaagt 840
tggagcgttt gatggctgca ggagagcaag ttcctcaagt ttctggggtt catgtggaac 900
ccactctcat gggtcatgga ggctgcggcg atcatggcca tcgcgttggc caacggaggg 960
gtaagaccta acacgtatat agcagaattt gtggtgatgt tttagttggg tgctgagtgg 1020
agtgcacgtc ttgctctgtt ctcaacatgt garaagatgt gtgttctgta atcaggggaa 1080
gccaccagat tggcaagact ttgtcggtat catcacgctg ctgcttgtaa actccaccat 1140
cagtttcatc gaggaraaca atgccggaaa tgccgccgcc gcgcttatgg cccgtcttgc 1200
accaaaagcc aaggtctata ttcagtttaa tttgtggggg ttttctgtcc cctgtttctg 1260
gatgtacgtg tcaccttgtc ggagtccatt tgaacagtga aactcaattc ttatgttgct 1320
aagtaggtcc tccgtgatgg tcgttggacc gaggaggagg cagccgtcct tgtgcctggg 1380
gacatcgtca gtatcaaact tggagatatc attcctgccg acgcccgcct cctagacggc 1440
gatcctttga agattgatca ggttctttct gtccttcaca ttcaagtcac cttcagcttt 1500
gcttttactt atgtagattt cctcgtctca ctacttggtc tcttatttat agtctgccct 1560
gaccggagaa tcgctgccag ccaccaaagg tcctggtgac ggcgtctact ctggttcgac 1620
ggtcaagcag ggcgagatcg aggctgttgt catagcaact ggtgtgcaca ctttctttgg 1680
aaaggctgca catctcgtcg actccaccaa ccaagttggc catttccaac aggcaagctt 1740

-continued

```
gacaagcctc ggatactttt atcgaattgt atcatcgcta cattgatgtt ttcattatca   1800
agcgattgat gcaggtgttg acagccatcg ggaacttttg catttgctcg attgctgtgg   1860
ggatgttcat agagatcatt gtcatgtatc ctatccagca cagggcgtac cgccctggga   1920
tcgacaacct tttggtgctt ctcattggag gcattcccat agcgatgccc acagtcttgt   1980
cggtcaccat ggcgattggg tctcatcgct tgtctcaaca ggtatgcatc attccaggga   2040
cagtgtctct taaccatatt gtgactagac ctgaacttct gcactaagca atcaattcct   2100
gagttctctt cctgcaggga gctataacaa agagaatgac tgcaatcgaa gagatggccg   2160
gcatggatgt tctttgcagt gataagactg gaaccctgac tctaaataag ctcagcgtgg   2220
acaagaacat tatcgaggtt cacttgaaca ctagctttgt attatcccac atgttacctc   2280
aaagcaccta catacttttt ttggtccagg tttttgaaaa aggagtgact caggaccagg   2340
tgattctgat ggctgctaga gcatcccgga tagaaaatca agatgccatt gatacggcaa   2400
tagttggcat gctaggtgat ccaaaagagg tacattgatt tgtcgaatag tgagatgtac   2460
acctgtcatg tttatttgct aaatagacat ctatcaacgc ttcccatagg cacgggccgg   2520
tattcaagag atccattttc tgccgttcaa tcctaccgac aaaagaactg cgttgacata   2580
cattgatagc gatggaaaga tgtaccgagt tagcaaaggt gcaccagagc aggtataata   2640
tttttactg caaaaagctt aaaaaacatt tgcataatga gtaaattgat ttcacaaatt   2700
gacctgcaga ttcttaacct ggcctacaac aagtcagaga tcgcacaaaa agtccacact   2760
gtcatcgaca agttcgcgga acgtggactt cggtcacttg gtgtagcata tcaggtgaga   2820
aaggttctgg gggtgcccct tcacaatgca gttgaagctt gcaaggcagg aacttagtgg   2880
tggtcattct tttctgcctt gtaggacgtg ccagacggaa ggaaagagag cctgggtagc   2940
ccgtggcatt ttgttgctct cttgccactc tttgatccac cgaggcacga cagcgcagaa   3000
acaattcaaa gggcacttaa ccttggtgtg aatgtgaaga tgatcacagg tacactgcca   3060
attgggttgt tactaccttt ctgctctgtt cttaaatatt caattcgatg aagatgatca   3120
caagtaaatg cactaccggt tgaattctat attgttctct tctctctatt cttaaatctc   3180
ccaattttta tgagcaccat gtctttgatg tttactattt ttgatttgtg atgtcatgta   3240
agtatccctt aaaaagctgt gccataagta gagttagaac gttgaaccat atgccgtatc   3300
ttatcttgtt ttatttataa tttcagtttc aataattttg gtaatacatc tcattgtgca   3360
ttttttttg tttttcctta ggcgaccagc tagcgattgg gaaggaaaca gggcgtcgtc   3420
taggaatggg tacaaacatg taccctcat ctgctttgct ggggcagaac aaggatgagt   3480
ctattgctga tttaccagtc gatgatctaa ttgagaaagc cgatggtttt gctggcgtat   3540
tcccaggtat gtgttgtaac cagttagaag aaaataaaat caaagaaatg aaaaaggaac   3600
ataacaataa taatataatg gtaacatttt ttctttgctc agaacacaaa tatgagattg   3660
tgaaacgcct acaagcacgg aagcacattt gtggaatgac tggcgatggc gtaaacgatg   3720
caccagccct aaagaaagct gatattggta tagcggttgc cgatgcgaca gatgcagcga   3780
ggagtgcttc tgatatcgta ctcaccgaac ctggtctaag tgtgatcatt agtgccgtcc   3840
ttaccagtcg agcgattttc cagcggatga agaactacac tgtatgtcag attgaaccca   3900
gtggatgaga attttctttg cccccattta tttgaagagt tattcctaca tttatgcttg   3960
tgtcatttag cccatatgct aatccacctt catgcttgca gatctatgcg gtttcaatta   4020
cgatacgtat tgtggtatgt ttgattgaca ctataagttt gccaaagtgc attggctcat   4080
gctctgtttt acatagttga tgattctctt aggtgtcaat tataactatt cgtttaatga   4140
```

-continued

```
atttttttctt ttaacactga tgttccagta tatgatgttt tcatcttgat ctgtgaaatt   4200
atgtccatga agctaacatt tttttatttt tgtgattatg catctgattc ctctttaccc   4260
cccaccagct tggatttatg ctacttgccc tcatatggga gtttgatttc ccgccattta   4320
tggtcctgat catagcaatt ttgnatgatg gtacattact ttcttttcct tccattcctc   4380
cggcgcttcc cgcgcctcac aatatcaccg tattaagtac aaaattatat tgtagtgctc   4440
acccttaacc attttgtggc atgaacaggt accataatga caatatcgaa ggatcgagta   4500
aagccttctc cactacctga cagctggaag ttggctgaaa tttttacaac tggggtggtt   4560
cttggcggat acttggcaat gatgactgtc attttcttct gggctgcata caagactaac   4620
tttttccctg taaggagtac ctaaatgaaa ctaaattctg ttttttcttc tgtaaggagt   4680
acctaaatga aaatcgcttg atatgttgtt caccaagcta ccaactatta ggaccattat   4740
actagtttgt gatctgatcc tcagacatgc attgacactt gttgttcaat aaattttcag   4800
agggtctttc atgtaaaaag ccttgagaag accgctcaag atgacttcaa aatgcttgcc   4860
tctgctgtat accttcaagt cagcaccatc agccaagctc tcatcttcgt tacaaggtct   4920
cgaagctggt cgttcgtcga gcgccccggc tttctcctgg tctttgcttt cttggtcgca   4980
cagctggtat ttttttttct cacggcctcg ccctcctcgc tttgctttac atgtatgtaa   5040
atttacaagt caagttccag tagcaagttt caccacctcc ttcaaaatgc agatagctac   5100
actgatcgct gtatacgccg actggggatt cacttcgatc aaaggcatcg gatggggctg   5160
ggctggcatc gtgtggctct acaacatcgt cttctacttc ccgcttgaca tcatcaagtt   5220
cttcatccga tacgctctga gcggcaaagc atgggatctt gtcattgacc aaagagtaat   5280
tcaaattgca ccaccatatt tttccttctc tttttagcta ttgagaaccc actacattcg   5340
atgcatcttg taaatgacgg ttcatttgtc cattttcttt atagatcgcg tttacaagga   5400
agaagcactt tggtaaggaa gagagggagc tcaagtgggc ccatgcacag aggacgctcc   5460
atgggctgca gccaccgaat gccaagctgt tccctgagaa ggcgggctac aacgagctct   5520
gtcagatggc cgaggaggcg aaacggaggg ccgagattgc aaggtatgta gggctagata   5580
cccagcaggc acttgcaaat tagagaatcc catcttccat atttttttgac aactactccc   5640
tatgttagct taaaaaacgc tcttatatta tggggtggag ggagtatgag tctaactacg   5700
tgcttgttga ttgtgcatgg caggctcagg gagctccaca ctctcaaggg gcatgt       5756
```

<210> SEQ ID NO 4
<211> LENGTH: 970
<212> TYPE: PRT
<213> ORGANISM: Aegilops sp.
<220> FEATURE:
<223> OTHER INFORMATION: KU37

<400> SEQUENCE: 4

```
Met Ala Ser Ser Arg Gln Glu Gly Asn Leu Asp Ala Val Leu Lys Glu
1               5                   10                  15

Ala Val Asp Leu Glu His Ile Pro Ile Asp Glu Val Phe Glu Asn Leu
            20                  25                  30

Arg Cys Ser His Glu Gly Leu Ala Ser Glu Gln Ala Gln Gln Arg Leu
        35                  40                  45

Gln Ile Phe Gly Pro Asn Lys Leu Glu Glu Lys Glu Glu Ser Lys Phe
    50                  55                  60

Leu Lys Phe Leu Gly Phe Met Trp Asn Pro Leu Ser Trp Val Met Glu
65                  70                  75                  80
```

```
Ala Ala Ala Ile Met Ala Ile Ala Leu Ala Asn Gly Gly Gly Lys Pro
                85                  90                  95

Pro Asp Trp Gln Asp Phe Val Gly Ile Ile Thr Leu Leu Leu Ile Asn
            100                 105                 110

Ser Thr Ile Ser Phe Ile Glu Glu Asn Asn Ala Gly Asn Ala Ala Ala
        115                 120                 125

Ala Leu Met Ala Arg Leu Ala Pro Lys Ala Lys Val Leu Arg Asp Gly
    130                 135                 140

Arg Trp Thr Glu Glu Glu Ala Ala Val Leu Val Pro Gly Asp Ile Ile
145                 150                 155                 160

Ser Ile Lys Leu Gly Asp Ile Ile Pro Ala Asp Ala Arg Leu Leu Asp
                165                 170                 175

Gly Asp Pro Leu Lys Ile Asp Gln Ser Ala Leu Thr Gly Glu Ser Leu
            180                 185                 190

Pro Ala Thr Lys Gly Pro Gly Asp Gly Val Tyr Ser Gly Ser Thr Val
        195                 200                 205

Lys Gln Gly Glu Ile Glu Ala Val Val Ile Ala Thr Gly Val His Thr
    210                 215                 220

Phe Phe Gly Lys Ala Ala His Leu Val Asp Ser Thr Asn Gln Val Gly
225                 230                 235                 240

His Phe Gln Gln Ala Ser Leu Thr Ser Leu Gly Tyr Phe Tyr Arg Ile
                245                 250                 255

Val Leu Thr Ala Ile Gly Asn Phe Cys Ile Cys Ser Ile Gly Val Gly
            260                 265                 270

Met Phe Ile Glu Ile Ile Val Met Tyr Pro Ile Gln His Arg Ala Tyr
        275                 280                 285

Arg Pro Gly Ile Asp Asn Leu Leu Val Leu Leu Ile Gly Gly Ile Pro
    290                 295                 300

Ile Ala Met Pro Thr Val Leu Ser Val Thr Met Ala Ile Gly Ser His
305                 310                 315                 320

Arg Leu Ser Gln Gln Gly Ala Ile Thr Lys Arg Met Thr Ala Ile Glu
                325                 330                 335

Glu Met Ala Gly Met Asp Val Leu Cys Ser Asp Lys Thr Gly Thr Leu
            340                 345                 350

Thr Leu Asn Lys Leu Ser Val Asp Lys Asn Leu Ile Glu Val Phe Glu
        355                 360                 365

Lys Gly Val Thr Gln Asp Gln Val Ile Leu Met Ala Ala Arg Ala Ser
    370                 375                 380

Arg Ile Glu Asn Gln Asp Ala Ile Asp Thr Ala Ile Val Gly Met Leu
385                 390                 395                 400

Gly Asp Pro Lys Glu Ala Arg Ala Gly Ile Gln Glu Val His Phe Leu
                405                 410                 415

Pro Phe Asn Pro Thr Asp Lys Arg Thr Ala Leu Thr Tyr Ile Asp Gly
            420                 425                 430

Asp Gly Lys Met Tyr Arg Val Ser Lys Gly Ala Pro Glu Gln Ile Leu
        435                 440                 445

Asn Leu Ala Tyr Asn Lys Ser Glu Ile Ala Gln Lys Val His Thr Val
    450                 455                 460

Ile Asp Lys Phe Ala Glu Arg Gly Leu Arg Ser Leu Gly Val Ala Tyr
465                 470                 475                 480

Gln Asp Val Pro Asp Arg Arg Lys Glu Ser Pro Gly Ser Pro Trp His
                485                 490                 495
```

-continued

Phe Val Ala Leu Leu Pro Leu Phe Asp Pro Pro Arg His Asp Ser Ala
500 505 510

Glu Thr Ile Gln Arg Ala Leu Asn Leu Gly Val Asn Val Lys Met Ile
515 520 525

Thr Gly Asp Gln Leu Ala Ile Gly Lys Glu Thr Gly Arg Arg Leu Gly
530 535 540

Met Gly Thr Asn Met Tyr Pro Ser Ser Ala Leu Leu Gly Gln Asn Lys
545 550 555 560

Asp Glu Ser Ile Ala Asp Leu Pro Val Asp Asp Leu Ile Glu Lys Ala
565 570 575

Asp Gly Phe Ala Gly Val Phe Pro Glu His Lys Tyr Glu Ile Val Lys
580 585 590

Arg Leu Gln Ala Arg Lys His Ile Cys Gly Met Thr Gly Asp Gly Val
595 600 605

Asn Asp Ala Pro Ala Leu Lys Lys Ala Asp Ile Gly Ile Ala Val Ala
610 615 620

Asp Ala Thr Asp Ala Ala Arg Ser Ala Ser Asp Ile Val Leu Thr Glu
625 630 635 640

Pro Gly Leu Ser Val Ile Ile Ser Ala Val Leu Thr Ser Arg Ala Ile
645 650 655

Phe Gln Arg Met Lys Asn Tyr Thr Ile Tyr Ala Val Ser Ile Thr Ile
660 665 670

Arg Ile Val Leu Gly Phe Met Leu Leu Ala Leu Ile Trp Glu Phe Asp
675 680 685

Phe Pro Pro Phe Met Val Leu Ile Ile Ala Ile Leu Asn Asp Gly Thr
690 695 700

Ile Met Thr Ile Ser Lys Asp Arg Val Lys Pro Ser Pro Leu Pro Asp
705 710 715 720

Ser Trp Lys Leu Ala Glu Ile Phe Thr Thr Gly Val Val Leu Gly Gly
725 730 735

Tyr Leu Ala Met Met Thr Val Ile Phe Phe Trp Ala Ala Tyr Lys Thr
740 745 750

Asn Phe Phe Pro Arg Val Phe His Val Lys Ser Leu Glu Lys Thr Ala
755 760 765

Gln Asp Asp Phe Lys Met Leu Ala Ser Ala Val Tyr Leu Gln Val Ser
770 775 780

Thr Ile Ser Gln Ala Leu Ile Phe Val Thr Arg Ser Arg Ser Trp Ser
785 790 795 800

Phe Val Glu Arg Pro Gly Phe Leu Leu Val Phe Ala Phe Phe Val Ala
805 810 815

Gln Leu Ile Ala Thr Leu Ile Ala Val Tyr Ala Asp Trp Gly Phe Thr
820 825 830

Ser Ile Lys Gly Ile Gly Trp Gly Trp Ala Gly Ile Val Trp Leu Tyr
835 840 845

Asn Ile Val Phe Tyr Phe Pro Leu Asp Ile Ile Lys Phe Phe Ile Arg
850 855 860

Tyr Ala Leu Ser Gly Lys Ala Trp Asp Leu Val Ile Asp Gln Arg Ile
865 870 875 880

Ala Phe Thr Arg Lys Lys His Phe Gly Lys Glu Glu Arg Glu Leu Lys
885 890 895

Trp Ala His Ala Gln Arg Thr Leu His Gly Leu Gln Pro Pro Asp Ala
900 905 910

Lys Leu Phe Pro Glu Lys Ala Gly Tyr Asn Glu Leu Asn Gln Met Ala

```
        915                 920                 925

Glu Glu Ala Lys Arg Arg Ala Glu Ile Ala Arg Leu Arg Glu Leu His
    930                 935                 940

Thr Leu Lys Gly His Val Glu Ser Val Val Lys Leu Lys Gly Leu Asp
945                 950                 955                 960

Ile Asp Thr Ile Gln Gln Ser Tyr Thr Val
                965                 970


<210> SEQ ID NO 5
<211> LENGTH: 970
<212> TYPE: PRT
<213> ORGANISM: Aegilops peregrina
<220> FEATURE:
<221> NAME/KEY: MISC_FEATURE
<222> LOCATION: (824)..(824)
<223> OTHER INFORMATION: Proline mutated from Alanine in KU37 (SEQ ID
      no. 4)

<400> SEQUENCE: 5

Met Ala Ser Ser Arg Gln Glu Gly Asn Leu Asp Ala Val Leu Lys Glu
1               5                   10                  15

Ala Val Asp Leu Glu His Ile Pro Ile Asp Glu Val Phe Glu Asn Leu
            20                  25                  30

Arg Cys Ser His Glu Gly Leu Ala Ser Glu Gln Ala Gln Gln Arg Leu
        35                  40                  45

Gln Ile Phe Gly Pro Asn Lys Leu Glu Glu Lys Glu Glu Ser Lys Phe
    50                  55                  60

Leu Lys Phe Leu Gly Phe Met Trp Asn Pro Leu Ser Trp Val Met Glu
65                  70                  75                  80

Ala Ala Ala Ile Met Ala Ile Ala Leu Ala Asn Gly Gly Gly Lys Pro
                85                  90                  95

Pro Asp Trp Gln Asp Phe Val Gly Ile Ile Thr Leu Leu Leu Ile Asn
            100                 105                 110

Ser Thr Ile Ser Phe Ile Glu Glu Asn Asn Ala Gly Asn Ala Ala Ala
        115                 120                 125

Ala Leu Met Ala Arg Leu Ala Pro Lys Ala Lys Val Leu Arg Asp Gly
    130                 135                 140

Arg Trp Thr Glu Glu Glu Ala Ala Val Leu Val Pro Gly Asp Ile Ile
145                 150                 155                 160

Ser Ile Lys Leu Gly Asp Ile Ile Pro Ala Asp Ala Arg Leu Leu Asp
                165                 170                 175

Gly Asp Pro Leu Lys Ile Asp Gln Ser Ala Leu Thr Gly Glu Ser Leu
            180                 185                 190

Pro Ala Thr Lys Gly Pro Gly Asp Gly Val Tyr Ser Gly Ser Thr Val
        195                 200                 205

Lys Gln Gly Glu Ile Glu Ala Val Val Ile Ala Thr Gly Val His Thr
    210                 215                 220

Phe Phe Gly Lys Ala Ala His Leu Val Asp Ser Thr Asn Gln Val Gly
225                 230                 235                 240

His Phe Gln Gln Ala Ser Leu Thr Ser Leu Gly Tyr Phe Tyr Arg Ile
                245                 250                 255

Val Leu Thr Ala Ile Gly Asn Phe Cys Ile Cys Ser Ile Gly Val Gly
            260                 265                 270

Met Phe Ile Glu Ile Ile Val Met Tyr Pro Ile Gln His Arg Ala Tyr
        275                 280                 285

Arg Pro Gly Ile Asp Asn Leu Leu Val Leu Leu Ile Gly Gly Ile Pro
```

```
    290                 295                 300

Ile Ala Met Pro Thr Val Leu Ser Val Thr Met Ala Ile Gly Ser His
305                 310                 315                 320

Arg Leu Ser Gln Gln Gly Ala Ile Thr Lys Arg Met Thr Ala Ile Glu
                325                 330                 335

Glu Met Ala Gly Met Asp Val Leu Cys Ser Asp Lys Thr Gly Thr Leu
            340                 345                 350

Thr Leu Asn Lys Leu Ser Val Asp Lys Asn Leu Ile Glu Val Phe Glu
        355                 360                 365

Lys Gly Val Thr Gln Asp Gln Val Ile Leu Met Ala Ala Arg Ala Ser
    370                 375                 380

Arg Ile Glu Asn Gln Asp Ala Ile Asp Thr Ala Ile Val Gly Met Leu
385                 390                 395                 400

Gly Asp Pro Lys Glu Ala Arg Ala Gly Ile Gln Glu Val His Phe Leu
                405                 410                 415

Pro Phe Asn Pro Thr Asp Lys Arg Thr Ala Leu Thr Tyr Ile Asp Gly
            420                 425                 430

Asp Gly Lys Met Tyr Arg Val Ser Lys Gly Ala Pro Glu Gln Ile Leu
        435                 440                 445

Asn Leu Ala Tyr Asn Lys Ser Glu Ile Ala Gln Lys Val His Thr Val
    450                 455                 460

Ile Asp Lys Phe Ala Glu Arg Gly Leu Arg Ser Leu Gly Val Ala Tyr
465                 470                 475                 480

Gln Asp Val Pro Asp Arg Arg Lys Glu Ser Pro Gly Ser Pro Trp His
                485                 490                 495

Phe Val Ala Leu Leu Pro Leu Phe Asp Pro Pro Arg His Asp Ser Ala
            500                 505                 510

Glu Thr Ile Gln Arg Ala Leu Asn Leu Gly Val Asn Val Lys Met Ile
        515                 520                 525

Thr Gly Asp Gln Leu Ala Ile Gly Lys Glu Thr Gly Arg Arg Leu Gly
    530                 535                 540

Met Gly Thr Asn Met Tyr Pro Ser Ser Ala Leu Leu Gly Gln Asn Lys
545                 550                 555                 560

Asp Glu Ser Ile Ala Asp Leu Pro Val Asp Asp Leu Ile Glu Lys Ala
                565                 570                 575

Asp Gly Phe Ala Gly Val Phe Pro Glu His Lys Tyr Glu Ile Val Lys
            580                 585                 590

Arg Leu Gln Ala Arg Lys His Ile Cys Gly Met Thr Gly Asp Gly Val
        595                 600                 605

Asn Asp Ala Pro Ala Leu Lys Lys Ala Asp Ile Gly Ile Ala Val Ala
    610                 615                 620

Asp Ala Thr Asp Ala Ala Arg Ser Ala Ser Asp Ile Val Leu Thr Glu
625                 630                 635                 640

Pro Gly Leu Ser Val Ile Ile Ser Ala Val Leu Thr Ser Arg Ala Ile
                645                 650                 655

Phe Gln Arg Met Lys Asn Tyr Thr Ile Tyr Ala Val Ser Ile Thr Ile
            660                 665                 670

Arg Ile Val Leu Gly Phe Met Leu Leu Ala Leu Ile Trp Glu Phe Asp
        675                 680                 685

Phe Pro Pro Phe Met Val Leu Ile Ile Ala Ile Leu Asn Asp Gly Thr
    690                 695                 700

Ile Met Thr Ile Ser Lys Asp Arg Val Lys Pro Ser Pro Leu Pro Asp
705                 710                 715                 720
```

Ser Trp Lys Leu Ala Glu Ile Phe Thr Thr Gly Val Val Leu Gly Gly
725 730 735

Tyr Leu Ala Met Met Thr Val Ile Phe Phe Trp Ala Ala Tyr Lys Thr
740 745 750

Asn Phe Phe Pro Arg Val Phe His Val Lys Ser Leu Glu Lys Thr Ala
755 760 765

Gln Asp Asp Phe Lys Met Leu Ala Ser Ala Val Tyr Leu Gln Val Ser
770 775 780

Thr Ile Ser Gln Ala Leu Ile Phe Val Thr Arg Ser Arg Ser Trp Ser
785 790 795 800

Phe Val Glu Arg Pro Gly Phe Leu Leu Val Phe Ala Phe Phe Val Ala
805 810 815

Gln Leu Ile Ala Thr Leu Ile Pro Val Tyr Ala Asp Trp Gly Phe Thr
820 825 830

Ser Ile Lys Gly Ile Gly Trp Gly Trp Ala Gly Ile Val Trp Leu Tyr
835 840 845

Asn Ile Val Phe Tyr Phe Pro Leu Asp Ile Ile Lys Phe Phe Ile Arg
850 855 860

Tyr Ala Leu Ser Gly Lys Ala Trp Asp Leu Val Ile Asp Gln Arg Ile
865 870 875 880

Ala Phe Thr Arg Lys Lys His Phe Gly Lys Glu Glu Arg Glu Leu Lys
885 890 895

Trp Ala His Ala Gln Arg Thr Leu His Gly Leu Gln Pro Pro Asp Ala
900 905 910

Lys Leu Phe Pro Glu Lys Ala Gly Tyr Asn Glu Leu Asn Gln Met Ala
915 920 925

Glu Glu Ala Lys Arg Arg Ala Glu Ile Ala Arg Leu Arg Glu Leu His
930 935 940

Thr Leu Lys Gly His Val Glu Ser Val Val Lys Leu Lys Gly Leu Asp
945 950 955 960

Ile Asp Thr Ile Gln Gln Ser Tyr Thr Val
965 970

<210> SEQ ID NO 6
<211> LENGTH: 933
<212> TYPE: PRT
<213> ORGANISM: Aegilops crassa
<220> FEATURE:
<221> NAME/KEY: MISC_FEATURE
<222> LOCATION: (475)..(475)
<223> OTHER INFORMATION: Leucine mutated from Proline in KU37 (SEQ ID no. 4)

<400> SEQUENCE: 6

Ala Val Asp Leu Glu His Ile Pro Ile Asp Glu Val Phe Glu Lys Leu
1 5 10 15

Arg Cys Ser His Gln Gly Leu Thr Ser Glu Gln Ala Gln Gln Arg Leu
20 25 30

Gln Ile Phe Gly Pro Asn Lys Leu Glu Glu Lys Glu Glu Ser Lys Phe
35 40 45

Leu Lys Phe Leu Gly Phe Met Trp Asn Pro Leu Ser Trp Val Met Glu
50 55 60

Ala Ala Ala Ile Met Ala Ile Ala Leu Ala Asn Gly Gly Gly Lys Pro
65 70 75 80

Pro Asp Trp Gln Asp Phe Val Gly Ile Ile Thr Leu Leu Leu Val Asn
85 90 95

```
Ser Thr Ile Ser Phe Ile Glu Glu Asn Asn Ala Gly Asn Ala Ala Ala
            100                 105                 110

Ala Leu Met Ala Arg Leu Ala Pro Lys Ala Lys Val Leu Arg Asp Gly
        115                 120                 125

Arg Trp Thr Glu Glu Glu Ala Ala Val Leu Val Pro Gly Asp Ile Val
    130                 135                 140

Ser Ile Lys Leu Gly Asp Ile Ile Pro Ala Asp Ala Arg Leu Leu Asp
145                 150                 155                 160

Gly Asp Pro Leu Lys Ile Asp Gln Ser Ala Leu Thr Gly Glu Ser Leu
                165                 170                 175

Pro Ala Thr Lys Gly Pro Gly Asp Gly Val Tyr Ser Gly Ser Thr Val
            180                 185                 190

Lys Gln Gly Glu Ile Glu Ala Val Val Ile Ala Thr Gly Val His Thr
        195                 200                 205

Phe Phe Gly Lys Ala Ala His Leu Val Asp Ser Thr Asn Gln Val Gly
    210                 215                 220

His Phe Gln Gln Ala Ser Leu Thr Ser Leu Gly Tyr Phe Tyr Arg Ile
225                 230                 235                 240

Val Leu Thr Ala Ile Gly Asn Phe Cys Ile Cys Ser Ile Ala Val Gly
                245                 250                 255

Met Phe Ile Glu Ile Ile Val Met Tyr Pro Ile Gln His Arg Ala Tyr
            260                 265                 270

Arg Pro Gly Ile Asp Asn Leu Leu Val Leu Leu Ile Gly Gly Ile Pro
        275                 280                 285

Ile Ala Met Pro Thr Val Leu Ser Val Thr Met Ala Ile Gly Ser His
    290                 295                 300

Arg Leu Ser Gln Gln Gly Ala Ile Thr Lys Arg Met Thr Ala Ile Glu
305                 310                 315                 320

Glu Met Ala Gly Met Asp Val Leu Cys Ser Asp Lys Thr Gly Thr Leu
                325                 330                 335

Thr Leu Asn Lys Leu Ser Val Asp Lys Asn Ile Ile Glu Val Phe Glu
            340                 345                 350

Lys Gly Val Thr Gln Asp Gln Val Ile Leu Met Ala Ala Arg Ala Ser
        355                 360                 365

Arg Ile Glu Asn Gln Asp Ala Ile Asp Thr Ala Ile Val Gly Met Leu
    370                 375                 380

Gly Asp Pro Lys Glu Ala Arg Ala Gly Ile Gln Glu Ile His Phe Leu
385                 390                 395                 400

Pro Phe Asn Pro Thr Asp Lys Arg Thr Ala Leu Thr Tyr Ile Asp Ser
                405                 410                 415

Asp Gly Lys Met Tyr Arg Val Ser Lys Gly Ala Pro Glu Gln Ile Leu
            420                 425                 430

Asn Leu Ala Tyr Asn Lys Ser Glu Ile Ala Gln Lys Val His Thr Val
        435                 440                 445

Ile Asp Lys Phe Ala Glu Arg Gly Leu Arg Ser Leu Gly Val Ala Tyr
    450                 455                 460

Gln Asp Val Pro Asp Gly Arg Lys Glu Ser Leu Gly Ser Pro Trp His
465                 470                 475                 480

Phe Val Ala Leu Leu Pro Leu Phe Asp Pro Pro Arg His Asp Ser Ala
                485                 490                 495

Glu Thr Ile Gln Arg Ala Leu Asn Leu Gly Val Asn Val Lys Met Ile
            500                 505                 510
```

-continued

```
Thr Gly Asp Gln Leu Ala Ile Gly Lys Glu Thr Gly Arg Arg Leu Gly
        515                 520                 525

Met Gly Thr Asn Met Tyr Pro Ser Ser Ala Leu Leu Gly Gln Asn Lys
    530                 535                 540

Asp Glu Ser Ile Ala Asp Leu Pro Val Asp Asp Leu Ile Glu Lys Ala
545                 550                 555                 560

Asp Gly Phe Ala Gly Val Phe Pro Glu His Lys Tyr Glu Ile Val Lys
                565                 570                 575

Arg Leu Gln Ala Arg Lys His Ile Cys Gly Met Thr Gly Asp Gly Val
            580                 585                 590

Asn Asp Ala Pro Ala Leu Lys Lys Ala Asp Ile Gly Ile Ala Val Ala
        595                 600                 605

Asp Ala Thr Asp Ala Ala Arg Ser Ala Ser Asp Ile Val Leu Thr Glu
    610                 615                 620

Pro Gly Leu Ser Val Ile Ile Ser Ala Val Leu Thr Ser Arg Ala Ile
625                 630                 635                 640

Phe Gln Arg Met Lys Asn Tyr Thr Ile Tyr Ala Val Ser Ile Thr Ile
                645                 650                 655

Arg Ile Val Leu Gly Phe Met Leu Leu Ala Leu Ile Trp Glu Phe Asp
            660                 665                 670

Phe Pro Pro Phe Met Val Leu Ile Ile Ala Ile Leu Asn Asp Gly Thr
        675                 680                 685

Ile Met Thr Ile Ser Lys Asp Arg Val Lys Pro Ser Pro Leu Pro Asp
    690                 695                 700

Ser Trp Lys Leu Ala Glu Ile Phe Thr Thr Gly Val Val Leu Gly Gly
705                 710                 715                 720

Tyr Leu Ala Met Met Thr Val Ile Phe Phe Trp Ala Ala Tyr Lys Thr
                725                 730                 735

Asn Phe Phe Pro Arg Val Phe His Val Lys Ser Leu Glu Lys Thr Ala
            740                 745                 750

Gln Asp Asp Phe Lys Met Leu Ala Ser Ala Val Tyr Leu Gln Val Ser
        755                 760                 765

Thr Ile Ser Gln Ala Leu Ile Phe Val Thr Arg Ser Arg Ser Trp Ser
    770                 775                 780

Phe Val Glu Arg Pro Gly Phe Leu Leu Val Phe Ala Phe Leu Val Ala
785                 790                 795                 800

Gln Leu Ile Ala Thr Leu Ile Ala Val Tyr Ala Asp Trp Gly Phe Thr
                805                 810                 815

Ser Ile Lys Gly Ile Gly Trp Gly Trp Ala Gly Ile Val Trp Leu Tyr
            820                 825                 830

Asn Ile Val Phe Tyr Phe Pro Leu Asp Ile Ile Lys Phe Phe Ile Arg
        835                 840                 845

Tyr Ala Leu Ser Gly Lys Ala Trp Asp Leu Val Ile Asp Gln Arg Ile
    850                 855                 860

Ala Phe Thr Arg Lys Lys His Phe Gly Lys Glu Glu Arg Glu Leu Lys
865                 870                 875                 880

Trp Ala His Ala Gln Arg Thr Leu His Gly Leu Gln Pro Pro Asn Ala
                885                 890                 895

Lys Leu Phe Pro Glu Lys Ala Gly Tyr Asn Glu Leu Cys Gln Met Ala
            900                 905                 910

Glu Glu Ala Lys Arg Arg Ala Glu Ile Ala Arg Leu Arg Glu Leu His
        915                 920                 925

Thr Leu Lys Gly His
```

930

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 7
aactacagat tcatgacagg 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 8
ctactgctac ctcctctctt 20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 9
acggattagt cacaacaagc 20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 10
gttgggaaga cagataatgc 20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 11
ggartttgat ttcccgccat 20

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 12
gcagcccaga agaaaatgac a 21

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 13
atctggtacc tgatttcata gtga 24

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 14
ccacaactgt accattatct actgc 25

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 15
caaggacgca atctcacca 19

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 16
gcaacgagga gatgagcc 18

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 17
caagttctct acggtttgga gt 22

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 18
ttgatcaaga gaatggggat 20

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 19
atgacacctt tatttcagcc ag 22

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 20
agctcggtct gcatttga 18

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 21
cgctcaccat cacccaag 18

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 22
gagctgaagc gaacgaac 18

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 23
tgccatcatc ggtagtcatt 20

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 24
tggtgtgctg ttgatcctt 19

```
<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25

gatgagccgc ctccccat                                                   18


<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26

cctttgctga tgcagttcg                                                  19


<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27

tggaacactg ccatcgtg                                                   18


<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28

ggtggagcga gatatgagat c                                               21


<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29

ggctttgata ctggaacgaa t                                               21


<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30

cagtgtaagg ctctgttgcg                                                 20


<210> SEQ ID NO 31
```

```
<211> LENGTH: 54
<212> TYPE: PRT
<213> ORGANISM: Aegilops tauschii

<400> SEQUENCE: 31

Val Ile Asp Lys Phe Ala Glu Arg Gly Phe Arg Ser Leu Gly Val Ala
1               5                   10                  15

Tyr Gln Asp Val Pro Asp Gly Arg Lys Glu Ser Pro Gly Ser Pro Trp
            20                  25                  30

His Phe Val Ala Leu Leu Pro Leu Phe Asp Pro Pro Arg His Asp Ser
        35                  40                  45

Ala Glu Thr Ile Gln Arg
    50


<210> SEQ ID NO 32
<211> LENGTH: 54
<212> TYPE: PRT
<213> ORGANISM: Triticum urartu

<400> SEQUENCE: 32

Val Ile Asp Lys Phe Ala Glu Arg Gly Leu Arg Ser Leu Gly Val Ala
1               5                   10                  15

Tyr Gln Asp Val Pro Asp Gly Arg Lys Glu Ser Pro Gly Ser Pro Trp
            20                  25                  30

His Phe Val Ala Leu Leu Pro Leu Phe Asp Pro Pro Arg His Asp Ser
        35                  40                  45

Ala Glu Thr Ile Gln Arg
    50


<210> SEQ ID NO 33
<211> LENGTH: 54
<212> TYPE: PRT
<213> ORGANISM: Triticum aestivum

<400> SEQUENCE: 33

Val Ile Asp Lys Phe Ala Glu Arg Gly Leu Arg Ser Leu Gly Val Ala
1               5                   10                  15

Tyr Gln Asp Val Pro Asp Gly Arg Lys Glu Ser Pro Gly Ser Pro Trp
            20                  25                  30

His Phe Val Ala Leu Leu Pro Leu Phe Asp Pro Pro Arg His Asp Ser
        35                  40                  45

Ala Glu Thr Ile Gln Arg
    50


<210> SEQ ID NO 34
<211> LENGTH: 54
<212> TYPE: PRT
<213> ORGANISM: Triticum aestivum

<400> SEQUENCE: 34

Val Ile Asp Lys Phe Ala Glu Arg Gly Leu Arg Ser Leu Gly Val Ala
1               5                   10                  15

Tyr Gln Asp Val Pro Asp Gly Arg Lys Glu Ser Pro Gly Ser Pro Trp
            20                  25                  30

His Phe Val Ala Leu Leu Pro Leu Phe Asp Pro Pro Arg His Asp Ser
        35                  40                  45

Ala Glu Thr Ile Gln Arg
    50
```

<210> SEQ ID NO 35
<211> LENGTH: 54
<212> TYPE: PRT
<213> ORGANISM: Hordeum vulgare

<400> SEQUENCE: 35

```
Val Ile Asp Lys Phe Ala Glu Arg Gly Leu Arg Ser Leu Gly Val Ala
1               5                   10                  15

Tyr Gln Asp Val Pro Asp Gly Arg Lys Glu Ser Pro Gly Ser Pro Trp
            20                  25                  30

His Phe Val Ala Leu Leu Pro Leu Phe Asp Pro Pro Arg His Asp Ser
        35                  40                  45

Ala Glu Thr Ile Glu Arg
    50
```

<210> SEQ ID NO 36
<211> LENGTH: 54
<212> TYPE: PRT
<213> ORGANISM: Brachypodium distachyon

<400> SEQUENCE: 36

```
Val Ile Asp Lys Phe Ala Glu Arg Gly Leu Arg Ser Leu Gly Val Ala
1               5                   10                  15

Tyr Gln Asp Val Pro Asp Gly Arg Lys Glu Ser Pro Gly Arg Pro Trp
            20                  25                  30

His Phe Val Ala Leu Leu Pro Leu Phe Asp Pro Pro Arg His Asp Ser
        35                  40                  45

Ala Glu Thr Ile Gln Arg
    50
```

<210> SEQ ID NO 37
<211> LENGTH: 54
<212> TYPE: PRT
<213> ORGANISM: Oryza sativa
<220> FEATURE:
<223> OTHER INFORMATION: Japonica

<400> SEQUENCE: 37

```
Val Ile Asp Lys Phe Ala Glu Arg Gly Leu Arg Ser Leu Ala Val Ala
1               5                   10                  15

Tyr Gln Glu Val Pro Asp Gly Arg Lys Glu Ser Pro Gly Gly Pro Trp
            20                  25                  30

Arg Phe Val Ala Leu Leu Pro Leu Phe Asp Pro Pro Arg His Asp Ser
        35                  40                  45

Ala Glu Thr Ile Arg Arg
    50
```

<210> SEQ ID NO 38
<211> LENGTH: 54
<212> TYPE: PRT
<213> ORGANISM: Oryza sativa
<220> FEATURE:
<223> OTHER INFORMATION: Indica

<400> SEQUENCE: 38

```
Val Ile Asp Lys Phe Ala Glu Arg Gly Leu Arg Ser Leu Ala Val Ala
1               5                   10                  15

Tyr Gln Glu Val Pro Asp Gly Arg Lys Glu Ser Pro Gly Gly Pro Trp
            20                  25                  30

Arg Phe Val Ala Leu Leu Pro Leu Phe Asp Pro Pro Arg His Asp Ser
        35                  40                  45
```

```
Ala Glu Thr Ile Arg Arg
    50


<210> SEQ ID NO 39
<211> LENGTH: 54
<212> TYPE: PRT
<213> ORGANISM: Setaria italica

<400> SEQUENCE: 39

Val Ile Asp Lys Phe Ala Glu Arg Gly Leu Arg Ser Leu Ala Val Ala
1               5                   10                  15

Tyr Gln Glu Val Pro Asp Gly Arg Lys Glu Ser Pro Gly Gly Pro Trp
            20                  25                  30

His Phe Val Ala Leu Leu Pro Leu Phe Asp Pro Pro Arg His Asp Ser
        35                  40                  45

Ala Glu Thr Ile Arg Arg
    50


<210> SEQ ID NO 40
<211> LENGTH: 54
<212> TYPE: PRT
<213> ORGANISM: Zea mays

<400> SEQUENCE: 40

Val Ile Asp Lys Phe Ala Glu Arg Gly Leu Arg Ser Leu Ala Val Ala
1               5                   10                  15

Tyr Gln Val Val Pro Asp Gly Arg Lys Glu Ser Pro Gly Gly Pro Trp
            20                  25                  30

His Phe Val Ala Leu Leu Pro Leu Phe Asp Pro Pro Arg His Asp Ser
        35                  40                  45

Ala Glu Thr Ile Arg Arg
    50


<210> SEQ ID NO 41
<211> LENGTH: 54
<212> TYPE: PRT
<213> ORGANISM: Sorghum bicolor

<400> SEQUENCE: 41

Val Ile Asp Lys Phe Ala Glu Arg Gly Leu Arg Ser Leu Ala Val Ala
1               5                   10                  15

Tyr Gln Glu Val Pro Asp Gly Arg Lys Glu Ser Pro Gly Gly Pro Trp
            20                  25                  30

His Phe Val Ala Leu Leu Pro Leu Phe Asp Pro Pro Arg His Asp Ser
        35                  40                  45

Ala Glu Thr Ile Gln Arg
    50


<210> SEQ ID NO 42
<211> LENGTH: 53
<212> TYPE: PRT
<213> ORGANISM: Aegilops tauschii

<400> SEQUENCE: 42

Trp Ser Phe Val Glu Arg Pro Gly Phe Leu Leu Val Phe Ala Phe Leu
1               5                   10                  15

Val Ala Gln Leu Ile Ala Thr Leu Ile Ala Val Tyr Ala Asp Trp Gly
            20                  25                  30

Phe Thr Ser Ile Lys Gly Ile Gly Trp Gly Trp Ala Gly Ile Val Trp
```

35 40 45

Leu Tyr Asn Ile Val
50

<210> SEQ ID NO 43
<211> LENGTH: 53
<212> TYPE: PRT
<213> ORGANISM: Triticum urartu

<400> SEQUENCE: 43

Trp Ser Phe Val Glu Arg Pro Gly Phe Leu Leu Val Phe Ala Phe Phe
1 5 10 15

Val Ala Gln Leu Ile Ala Thr Leu Ile Ala Val Tyr Ala Asp Trp Gly
20 25 30

Phe Thr Ser Ile Lys Gly Ile Gly Trp Gly Trp Ala Gly Ile Val Trp
35 40 45

Leu Tyr Asn Ile Val
50

<210> SEQ ID NO 44
<211> LENGTH: 53
<212> TYPE: PRT
<213> ORGANISM: Triticum aestivum

<400> SEQUENCE: 44

Trp Ser Phe Val Glu Arg Pro Gly Phe Leu Leu Val Phe Ala Phe Phe
1 5 10 15

Val Ala Gln Leu Ile Ala Thr Leu Ile Ala Val Tyr Ala Asp Trp Gly
20 25 30

Phe Thr Ser Ile Lys Gly Ile Gly Trp Gly Trp Ala Gly Ile Val Trp
35 40 45

Leu Tyr Asn Ile Val
50

<210> SEQ ID NO 45
<211> LENGTH: 53
<212> TYPE: PRT
<213> ORGANISM: Triticum aestivum

<400> SEQUENCE: 45

Trp Ser Phe Ile Glu Arg Pro Gly Phe Leu Leu Val Phe Ala Phe Leu
1 5 10 15

Val Ala Gln Leu Ile Ala Thr Leu Ile Ala Val Tyr Ala Asp Trp Gly
20 25 30

Phe Thr Ser Ile Lys Gly Ile Gly Trp Gly Trp Ala Gly Ile Val Trp
35 40 45

Leu Tyr Asn Ile Val
50

<210> SEQ ID NO 46
<211> LENGTH: 53
<212> TYPE: PRT
<213> ORGANISM: Hordeum vulgare

<400> SEQUENCE: 46

Trp Ser Phe Leu Glu Arg Pro Gly Phe Leu Leu Val Phe Ala Phe Phe
1 5 10 15

Val Ala Gln Leu Ile Ala Thr Leu Ile Ala Val Tyr Ala Asp Trp Ala
20 25 30

```
Phe Thr Ser Ile Lys Gly Ile Gly Trp Gly Trp Ala Gly Ile Val Trp
        35                  40                  45

Leu Tyr Asn Ile Val
    50


<210> SEQ ID NO 47
<211> LENGTH: 53
<212> TYPE: PRT
<213> ORGANISM: Brachypodium distachyon

<400> SEQUENCE: 47

Trp Ser Phe Val Glu Arg Pro Gly Phe Leu Leu Val Phe Ala Phe Phe
1               5                   10                  15

Val Ala Gln Leu Ile Ala Thr Leu Ile Ala Val Tyr Ala Asp Trp Gly
            20                  25                  30

Phe Thr Ser Ile Lys Gly Ile Gly Trp Gly Trp Ala Gly Thr Val Trp
        35                  40                  45

Leu Tyr Asn Ile Val
    50


<210> SEQ ID NO 48
<211> LENGTH: 53
<212> TYPE: PRT
<213> ORGANISM: Oryza sativa
<220> FEATURE:
<223> OTHER INFORMATION: Japonica

<400> SEQUENCE: 48

Trp Ser Phe Ile Glu Arg Pro Gly Phe Leu Leu Val Phe Ala Phe Phe
1               5                   10                  15

Val Ala Gln Leu Ile Ala Thr Leu Ile Ala Val Tyr Ala Asp Trp Ala
            20                  25                  30

Phe Thr Ser Ile Lys Gly Ile Gly Trp Gly Trp Ala Gly Ile Val Trp
        35                  40                  45

Leu Tyr Asn Ile Val
    50


<210> SEQ ID NO 49
<211> LENGTH: 53
<212> TYPE: PRT
<213> ORGANISM: Oryza sativa
<220> FEATURE:
<223> OTHER INFORMATION: Indica

<400> SEQUENCE: 49

Trp Ser Phe Ile Glu Arg Pro Gly Phe Leu Leu Val Phe Ala Phe Phe
1               5                   10                  15

Val Ala Gln Leu Ile Ala Thr Leu Ile Ala Val Tyr Ala Asp Trp Ala
            20                  25                  30

Phe Thr Ser Ile Lys Gly Ile Gly Trp Gly Trp Ala Gly Ile Val Trp
        35                  40                  45

Leu Tyr Asn Ile Val
    50


<210> SEQ ID NO 50
<211> LENGTH: 53
<212> TYPE: PRT
<213> ORGANISM: Setaria italica

<400> SEQUENCE: 50

Trp Ser Phe Val Glu Arg Pro Gly Phe Leu Leu Val Phe Ala Phe Leu
```

-continued

```
1               5                   10                  15

Val Ala Gln Leu Ile Ala Thr Leu Ile Ala Val Tyr Ala Asp Trp Gly
            20                  25                  30

Phe Thr Ser Ile Lys Gly Ile Gly Trp Gly Trp Ala Gly Val Val Trp
        35                  40                  45

Leu Tyr Asn Ile Val
    50


<210> SEQ ID NO 51
<211> LENGTH: 53
<212> TYPE: PRT
<213> ORGANISM: Zea mays

<400> SEQUENCE: 51

Trp Ser Phe Ala Glu Arg Pro Gly Phe Leu Leu Val Phe Ala Phe Leu
1               5                   10                  15

Val Ala Gln Leu Ile Ala Thr Leu Ile Ala Val Tyr Ala Asp Trp Gly
            20                  25                  30

Phe Thr Ser Ile Lys Gly Ile Gly Trp Gly Trp Ala Gly Val Val Trp
        35                  40                  45

Leu Tyr Asn Ile Val
    50


<210> SEQ ID NO 52
<211> LENGTH: 53
<212> TYPE: PRT
<213> ORGANISM: Sorghum bicolor

<400> SEQUENCE: 52

Trp Ser Phe Val Glu Arg Pro Gly Phe Leu Leu Val Phe Ala Phe Leu
1               5                   10                  15

Val Ala Gln Leu Ile Ala Thr Leu Ile Val Val Tyr Ala Asp Trp Gly
            20                  25                  30

Phe Thr Ser Ile Lys Gly Ile Gly Trp Gly Trp Ala Gly Val Val Trp
        35                  40                  45

Leu Tyr Asn Ile Val
    50


<210> SEQ ID NO 53
<211> LENGTH: 7572
<212> TYPE: DNA
<213> ORGANISM: Triticum aestivum
<220> FEATURE:
<221> NAME/KEY: modified_base
<222> LOCATION: (208)..(388)
<223> OTHER INFORMATION: a, c, g, or t

<400> SEQUENCE: 53

cagacgcagg cacggcaacg ggtcacggag agctcgccgc ggcagggacg tgacgtgtgt      60

ggtggtggac ggcgctcgcg tggctcagtt ttttttcccc gtttcccccc ctccctcctc     120

cgctctccag tccagggaaa gctcccgccc tcgccgctcg gggagcggca gagaaatgcg     180

acggcgatgc ccccccttcct cccctcgnnn nnnnnnnnnn nnnnnnnnnn nnnnnnnnnn     240

nnnnnnnnnn nnnnnnnnnn nnnnnnnnnn nnnnnnnnnn nnnnnnnnnn nnnnnnnnnn     300

nnnnnnnnnn nnnnnnnnnn nnnnnnnnnn nnnnnnnnnn nnnnnnnnnn nnnnnnnnnn     360

nnnnnnnnnn nnnnnnnnnn nnnnnnnngc cgccaccgcg tcttcgccgc cgccgccgcc     420

tacgggccgc agccctgccg cggccgcgtc tgcgtctgcg ccgcctacag gcccccgccg     480
```

cggcagccct accgccgcca gcccgccccc gccccggccc cgcgcccgcc caatgcgccc 540
gcgccgccgc agcgcggccc gcggggccag gaggagctcg aggaggcgat ctacgacttc 600
atgcgccgct ccgacaagcc cggcgccttc cccacccgcg ccgagctcct cgccgcgggg 660
cgcgccgacc tcgccgccgc cgtcgagtcc agcggaggct ggctctccct cggatggtcc 720
tggtcctccg acgacgacgc gcggcggccg gctgcgtcaa cggccggccc cggcgtgcac 780
cctgaatacc cgcccgaggc gggtccttct ggccgaccgc caaactcggc cgcggattcc 840
gtaaggtggg taaccgagcc gctctgtaat gtaatgtgtc cccctctgtt gattgctctg 900
cgacgacttg ctgaattccg agtgttgcag ggagcagcag gaaccggcgc cgtctgggag 960
gcagccggag acggaggaga cagagtgggt gcctgctaaa tctcttttga gttattttga 1020
ttgatatatg ctggttcctt attgattttg cttgttgcta cgtaatcgat tgcagggagg 1080
cagggtctgg ggcaggcctg gagggaatgc tcgccaggct gcggagagag agggagcgtg 1140
cgcggccacc gccacgcagc aagaatcaag cgggagggcg aggtcaaaat ggcggtatgt 1200
gcagcttcga ctcttggcgt tctatcgaaa catgtgttgt tttcagttgt gcaacatgag 1260
catcttcttt gcaaacagtt atatgtttgt tgataaggga acaccaactt ttgcaaccaa 1320
tgaaactttg catagtatac agctcattgt gccatattgt ttagttacag cccgtggaag 1380
gcttaatgct ctgctggata aaattaatgc taagctcatg ccgggcagga aggaagtgcc 1440
gccgacaata gttcatgcaa aagctgtctg ttctcacgga ccggacttcc ctttcccccg 1500
acatatataa ctagcagtgc agtagtttag cgctttccat ttaaggttgc aaaggggaca 1560
aacataccgt tttttgttct atgtcgcttt ctaaaaatag aagcgtggcg ttagaacttt 1620
ctttctcatg atccgacata ttttttgtcg tcgtgctact gcttaatgta aagttgtttg 1680
caccttgaca gcactgcaat tatttgagta atcgtgaatc tacagaagac taccacatta 1740
ttttgtttgt gccttttaat catagtagta atatgttctg ttacatacaa ctggtttagc 1800
tttgttatta ctctgcccat ttcagcattt ggtccttcca agctaatggc ttttttgtgt 1860
taaatctctt acaatacacg gaggataatt cattttctat ttcaaatatg ctgctgttaa 1920
tagttgcccc ctaacaccta aatgaattga agggtccatg ctccctagat atacatggtt 1980
gattgaagtt agtagactct gcgttttgca aatatattta ctaattaatg accgctttaa 2040
gattgaccat gtgtttaggt attttactga tttagtgcac acggatcatt ttctcggtac 2100
tctattagta tcaacagtaa aaagtacaca ttgtaaactt ttggctggag actcggagag 2160
gaaaattgaa agagttccac cttatataat agaaaatagc gttggtttgt tattgatgga 2220
caactaatgg atatttttg ttagagagct tctggataat tatgtatgtg aacctttatt 2280
ctgatgtacc atatacttaa tttctagctg gtgtttcttc atttgtatat taatgatcat 2340
acttctgtgt tacatacatg cagctttaat gaaccataat ggagctccta gtcgaagtcc 2400
aactaatggc atgtacactc gaaggatacc tgtgaatgga aatatacacc gctctcattc 2460
tcaaaatgga ataccagagg acaacaaatc aagtagttcg gccaatgatg catggcgaac 2520
atggtctctt gacaagagtc ggttttctga ttttgaaggt tatatgataa cttaactttc 2580
tttcgttgcg catcatatct gttatgatta tttcataaca tgtttaatat gctgacagcc 2640
gctgagatcc atcctttgag cagaaaacca ccaaaacatg ttgacctgaa cactgtgttg 2700
atagaagatg atgttcctgg accatctaat ggtgtggtta taaatgatta tcctagtgat 2760
catgtagact ctgaaagaga tgagatacat gcacgttttc aaaatttgga attcgatctt 2820
gcagattctc ttaagacatt aagatcaaga tttgatggag tttcgtcata tatggtgtgt 2880

```
ctcgtctctc gtatcatctt ctttacttat ctatcttttg ttgtgaaata ctggtgggat   2940
acgtgatctt gagattttag tgtggttttg cattcagttt tcttcactta tgcatttgta   3000
aagttgttta tgcattgtac tagacatggc tctgctgttc ctaacaaaac acacctgaag   3060
atgtggttct gcttgctcta attttctctt tatgcactaa acactgtctg catcataccc   3120
tcgcccatca ctagaaaagt gccatctttg gatgcatgca gtcaaatttt ttgattttga   3180
ctaacactgt aacagtatcc tcatcaatat gcagtctgac aacatgaaaa tggtacaagt   3240
tcatttgcca acggaacaac ttccataaat tttgatttta tatctgtaga tattcactgt   3300
atatccacta tcttttcttg caatgttgtg atttcgcaac gcaaacaaat gactatagct   3360
aataatattc ccttgcaatg ctgattgctg aatgtagttg tgttctctac gaggaagtag   3420
ttagctagtc gcaaaataaa aagcacaggt acggagacat ggacacagcg atacgcctag   3480
gggacacggg atacggcatt aaacagccat tcagggatac ggcgagtata tatgaaaaaa   3540
attaaaacat gccatgtaat atagagttaa aaaaatgaag agaaactgag ataagatcag   3600
aatactgccc catttccatt tgttgtattg tttttcaagt gctcaatgat tgaattaatt   3660
gatcctctag acccatgtca ttgcaacttg caaaatacat caaatgctag tattagtcta   3720
ttagagagta gagactggag aagacatgca acaaaggatg caggtgtaac tttcaccctc   3780
acccatggac gattggccac cggtggtggc gctcccaaac gccatgctcc ctaacatcaa   3840
gcaacaatca aaacagcagc accaggcacc agcatgcaag tgagcagcag ctcaagagca   3900
agcagcaacg gcatggacgc atggggaagc aagcagcaga ctcaacagca agaaatcgag   3960
caaagatatg aagaggttga gaagaggctg ctggggttat ctgcttgagc gtggttgcca   4020
tcgggcggtt gagtccaggg ggcggcggtg atagcgcgtt cgacttggag cagcgttcct   4080
ttagtggcaa gcgtgtgtgc gaccttgcaa aatagggttt gtatcgggcc aaggctgtta   4140
ttgagcttcc tgtgtcccca acgtattcca tacgtatccc agctgtgtct ttgttttttc   4200
ctttctttaa ttaggaaatc aggggatact gggggacacg cgtatcttgg catgtccggc   4260
catatcgccg tgtcgcaacg aattaggacg gcaattcggc agtttcggcc gtttccatgc   4320
tttgttggtc gcaatgattt agtttgcaaa ttattacaca ttcttgtttt tagaaccatt   4380
gtattactgg taggaagttt ctgattttcg agacttggcc cacgctgata tgaaactaaa   4440
acgataatgg aagatcttga tgcatctcat cttgattttt ctagaggcaa tatacttgtt   4500
ctgagcatcc atctttgccc ttccattttc cagtcaaatg gcgaagaagc agatgtggta   4560
aatgggttct ctgatgattg ggaatttgaa gagacaaaag taatgcatgc ccaggaagaa   4620
ttacggacaa tccgtgctaa aatagcagta ttagaaggca aggtggcgct agaaataatg   4680
tatggtcact cacaattgaa tgttgttcat ctacgctttt tattttgtat caatctcttt   4740
tatgacttat tctgttgata tcagtgagaa gaacaaaata attgaagaaa agcaaacgag   4800
gcttgatgaa gttgagaagg ctttgagtga gctccgcaca gtatctgttg tatggcccaa   4860
tcctgcttca gaagttctat tgaccggttc ttttgatggg tggacaagcc aagtaagtgc   4920
atgttcctat tctctgctta attagtaaat atataaactt cagtaactaa ctataaaatg   4980
agtggcagtt cgtgatttca atttctatca ctctttggtg ttagttgtca ggtgaattcc   5040
attgatttat gtattaagtt gaatattaat gaagagagaa gctggatcta ttgctgctct   5100
cctaagttgt gtaaatgcaa tttactgcca acaccttatc atgtgcacag ttaattcatt   5160
tcttaatgag tgcaaaacaa acacaatact ccctccggtc catattacgg agggagtact   5220
```

-continued

```
taatttgatg tggttcacac acaagtaaag taacttcagg aactagcaac atgatagtta   5280

cgagaatggt agggatcgaa ggcgcccaag tgctttgaaa gatgtttatt acgtatatgt   5340

ttctaggagt aaagcaagtt tttaatctga ttttggttgt tggtgctgtt tttggcatag   5400

gcacaattgt gacaacacgt gtccataact tttgtgttag aaatactacg tgctatttgg   5460

atttggaagt ttagaaacat tgttttatat gccaaaagaa aaaggaaaag cacatggaat   5520

cttcatatat ttgttaatac tccttccgtt cctttttatg gcttgtattg gtttgttgga   5580

aagtcaaact tttctccctt tgaccaagtt tataaaagaa tcaatgtatg caatactaaa   5640

tacataaaat atggaaatat ttttcatgaa gggtctgatg atactgattt ggcattgtag   5700

atgttgatac ttttttctat ataaacttgg tcaaagatgg aaaaggtgga ctttaaaaaa   5760

acatcttata aaaaggaacg gagggagtat gtatttatca ttttatatta agtggaaact   5820

gaagcagcac aattttacaa gagcttcact aggcaagacc tagcaacaaa tatactacct   5880

ctgcaacttt ttataagaca tttttagagt ctatgacaat gtgaaaaatg tctcatatta   5940

agttagggag ggagtatatc tttatctggt acctttagct gagatttagt cagttcctag   6000

gaggatactg gtcacatgac tgacatatcc aaaaggatgt tcagtagttc aagcacatat   6060

aggataggta ctagatgtag aagcctgaag gacaacattc tgccattata gatcttagtt   6120

tcactttcat atgtatgggg gtgctgttta gttttatttt gtatacatga tatttgcatt   6180

tccatggagc acacaacaca attcagatca gccagcagaa gaatgttagt agtacaaatc   6240

aaatttggtt ctagagtaag aaatattacc tgtgtcccaa attacttgtc ttagatttgt   6300

ctagataggg atgtacctat ctagacaaat ctaagacaag taattcagga cggagggagt   6360

atgaatttgt tatgccattt cacctctctt gtcgctcctt tgatataact ttcaagatat   6420

tgaatattta aacatctaat tatatgaatg tccatggaat gttgtctgct ttgggctgtg   6480

tactgcagga agtctctttg ttacgtactc cctctgtacc gaaatacatg tcgctggagt   6540

agcagtaagt caactactcc agcgacatgt atttcggtac agagggagta atatatatag   6600

ctctgtgctt gcctgcttaa tcacactctg ttccatgtgc ctatgacacg ttttgtcatc   6660

tatctacaca tcatcatcgc tatcgtctta ttcttgagta taatcaaaca ctggactatt   6720

tccttttgt agagaaggat ggaacaatca gaaagcggca ttttttcgta taacctgagg   6780

ttgtatcccg gtagatatga ggtaatggcg tgctattctg ctttcattgt cactgctttc   6840

tcgtcatctg atagtgggtg ttggtttgtg cttcagatta aatttattgt tgatggtgtt   6900

tggaagaacg acccgctgcg ccctagcgtg aacaaccatg ggaacgaaaa caaccttatg   6960

attgtcactt gacctgcatc cttgtagcaa ctgtgtagat tatagattgt catcaacaat   7020

gattggtgcc aactgattag atctcttctt tcttccgtgt agcttatcag tttttcctgc   7080

ctgtcgtttc ttcattattt cttagagagc cacgcacaac ttcagggtgt tgtcttcgcc   7140

ccgctgagat gggagaagaa tgtagctgtt ggtgtgtgtg ttctttcctt ccccctcttt   7200

catctccctg gagaagcata gtggggcact cgaacgcccc ggtggcggtt gggggtagtt   7260

cgccgtcggt gtctcaggtg tgtgtaacaa tgtacatatc ccgtgatagc aaagttgtcc   7320

atggttagtt tgtcaaggtg gtggcgtgcc tgtcagtgtg cacgcactgg ttcttactat   7380

aagatccagg ccgggaactc atccgataga acagagcatg tcatcgttgt gatatgcatt   7440

ggttgggata gctatagctc ggcagaaggt tagcagctcg ggcacaaata cagaacacag   7500

tggaaatgtg agtctccatt gggtcatgac ggtacagttg aaccaaccac aagtacagtg   7560

aaatcgttca tc                                                       7572
```

<210> SEQ ID NO 54
<211> LENGTH: 460
<212> TYPE: PRT
<213> ORGANISM: Triticum aestivum

<400> SEQUENCE: 54

```
Met Arg Arg Ser Asp Lys Pro Gly Ala Phe Pro Thr Arg Ala Glu Leu
1               5                   10                  15

Leu Ala Ala Gly Arg Ala Asp Leu Ala Ala Ala Val Glu Ser Ser Gly
            20                  25                  30

Gly Trp Leu Ser Leu Gly Trp Ser Trp Ser Ser Asp Asp Asp Ala Arg
        35                  40                  45

Arg Pro Ala Ala Ser Thr Ala Gly Pro Gly Val His Pro Glu Tyr Pro
    50                  55                  60

Pro Glu Ala Gly Pro Ser Gly Arg Pro Pro Asn Ser Ala Ala Asp Ser
65                  70                  75                  80

Val Arg Glu Gln Gln Glu Pro Ala Pro Ser Gly Arg Gln Pro Glu Thr
                85                  90                  95

Glu Glu Thr Glu Glu Ala Gly Ser Gly Ala Gly Leu Glu Gly Met Leu
            100                 105                 110

Ala Arg Leu Arg Arg Glu Arg Glu Arg Ala Arg Pro Pro Pro Arg Ser
        115                 120                 125

Lys Asn Gln Ala Gly Gly Arg Gly Gln Asn Gly Ala Leu Met Asn His
    130                 135                 140

Asn Gly Ala Pro Ser Arg Ser Pro Thr Asn Gly Met Tyr Thr Arg Arg
145                 150                 155                 160

Ile Pro Val Asn Gly Asn Ile His Arg Ser His Ser Gln Asn Gly Ile
                165                 170                 175

Pro Glu Asp Asn Lys Ser Ser Ser Ser Ala Asn Asp Ala Trp Arg Thr
            180                 185                 190

Trp Ser Leu Asp Lys Ser Arg Phe Ser Asp Phe Glu Ala Ala Glu Ile
        195                 200                 205

His Pro Leu Ser Arg Lys Pro Pro Lys His Val Asp Leu Asn Thr Val
    210                 215                 220

Leu Ile Glu Asp Asp Val Pro Gly Pro Ser Asn Gly Val Val Ile Asn
225                 230                 235                 240

Asp Tyr Pro Ser Asp His Val Asp Ser Glu Arg Asp Glu Ile His Ala
                245                 250                 255

Arg Phe Gln Asn Leu Glu Phe Asp Leu Ala Asp Ser Leu Lys Thr Leu
            260                 265                 270

Arg Ser Arg Phe Asp Gly Val Ser Ser Tyr Met Ser Asn Gly Glu Glu
        275                 280                 285

Ala Asp Val Val Asn Gly Phe Ser Asp Asp Trp Glu Phe Glu Glu Thr
    290                 295                 300

Lys Val Met His Ala Gln Glu Glu Leu Arg Thr Ile Arg Ala Lys Ile
305                 310                 315                 320

Ala Val Leu Glu Gly Lys Val Ala Leu Glu Ile Ile Glu Lys Asn Lys
                325                 330                 335

Ile Ile Glu Glu Lys Gln Thr Arg Leu Asp Glu Val Glu Lys Ala Leu
            340                 345                 350

Ser Glu Leu Arg Thr Val Ser Val Val Trp Pro Asn Pro Ala Ser Glu
        355                 360                 365

Val Leu Leu Thr Gly Ser Phe Asp Gly Trp Thr Ser Gln Arg Arg Met
```

370 375 380

Glu Gln Ser Glu Ser Gly Ile Phe Ser Tyr Asn Leu Arg Leu Tyr Pro
385 390 395 400

Gly Arg Tyr Glu Val Met Ala Cys Tyr Ser Ala Phe Ile Val Thr Ala
405 410 415

Phe Ser Ser Ser Asp Ser Gly Cys Trp Phe Val Leu Gln Ile Lys Phe
420 425 430

Ile Val Asp Gly Val Trp Lys Asn Asp Pro Leu Arg Pro Ser Val Asn
435 440 445

Asn His Gly Asn Glu Asn Asn Leu Met Ile Val Thr
450 455 460

<210> SEQ ID NO 55
<211> LENGTH: 10311
<212> TYPE: DNA
<213> ORGANISM: triticum aestivum
<220> FEATURE:
<221> NAME/KEY: modified_base
<222> LOCATION: (261)..(526)
<223> OTHER INFORMATION: a, c, g, or t
<220> FEATURE:
<221> NAME/KEY: modified_base
<222> LOCATION: (4111)..(4700)
<223> OTHER INFORMATION: a, c, g, or t

<400> SEQUENCE: 55
tcgatcaatc aaaaagcaaa gcttattaaa gcctgccctt ccgtggcccg gacgtcgatg 60
atctgtgggc agtggagcgc ggcgacggcg gccggcggcg gcggcagcgc atgatagcgt 120
ggcagtcaac taggccgaca taccacaccc atacgccgag gccaggcacg gcaacgggtc 180
acggggagct cgccgcgaca gggacgtgac gtgtgtggtg gtggacggcg ctcgcgtggt 240
tttttttttt tcccgtttgc nnnnnnnnnn nnnnnnnnnn nnnnnnnnnn nnnnnnnnnn 300
nnnnnnnnnn nnnnnnnnnn nnnnnnnnnn nnnnnnnnnn nnnnnnnnnn nnnnnnnnnn 360
nnnnnnnnnn nnnnnnnnnn nnnnnnnnnn nnnnnnnnnn nnnnnnnnnn nnnnnnnnnn 420
nnnnnnnnnn nnnnnnnnnn nnnnnnnnnn nnnnnnnnnn nnnnnnnnnn nnnnnnnnnn 480
nnnnnnnnnn nnnnnnnnnn nnnnnnnnnn nnnnnnnnnn nnnnnngcca ccgcgtcttc 540
gccgccaccg ccgacgggcc gcagccctgc cgcggccgcg tctgcgtctg cgccgcctac 600
atgcccccgc cgcggcagcc ctaccgccgg cccgcccccg ccccggcccc ggccccgcgc 660
ccgtccaatg cgcccgcgcc cgcgccgccg cagcgcggcc ctcgggacca ggaggagctc 720
gaggcggcga tctacgactt catgcgccgc tccgacaagc ccggcgcgtt ccccacccgc 780
gccgagctcc tcgccgcggg gcgcgccgac ctcgccgccg ccgtcgagtc cagcggaggc 840
tggctctccc tcggatggtc ctggtcctcc gacgacgacg cgcgacggcc ggctgcgtca 900
acggccggcc ccggcgtgca ccctgactac ccgcccgagg cgggtgcctc tggccgagcg 960
ccgaatgcga cggcggattc cgtaaggtgg gtaaccgagc cgctctgtaa tgtaatgcgc 1020
ccctctgttg attgctctgc gacgacttgc tgaattccga gtgttgcagg gagcagcagg 1080
aacccacgcc gtctgggagg cagccagaga cggaggagac acagtgggtg cctgctaaat 1140
ctctttggag ttattttgat gattgatatg ttggttcctt attgattttg cttgttgctc 1200
cttaatcgat tgcagggagg cagggtctgg ggcaggcctg gaggggatgc tcaccaggct 1260
gcggagagag agggagcgtg cgcggccacc gccacgcagc aagaatcgag cgggagggca 1320
aggtcaaaat ggcggtacgt gcattttcaa ctctcggcgt tctatcgaaa catatcttct 1380

```
ttgcaaacag ttatatgttt gttgataagg tttgcaacca atgaaacttt gcatagcaaa   1440
gagctcattg ttccatattg tttagttaca gcccgtggaa ggcttaagac tctgttggat   1500
aaaattaatg ctaagctcat gccgggcagg aaggaagtgc cgccgccgac aatagttcgt   1560
gcaaaagctg tctttctcac aggccggact tccctttccc ccgacatata taacttgcag   1620
tgcagtagtt tagcgctttc catttaaggt tgcaaagggg acaaacgtac cgttttttgt   1680
tctatgtcgc tttctaaaaa tagaagcgtg gcattagaac tttatttctc atgatccgac   1740
atattttttg tcgtcgtgct actgcttaat gtaaagttgt ttgcacctgg acagcactgc   1800
aattatttgt gtaattgtga atctacgtaa gactaccaca ttattttgtt tgtgcctttt   1860
aatcatagtg gtaatatgtt ctattacata caactggttt agctttgtta ttactctgcc   1920
catttcagca tttggtcctt ccaagctaat ggcctttttg tgttaaatct cttacaatac   1980
atggaggata attcattttc catttcaaat atgctctgtt aatagttgcc cctgaattga   2040
agggtccatg ctccctagat atacatggtt gattgaagtt agtagactgc gatttgcaaa   2100
tatatttact aattaaggac cgctttaaga ttgaccatgt gtttaggtat tttactgatt   2160
tagtgcacag ggatcatttt ctcggtactc tattagtatc aacagtaaaa agtacacatt   2220
gtgaactttt ggctggagac tcagagagga aaattgaaag agttccacct tatataatag   2280
aaaatagcat tggtttgtta ttgatggaat ggataatttt tgttagagag cttctgggta   2340
attatgtatg tgaaccttta ttctgatgta ccaaatactt aatttctagc tagtgtttct   2400
tcatttgtat attaataatc atacttctgt gttacataca tgcagcttta atgaaccata   2460
atggagctcc tagtcgaagt ccaactgatg gcatgtacac tcgaaggata cctgtgaatg   2520
gaaatataca tcgctctcat tctcaaaatg gaataccaga ggacaacaaa tcaagtagtt   2580
cagccaatga tgcatggcga acatggtctc ttgacaagag tcggttttct gattttgaag   2640
gttatatgat aacttaactt tcttttgttg cgcatcatat ctgttatgat tatttcataa   2700
catgtttaat atgctgacag ccgctgagat ccatcctttg agcagaaaac caccaaaacg   2760
tgctgacctg gacactgtgt tgatagaaga tgatgttccc ggaccatcta atggtgtggt   2820
tataaatgat tatcctagtg atcatgtaga ctctgaaaga gatgagatac atgcacgttt   2880
tcaaaatttg gaattcgatc ttgcagattc tcttaagaca ttaagatcaa gatttgatgg   2940
agtttcgtca tatatggtgt gtctcgtatc atcttcttta cttatctatc ttttgttgtg   3000
aaatactggt gggatacgtg atcttgagat tttagtgtgg ttttgcattc agtttcttc    3060
acttatgcat ttgtaaagtt gtttatgcat tgtactagac atggctctgc tgttccaaac   3120
aaaacacacc cgaagatatg gttctgcttg ctctaatttt ctctttatgc acttaacact   3180
gcctgcatca taccctcgcc catcactaga aaagtgccat cttgggatgc atgcagtcaa   3240
atttttgat tttgactaac actgtaacag tatcctcatc aatatgcagt ctgacatgaa    3300
aattgtacga gttcatttgc caacggaata acttccataa attttgattt tatatctgta   3360
gatattcact gtatatcccc tatcttttct tgcaatgttg tgatttcgca aggcaaacaa   3420
atgattatag ctaataatat tcccttgcag tgctgattgc tgaatgtagt tgtgttctct   3480
acgaggaagt agttggctag tcgcaatcta aaaagcacag atacggagac atggacacgt   3540
cgatacgcct acgggacacg ggatacggca ttttccaaaa acagccattc agggatacgg   3600
cgagtatata tggaaaaaat taaaacatgc catgtaatat agagttaaaa acaaaaaaaa   3660
tgaagagaaa ctgagataag atcagaatac tgccccattt ccatttgttg tattgttttt   3720
caagtgctta atgattgaat taattgatcc tctagaccca tgtcattgca acttgcaaaa   3780
```

tacatcaaat gctagtatta gtctgttaga gagtagagac tggagaagac atgcaacaaa 3840
ggatgcaggt gtaactttca ccctcaccca cggacgttgg ccaccggcgg tggtgctccc 3900
agacaccatg ctccctaacg tcaagcaaca atcaaaacag cagcaccagg caccagcatg 3960
caagtgagca gcagctcaag agcaagcagc aacggcatgg acgcatgggg aagcaagcag 4020
cagactcaac agcaagaaat cgagcaaaga tatgaagagg ttgaggctgc tggggttatc 4080
tgctcgagcg tggttgccat cgagtggttg nnnnnnnnnn nnnnnnnnnn nnnnnnnnnn 4140
nnnnnnnnnn nnnnnnnnnn nnnnnnnnnn nnnnnnnnnn nnnnnnnnnn nnnnnnnnnn 4200
nnnnnnnnnn nnnnnnnnnn nnnnnnnnnn nnnnnnnnnn nnnnnnnnnn nnnnnnnnnn 4260
nnnnnnnnnn nnnnnnnnnn nnnnnnnnnn nnnnnnnnnn nnnnnnnnnn nnnnnnnnnn 4320
nnnnnnnnnn nnnnnnnnnn nnnnnnnnnn nnnnnnnnnn nnnnnnnnnn nnnnnnnnnn 4380
nnnnnnnnnn nnnnnnnnnn nnnnnnnnnn nnnnnnnnnn nnnnnnnnnn nnnnnnnnnn 4440
nnnnnnnnnn nnnnnnnnnn nnnnnnnnnn nnnnnnnnnn nnnnnnnnnn nnnnnnnnnn 4500
nnnnnnnnnn nnnnnnnnnn nnnnnnnnnn nnnnnnnnnn nnnnnnnnnn nnnnnnnnnn 4560
nnnnnnnnnn nnnnnnnnnn nnnnnnnnnn nnnnnnnnnn nnnnnnnnnn nnnnnnnnnn 4620
nnnnnnnnnn nnnnnnnnnn nnnnnnnnnn nnnnnnnnnn nnnnnnnnnn nnnnnnnnnn 4680
nnnnnnnnnn nnnnnnnnnn tggagcagcg ttcctttagt ggcgaccgtg tgtgcgacct 4740
tgcaaaatag ggtttgtatc gggccgaggc tgttattgag cttcctgtgt ccccaacgta 4800
ttccatacgc atcccagctg tgtctttgtt tttttttcct ttttttaat taggaaatca 4860
ggggatactg ggggacacgc gtatcccagc atgtccggcc gcttcgccgt gtcccaccga 4920
attaggatgg caattcggca gttttggcca tttccatgct ttgtaggtcg caatgattta 4980
gtttgcaaat tattacacac tcttgttatt tagaaccatc gtattactgg taggaagttt 5040
ctgatcttcg agattcagcc gacgctgata tgaaactaaa atgataatgg aagatcttga 5100
tgcatctcat tttgattttt ctagaggtaa tatacttgtt ctgagcatcc atctttgccc 5160
ttccattttc cagtcaaatg gcgaagaagc agatgtggta aatgggttct ctgatgattg 5220
ggaatttgaa gagacaaaag taatgcatgc ccaggaagaa ttacggacaa tccgtgctaa 5280
aatagcagta ttagaaggca aggtggcgct cgaaataatg tatggtcact cacaattgaa 5340
tgttgatcat ctacgctttt tattttgtat caatctcttt tatgacttat tctgttgata 5400
tcagtgacaa gaacaaaata attgaagaaa agcaaacgag gcttgatgaa gttgagaagg 5460
ctttgagtga gctccgcaca gtatctgttg tatggcccaa tcctgcttca gaagttctat 5520
tgaccggttc ttttgatggg tggacaagcc aagtaagtgc atgttccgat tgtctgctta 5580
attaataaat atataaactt cactaactaa ctacaaaatg ggtggcagtt catgatttca 5640
atttctatca ccctttggtg ttagttgtca ggtgaattcc attgatttat gtattaagtt 5700
gaatactatt gaagagagaa gccggttcta ttgctgctct cctaagttgt gtaaatgcaa 5760
tttactgcca acatcttctc atgtgcacag ttaattcatt tattaatgag tgcaaaacaa 5820
gcacatataa attagatgca gcaagttaca tggaaacctc atcttaggga acatactccc 5880
tccgatccat attacagagg gagtacttag tttgatgtgg ttcacacaca agtaaagtaa 5940
cttcaggaac tagcaacatg gtagttacga gaatggtagg gatcaaggca ccaagtgctt 6000
tgaaagatgt ttattacgta tatgtttcta ggagtaaagc aagtttttaa tctgattttg 6060
gttgttggtg ctgtttttgg cataggcaca attgtgatga cacgtgtcca taacttttgt 6120

-continued

```
gttagaaata ctacgtgcta tttggatttg aaaggttaga aacattgttt tatatgccaa   6180
aagaaaaaag gaaaagcaca tggaatcttc ataaatttgt taatactcct tccgttcctt   6240
tttatgactt gtattggttt gttggaaagt caaacttttt tacctttgac caagtttata   6300
aaaagtcaat gtatgcaata ctaaatacat aaaatatgga aatatttttc atgaagggtc   6360
tgatgatact catttggcat tgtagatgtt gataattttt tctatataaa cttcgtcaaa   6420
gatagaaaag gtggacttaa aaaaacatct tataaaaagg gacggaggga gcatgtattt   6480
atcattctat attaagtgga aactgaagca gcacaatttt acaagagctc actaggcaag   6540
acctatcaac aaatatacta cctctgcaac tttttataag acatttttag agtctatgac   6600
aatgtgaaaa acgtgttata ttaagttacg gagggagtat gtctttatct ggtaccttta   6660
gctgagattt agtcagttcc taggaggata ctggtcacat gactgacata tccaaaaaga   6720
tgttcttcag ttcgagcaca tataggatag gtactagatg tagaagcctg aaggacaaca   6780
ttctgccatt atagatctta gtttcacttc catatgtatg gggtgctgt ttagttttgt    6840
catctatcta tatatcgttg tcgctatcgt cttattcttg agtataatca aacactggac   6900
tttttccttt tttgtagaga aggatggaac aatcagaagg aggcattttt tcgtataacc   6960
tgaggttgta tcctggtaga tatgaggtaa tggcgcgcta ttcttacttc actgtcactt   7020
ctttcacttc atctgatagt gggtgttggt ttgtgcttca gattaaattt attgttgatg   7080
gtgtttggaa gaacgacccg ctgcgcccta ctgtgaacaa caatgggaac gaaaacaacc   7140
ttatgattgt cacttgacct gcatccttgt agcaactgtg tagattatag attgtcatca   7200
acaatgattg gtgccaactg attagatatg ttctttcttc cttgtagctt atcagttttt   7260
gccgcctgtc atctcttgat tttcttttag agagccacgc gcgactttga acagtgtagg   7320
gtcagggtgt tgtcttcacc cccgctgaga tgggagaaga atatagctca atgtttgtgc   7380
gttctttcct ttcctctctt tcttctccct ggagaagcat agtggggcac tcaaatgccc   7440
cggtggcggt tgggggcagt tcgccgtcgg tgtcggtgtg ggtaacaatg tacatatctc   7500
gtgataggaa agttgtccat ggttagtttg tcaaggtggc ggcgtgcctg tcagtatgcg   7560
cgcactggtt cttactaaga tccaggccgg gaactcatct gatagaactc actcggcaga   7620
aggttagcag ctcatgcaca gatacaaaac acagtggaaa tgtgagcctc cattgggtca   7680
tcacagtaca gttgaaggca cattatgcct gaaaccaacc acaagtacag tgaaatagtt   7740
tatcttccat tttaacaact tacaagaaag aaattaacca ccccattgtt gtttctttca   7800
ttttcaacaa cttacaagaa attaaccacc ccattgttgt ctacagtaca tttcttcctc   7860
tctttccccg cccacttcat ctatagattg attgatttca taacagcaga accaaaaaat   7920
tataagaaca cagaagggaa atagctactg tggtatgtat aagacacgtg aattaatcac   7980
ctgaccttat tctacccct tcttccccat tgcatcaagc atctctggtc cccttgaacc    8040
tgtaccacct ggcgcagatc atgaagtaga caaagttgaa gacgccaatg ccggcgatca   8100
tccagtagaa gaggtcgagc ctgcccttgt tgaggtcctg cgccagccag ttctggccgg   8160
cccccgtggt ccggtgcacg atcgtcgtca ggaagccgct gaggtagttc cccagggcga   8220
ggttgcagaa ggcgagcgcg ccggcgacgc tcctcatgtg ctccgggatc tccttgtagt   8280
agaactcgat ctggctgatg aggttgaatg cctcggagag gccgaggatc atgagctgcg   8340
gcaccatcca gaagctggac atggcggaga tgccgccccc cgtctgcgtc gtgccgatgt   8400
tgggctggtt gagcgcgatg tccctgcgcc ggtcctcgac gacggcggag atgatcatgg   8460
cgacggtgga gagcgcgatc ccgatgccct ggcgctggag cagcgtgaag ccctcgtcct   8520
```

```
tgccggtgac cttgcggagg cgcggcacga ggagccggtc gtagatgggg atccagagcg   8580
tctgcgcgag catggcgaag acggtgaatg acgcggcggg gacgtggaag ctgctgccga   8640
ggcggcggtc ggactgcagc gcggagaaga cgacgtaggt ggactgctgc accacggcca   8700
cgtagtagat gatcccggtg gaccagacgg gcacgatgcg gatgaggcat ttcacctcct   8760
ccacctgctg cacggtgcag agccgccagg ggtcggccgc ggtggcgccg ccggggcgca   8820
cctcgtcctg ggacgccacc atggccgcct tgtcgaggca ccggaactgg tccgtgtgcg   8880
caagcttggt gacgatggcc gaggtgtgcg gcgggtcgaa caggtcctgc ttggggtcct   8940
tggcctgctt gagcgagcgc ttggcgaagg cggcggcgaa gacctgcacg atggtggtga   9000
agggggagcc ctcggggatg acgcgcacgt agaggcgcgt gcccatgaag aagagcacgc   9060
aggcgaggaa catgagcgcg gtggggatgc cgaggccgat ggcccagttg acgttgctct   9120
gcacgtagat gatgacggtg gcggagacga gcatggcgga ggtgaaggtg aagtagtacc   9180
agttgaagaa gctgttgatc ccgcgcttgc ccgactcggt gtgcgggtcg aactggtcgg   9240
cgccgaacgg catgctgcag ggccggatcc ccgcggagcc gatcaccagg aaggcgaagg   9300
cgatgaagag gacggcgagc tggtaggagg tggccttctc gcagacctcc cccacgccgc   9360
agtccgccgg gtgcaggctg tccgcgcccg ccgtcagcgt caggaagaac atgccctggg   9420
atgaacaggc aagcgttagt cagtgctgga gagaaacgaa cacaggcttt gtcaagaaga   9480
tcttgttagt tgctactccc tccgttccga aatataagtc gttgaactgg taatagttcg   9540
aagctgcgca acgttcagaa ttcacacggc cgtgtgcatc gattgatgca gaggcaggtg   9600
gtttttacct ccttttcgaa gaagaaaaaa tgattcaatc aagttattcc cagtttactg   9660
cactgcccca acactccctg cttcctcgcc tcgcctcgcc gtgcacacgc ggccgcccca   9720
ccccacccac ctcgccgcgc gcgcgcgggt ccggccggca gcatcctgtg cgcgtggtca   9780
ccaccaaatc cccgctccgg tccacggatc cagcggccac gcgcaccgcc gggggaacac   9840
gacacagcgc gcgcgctggc tgcaccccac tccccccgcc cgaactcgat ccccatcccc   9900
cgagtggctg tcgttgtcag tcaggcaggc ggagaagctt ccgcttccag cacagcagct   9960
cggcggagcc agcccaatgg cgatactatt ctcatgatcg agacaggggt gggtggccac  10020
tggccagcga tcgcggcgac tgacattgac gcggcaacgt ggggtgcttc cggttgggtg  10080
ctcctggaca aggcacggat cgctctcgtg gcaagagaga tgcgcgtgtc ctggagcgtg  10140
cggtgcgcgc cattttccca cggaaccgga cggacggccg gtggccgccg cgttgaggcg  10200
gtcaatgttg acatgccact ccggctggcc cgcagcgaag accgctcgtg gctgggtcgc  10260
gcaactagtt ggcagacaaa cgcatagtac acgtcctctg ccaaacaaaa c            10311
```

```
<210> SEQ ID NO 56
<211> LENGTH: 482
<212> TYPE: PRT
<213> ORGANISM: Triticum aestivum

<400> SEQUENCE: 56

Met Pro Pro Pro Arg Gln Pro Tyr Arg Arg Pro Ala Pro Ala Pro Ala
1               5                   10                  15

Pro Ala Pro Arg Pro Ser Asn Ala Pro Ala Pro Ala Pro Pro Gln Arg
            20                  25                  30

Gly Pro Arg Asp Gln Glu Glu Leu Glu Ala Ala Ile Tyr Asp Phe Met
        35                  40                  45

Arg Arg Ser Asp Lys Pro Gly Ala Phe Pro Thr Arg Ala Glu Leu Leu
```

```
    50                  55                  60

Ala Ala Gly Arg Ala Asp Leu Ala Ala Ala Val Glu Ser Ser Gly Gly
65                  70                  75                  80

Trp Leu Ser Leu Gly Trp Ser Trp Ser Ser Asp Asp Asp Ala Arg Arg
                85                  90                  95

Pro Ala Ala Ser Thr Ala Gly Pro Gly Val His Pro Asp Tyr Pro Pro
            100                 105                 110

Glu Ala Gly Ala Ser Gly Arg Ala Pro Asn Ala Thr Ala Asp Ser Val
        115                 120                 125

Arg Glu Gln Gln Glu Pro Thr Pro Ser Gly Arg Gln Pro Glu Thr Glu
    130                 135                 140

Glu Thr Gln Glu Ala Gly Ser Gly Ala Gly Leu Glu Gly Met Leu Thr
145                 150                 155                 160

Arg Leu Arg Arg Glu Arg Glu Arg Ala Arg Pro Pro Pro Arg Ser Lys
                165                 170                 175

Asn Arg Ala Gly Gly Gln Gly Gln Asn Gly Ala Leu Met Asn His Asn
            180                 185                 190

Gly Ala Pro Ser Arg Ser Pro Thr Asp Gly Met Tyr Thr Arg Arg Ile
        195                 200                 205

Pro Val Asn Gly Asn Ile His Arg Ser His Ser Gln Asn Gly Ile Pro
    210                 215                 220

Glu Asp Asn Lys Ser Ser Ser Ser Ala Asn Asp Ala Trp Arg Thr Trp
225                 230                 235                 240

Ser Leu Asp Lys Ser Arg Phe Ser Asp Phe Glu Ala Ala Glu Ile His
                245                 250                 255

Pro Leu Ser Arg Lys Pro Pro Lys Arg Ala Asp Leu Asp Thr Val Leu
            260                 265                 270

Ile Glu Asp Asp Val Pro Gly Pro Ser Asn Gly Val Val Ile Asn Asp
        275                 280                 285

Tyr Pro Ser Asp His Val Asp Ser Glu Arg Asp Glu Ile His Ala Arg
    290                 295                 300

Phe Gln Asn Leu Glu Phe Asp Leu Ala Asp Ser Leu Lys Thr Leu Arg
305                 310                 315                 320

Ser Arg Phe Asp Gly Val Ser Ser Tyr Met Ser Asn Gly Glu Glu Ala
                325                 330                 335

Asp Val Val Asn Gly Phe Ser Asp Asp Trp Glu Phe Glu Glu Thr Lys
            340                 345                 350

Val Met His Ala Gln Glu Glu Leu Arg Thr Ile Arg Ala Lys Ile Ala
        355                 360                 365

Val Leu Glu Gly Lys Val Ala Leu Glu Ile Ile Asp Lys Asn Lys Ile
    370                 375                 380

Ile Glu Glu Lys Gln Thr Arg Leu Asp Glu Val Glu Lys Ala Leu Ser
385                 390                 395                 400

Glu Leu Arg Thr Val Ser Val Val Trp Pro Asn Pro Ala Ser Glu Val
                405                 410                 415

Leu Leu Thr Gly Ser Phe Asp Gly Trp Thr Ser Gln Arg Arg Met Glu
            420                 425                 430

Gln Ser Glu Gly Gly Ile Phe Ser Tyr Asn Leu Arg Leu Tyr Pro Gly
        435                 440                 445

Arg Tyr Glu Ile Lys Phe Ile Val Asp Gly Val Trp Lys Asn Asp Pro
    450                 455                 460

Leu Arg Pro Thr Val Asn Asn Asn Gly Asn Glu Asn Asn Leu Met Ile
465                 470                 475                 480
```

Val Thr

<210> SEQ ID NO 57
<211> LENGTH: 7781
<212> TYPE: DNA
<213> ORGANISM: Triticum aestivum

<400> SEQUENCE: 57
atccaacggt tctaacgtag ttcgctggga aaacgtcccc ggctgccgtc ggccagttaa 60
gatttccctt cttttagctc tgcgtttagc aaatactccg tactagacaa aaaggtagag 120
ggaagttcac aagcagagcc gtcggccaga aaagcgcaaa acgcaccagg gttctcacac 180
gacacgcctc gacgtttcca tctttcgtca cgccgtgctt ccatccatcc atccgtcgat 240
caatcaaaaa gcaaagctta ttaaagtccg cccttccgtg gcccggacgt cgatgatctg 300
tgggcagcgg agcgcggcga cggcgaccgg cggcggcagc ggcagcgcag ggtaagcgtg 360
gcagtcgacc aggccgacat actacaccca tacgccgagg gccaggcgca ggcacggcaa 420
cgggtcacgg agagctcgcc gcgacaggga cgtgacgagc tggctctact ctactagtgg 480
tggtggacgg cgctggcgtc gctctatttt ttttcgtttt ccccctccct cctccgctct 540
ccggttccgg gaaagctccc gccctcgccg ctcggggagc ggcagagaaa tgcgacggcg 600 atgccccccct tcctcctctc gctgtccctc ccagccctaa ccctacccct gcctcccgcc 660
cccgcccccg cccctcgccg ccaccgcgtc ttcgcggcgc ccgcctacgg gccgcagccc 720
tgccgcggcc gcgtctgcgt ctgcgccgcc tacaggcccc cgccgcggca gccctaccgc 780
cgccagcccg ccccggcccc ggccccggac ccgcgcccgc gcccgtccaa tgcgcccgcg 840
ccgccgcagc gcgaccctcg gggccaggag gaggtcgagg aagcgatcta cgacttcatg 900
cgccgctccg acaagcccgg cgcgttcccc acccgcgccg agctcctcgc cgcggggcgc 960
gccgacctcg ccgccgccgt cgagtccagc ggaggctggc tctccctcgg atggtcctgg 1020
tcctccgacg acgacgcgcg gcggccggcc gcgtcgtcgg ccggccccgg cgtgcaccct 1080
gactacccgc ccgaggcggg tccttctggc cgaccgccaa actcggcggc ggattccgta 1140
aggtgggtaa ccgagccgct ctgtgatgtg taatgtaccc ctctgttgat tgctctgcga 1200
cgacttgctg aattccgagt gttgcaggga gcagcaggaa ccgacgcggt ctgggaggca 1260
gccggagacg gaggagacag agtgggtgcc tgctaaatct cttttgagtt attttgattg 1320
atatgttggt tccttattga ttttgcttct tgctccgtaa tcgattgcag ggaggcaggg 1380
tctggagcag gcctggaggg aatgctcgcc aggctgcgga gagagaggga gcgtgcgcgg 1440
ccaccgccac gcagcaagaa tcaagcggga gggcaaggtc aaaatggcgg tacgcgcatt 1500
ttcgattctc cgcgttctat cgaaacatgt gttgttttca gttgtgcagc atgagcatct 1560
tctttgcaaa cagttatatg tttgttgata aggtaacacc aacttttgca accaatggaa 1620
ctttgcatag catagagctc attgtgccat aatgtttagt tacagcccgt ggaaggtggc 1680
ttaacgctct gctggataaa attaatgcta agctcatgcc gggcaggaag gaagtgccgt 1740
tgacaatagt tcatgcaaaa gctgtctgtt ctcacggacc ggacttccct ttcccctgac 1800
atatataact agcagttcag tagtttagcg ctttccattt aaggttgcaa aggggacaaa 1860
cgtaccgttt tttgttctat gtcgcattct aaaaatagaa gtttggcatt agaactttat 1920
ttctcatgat ccgacatatt ttttgtcgtc gtgctactgc ttgatgtaaa gttgtttgca 1980
ccttgacagc actgcaatta tttgagtaat cgtgaatcta cggaagacta ccacattatt 2040

```
ttgtttgtgc cttttaatca tagtagtaat atgttctgtt acatacaact ggtttagctt   2100
tgttattact ctgcccattt cagcatttgg tccttccaag ctaatggccc ttttgtgtta   2160
aatctcttac aatacatgga gcataattca ttttccattt caaattgcct ctgttaatag   2220
ttgcccccta acacctaaat gaattgaagg gtccatgctc cctagatata catggttgat   2280
tgaagttagt agactctgcg atttgcaaat atatttacta attaaggacc gctttaagat   2340
tgaccatgtg tttaggtatt ttactgattt agtgcacacg gatcattttc tcggtactct   2400
attagtatca acagtaaaaa gtacacattg taaacttttg gctggagact cagagaggaa   2460
aattgaaaga gttccacctt atataattga aagagtagaa aatagtgttg gtttgttatt   2520
gatggacaac taatggataa tttttgttag agagcttctg gataattatg tatgtgaacc   2580
tttattctga tgtaccatat acttaatttc tagctggtgt ttcttcattt gtatattaat   2640
gatcatactt ctgtgttaca tacatgcagc tttaatgaac cataatggag ctcctagtcg   2700
aagtccaact gatggcatgt acactcgaag gatacctgtg aatggaaata tacatcgctc   2760
tcattctcaa aatggaatac cagaggccaa caaatcaagt agttcggcca atgatgcatg   2820
gcgaacatgg tctcttgaca agagtcggtt ttctgatttt gaaggttata tgataactta   2880
actttctttt gttgcacatc atatcttatg attatttcat aacatgttta atatgctgac   2940
agccgctgag atccatcctt tgagcagaaa accaccgaaa cgtgctgacc tggacactgt   3000
gttgatagaa gatgatgttc ccggaccatc taatggtgtg gttataaatg attatcctag   3060
tgatcatgta gactctgaaa gagatgagat acatgcacgt tttcaaaatt tggaattcga   3120
tcttgcagat tctcttaaga cattaagatc aagatttgat ggagtttcgt catatatggt   3180
gtgtctcgta tcatcttctt tacttatcta tcttttgttg tgaaatactg atgggatacg   3240
tgatcttgag attttagtgt ggttttgcat tcagttttct tcacttgtgc atttgtaaag   3300
ttgtttatgc attgtactag acatggctct gctgttccta acaaaacaca cccgaagata   3360
tggttctgct tgctctaatt ttctctttat gcacttaaca ctgcctgcat catacctcg    3420
cacatcacta gaaaagtgcc atcttgggat gcatgcagtc aaattttttg attttgacta   3480
acactgtaac agtatcctca tcaatatgca gtctgacaac atgaaaacgg tacaagttca   3540
tttgccaacg gaacaacttc cataaatttt gattttatat ctgtagatat tcactgtata   3600
tcccctatct tgtcttgcaa tgttgtgatt tcgcaacgca aacaaatgat tatcgctaat   3660
aatattccct tgcagtgctg attgctgaat gtagttgtgt tctctacgag gaagtagtta   3720
gctagtcgcg atataaaaag cacagatacg gagacatgga cacggcgata cgcctagggg   3780
acacgggata cggcattaaa cagccattca gggatacggc gagtatatat gaaaaaaatt   3840
aaaacatgcc atgtaatata gagttaaaaa aatgaagaga aactgagata agatcagaat   3900
actgccccat ttccatttgt tgtattgttt ttcaagtgtt caatgactga attaattgat   3960
cctctagacc catgtcattg caacttgcaa aatacatcaa atgctagtat tagtctatta   4020
gagagtagag actggagaag acatgcaaca aaggatgcag gtgtaacttt caccctcacc   4080
cacggacgat tagccaccgg cagtggcgct cccaaacgcc atgctcccta acatcaagca   4140
acaatcaaaa cagcagaacc aggcaccagc atgcaagtga gcagcagctc aagagcaagc   4200
agcaacggca tggacgcatg gggaagcaag cagcagactc aacagcaaga aatcgagcaa   4260
agatatgaag aggttgagaa gaggctgctg gggttatctg ctcgagcgtg gttgtcatcg   4320
ggcggttgag tccagggggc ggtggcgata gcgcgttcga cttggagcag cgttccttta   4380
gtggcaagcg tgtgtgcgac cttgcaaaat agggtttgta tcgggccgag gctgttattg   4440
```

```
agcttcctgt gtccccaacg tattccatac gtatcccagc tgtgtctttg tttttctcct   4500
ttctttaatt aggaaatcag gggatactgg gggacacgcg tatcccggca tgtccggcca   4560
tatcgccgtg tcgcaccgaa ttaggacggc aattcggcag tttcggccgt ttccatgctt   4620
tgttggtcgc aatgatttag tttgcaaatt attacacatt cttgtttttt agaaccattg   4680
tattactggt aggaagtttc tgattttcga gactcggccg acgctgatat gaaactaaaa   4740
cgataatgga agatcttgat gcatctcatc ttgacttttc tagaggcaat atacttgttc   4800
tgagcatcca tctttgccct tccattttcc agtcaaatgg cgaagaagca gatgtggtaa   4860
acgggttctc tgatgattgg gaatttgaag agacaaaagt aatgcatgcc caggaagaat   4920
tacggacaat ccgtgctaaa atagcagtat tagaaggcaa ggtggcgctt gaaataatgt   4980
atggtcactc acaattgaat gttgatcatc tacgcttttt attttgtatc aatctctttt   5040
atgacttatt ctgttgatat cagtgagaag aacaaaataa ttgaagaaaa gcaaacgagg   5100
cttgatgaag ttgagaaggc tttgagtgag ctccgcacag tatctgttgt atggcccaat   5160
cctgcttcag aagttctatt gaccggttct tttgatgggt ggacaagcca agtaagtcca   5220
tgtcccaatt ctctgcttaa ttaataaata tataaacttc accaagtaac tacaaaatgg   5280
gtggcagttc atgatttcaa tttctatcac tctttggtgt tagttgtcag gtgaattcca   5340
ttgatttatg tattaagttg aatattaatg aagagagaag ctggttctat tgctgctctc   5400
ctaagttgtg taaatgcaat ttactgccaa caccttatca tgtgcacagt taattcattt   5460
cttaatgagt gcaaaacaaa cacatacagc aagttatatg gaaacctgca tcttagggaa   5520
catactccct ccagtccata ttacagaggg ggtacttaat ttgatgtggt tcacacacaa   5580
gtaaagtaac ttcaggaact agcaacatgg tagttacgag aatggtaggg atcgaaggcg   5640
ccaagtgctt tgaaagatgt ttattacgta tatgtttcta ggagtaaagc aagtttgtaa   5700
tctgattttg gttgttggtg ctgtttttgg cataggcaca attgtgatga cacgtgtcca   5760
taacctttgt gttagaaata ctacgtgtta tttggatttg aaaggttaga aacattgttt   5820
tatatgccaa aagaaaaagg aaaagcacat ggaatcttca tatatttgtt aatactcctt   5880
ccattccttt ttatgacttg tattggtttg ttggaaagtc aagcttttct acctttgacc   5940
aagtttataa aaaaaaatca atgtatgaat actaaataca tacaatatgg aaatattttt   6000
catgaagggt ctgatgatac tgatttggta ttgtagatat tgatactttt ttctatataa   6060
acttggtcaa agatggaaaa ggtggacttt aaaaaaacat cttataaaaa ggaacggagg   6120
gagtatgtat ttatcatttt atattaagtg gaaactgaag cagcacaatt ttacaagagc   6180
ttcactaggc aagacctagc aacaaatata ctacctctgc aactttttat aagacatttt   6240
tagagtctat gacaatgtga aaaacgtttc atattaagtt agggagggag catatcttta   6300
tctggtacct ttagctgaga tttagtcagt tcctaggagg atactggtca catgactgac   6360
atatccaaaa agatgttctt cagttcgagc acatatagga taggtactag atgtagaagc   6420
ctgaaggaca acattctgcc attatagatc ttagtttcac ttccatatgt atgggggtgc   6480
tgtttagttt tattttgtat acatgatatt tgcatttcca tggagcacac agcacaattc   6540
agatcagcca gcagaagaat gttagtaata caaatcaaat ttggttctag agtaagaaat   6600
attacctgcg tcccaaatta cttgatctaa gacaagtaat tcgggacgga tggagtatga   6660
atttgttatg ccatttcacc tctcttgtcg ctcctttgat ataactttca agatattgaa   6720
taattaaaca tctaattgta tgaatgtcca tggaatgttg tctgctttgg gctgtgtact   6780
```

-continued

```
gcaggaagtc tctctgttaa tatatatagc tctgtgtttg cctgcttaat cacattctgt   6840

tccatgtcat gcctatgaca cgttttgtca tctatacatc gtcatcgcta tcgccttatt   6900

cttgagtata atcaaacact ggactatttt cctttttgta gagaaggatg gaacaatcag   6960

aaagcggcat tttttcgtat aacctgaggt tgtatcccgg tagatatgag gtaatggcgt   7020

gctactctgc ttccattgtc actactttca catcatctga tagtgggtgt tcgtttgtgc   7080

ttcagattaa atttattgtt gatggtgttt ggaagaacga cccgctgcgc cctaccgtga   7140

acaaccatgg gaacgaaaac aaccttatga ttgtcacttg acctgcctgc atccttgtag   7200

taactgtgta gattatagat tgtcatcaac aatgattggt gccaactgat tagatcgctt   7260

ctttcttcct tgtagcctgt cagtttttgc cgcctgtcgt ttcttgattg ttttctagag   7320

ccacgcatga cttggacagt gtagggtcag ggtgttgtct ttcaccccgc tgagatggga   7380

gaagaatata gctgttggtg tgtgtgttct ttccttcccc ctctttcttc tccctggaga   7440

agcatagcgg ggcactcgaa tgccccggtg gcggttgggg gtagttcgcc atcggtgtct   7500

cgggtgtgtg taacaatgta catatctggt gatagcaaag ttgtccgtgg ttagtttgtc   7560

aaggtggtgg cgtgcctgtc agtatgcacg cactggttct tactaagatc cagcccggga   7620

actcatctga tagaacagag catgtcaaat gcattggttg ggattggttg ggatagctat   7680

cggtcggcag aaggtcagca gctcaggcac aaatacaaaa cgcagtggag atgtgagcct   7740

ccattgggtc gtcacagtac agtttgaagg catgcatgcc t                       7781
```

<210> SEQ ID NO 58
<211> LENGTH: 559
<212> TYPE: PRT
<213> ORGANISM: Triticum aestivum

<400> SEQUENCE: 58

```
Met Pro Pro Phe Leu Leu Ser Leu Ser Leu Pro Ala Leu Thr Leu Pro
1               5                   10                  15

Leu Pro Pro Ala Pro Ala Pro Ala Pro Arg Arg His Arg Val Phe Ala
            20                  25                  30

Ala Pro Ala Tyr Gly Pro Gln Pro Cys Arg Gly Arg Val Cys Val Cys
        35                  40                  45

Ala Ala Tyr Arg Pro Pro Pro Arg Gln Pro Tyr Arg Arg Gln Pro Ala
    50                  55                  60

Pro Ala Pro Ala Pro Asp Pro Arg Pro Arg Pro Ser Asn Ala Pro Ala
65                  70                  75                  80

Pro Pro Gln Arg Asp Pro Arg Gly Gln Glu Glu Val Glu Glu Ala Ile
                85                  90                  95

Tyr Asp Phe Met Arg Arg Ser Asp Lys Pro Gly Ala Phe Pro Thr Arg
            100                 105                 110

Ala Glu Leu Leu Ala Ala Gly Arg Ala Asp Leu Ala Ala Ala Val Glu
        115                 120                 125

Ser Ser Gly Gly Trp Leu Ser Leu Gly Trp Ser Trp Ser Ser Asp Asp
    130                 135                 140

Asp Ala Arg Arg Pro Ala Ala Ser Ser Ala Gly Pro Gly Val His Pro
145                 150                 155                 160

Asp Tyr Pro Pro Glu Ala Gly Pro Ser Gly Arg Pro Pro Asn Ser Ala
                165                 170                 175

Ala Asp Ser Val Arg Glu Gln Gln Glu Pro Thr Arg Ser Gly Arg Gln
            180                 185                 190

Pro Glu Thr Glu Glu Thr Glu Glu Ala Gly Ser Gly Ala Gly Leu Glu
```

```
        195                 200                 205

Gly Met Leu Ala Arg Leu Arg Arg Glu Arg Glu Arg Ala Arg Pro Pro
    210                 215                 220

Pro Arg Ser Lys Asn Gln Ala Gly Gly Gln Gly Gln Asn Gly Ala Leu
225                 230                 235                 240

Met Asn His Asn Gly Ala Pro Ser Arg Ser Pro Thr Asp Gly Met Tyr
                245                 250                 255

Thr Arg Arg Ile Pro Val Asn Gly Asn Ile His Arg Ser His Ser Gln
            260                 265                 270

Asn Gly Ile Pro Glu Ala Asn Lys Ser Ser Ser Ser Ala Asn Asp Ala
        275                 280                 285

Trp Arg Thr Trp Ser Leu Asp Lys Ser Arg Phe Ser Asp Phe Glu Ala
    290                 295                 300

Ala Glu Ile His Pro Leu Ser Arg Lys Pro Pro Lys Arg Ala Asp Leu
305                 310                 315                 320

Asp Thr Val Leu Ile Glu Asp Asp Val Pro Gly Pro Ser Asn Gly Val
                325                 330                 335

Val Ile Asn Asp Tyr Pro Ser Asp His Val Asp Ser Glu Arg Asp Glu
            340                 345                 350

Ile His Ala Arg Phe Gln Asn Leu Glu Phe Asp Leu Ala Asp Ser Leu
        355                 360                 365

Lys Thr Leu Arg Ser Arg Phe Asp Gly Val Ser Ser Tyr Met Ser Asn
    370                 375                 380

Gly Glu Glu Ala Asp Val Val Asn Gly Phe Ser Asp Asp Trp Glu Phe
385                 390                 395                 400

Glu Glu Thr Lys Val Met His Ala Gln Glu Glu Leu Arg Thr Ile Arg
                405                 410                 415

Ala Lys Ile Ala Val Leu Glu Gly Lys Val Ala Leu Glu Ile Ile Glu
            420                 425                 430

Lys Asn Lys Ile Ile Glu Glu Lys Gln Thr Arg Leu Asp Glu Val Glu
        435                 440                 445

Lys Ala Leu Ser Glu Leu Arg Thr Val Ser Val Val Trp Pro Asn Pro
    450                 455                 460

Ala Ser Glu Val Leu Leu Thr Gly Ser Phe Asp Gly Trp Thr Ser Gln
465                 470                 475                 480

Arg Arg Met Glu Gln Ser Glu Ser Gly Ile Phe Ser Tyr Asn Leu Arg
                485                 490                 495

Leu Tyr Pro Gly Arg Tyr Glu Val Met Ala Cys Tyr Ser Ala Ser Ile
            500                 505                 510

Val Thr Thr Phe Thr Ser Ser Asp Ser Gly Cys Ser Phe Val Leu Gln
        515                 520                 525

Ile Lys Phe Ile Val Asp Gly Val Trp Lys Asn Asp Pro Leu Arg Pro
    530                 535                 540

Thr Val Asn Asn His Gly Asn Glu Asn Asn Leu Met Ile Val Thr
545                 550                 555


<210> SEQ ID NO 59
<211> LENGTH: 531
<212> TYPE: PRT
<213> ORGANISM: Hordeum vulgare

<400> SEQUENCE: 59

Met Pro Pro Phe Leu Leu Pro Ser Leu Leu Leu Pro Ala Leu Thr Leu
1               5                   10                  15
```

-continued

```
Pro Leu Pro His Ala Pro Ala Arg Arg Arg His Arg Val Phe Ala Ala
            20                  25                  30

Pro Pro Ala Ala His Ser Cys Gly Arg Arg Val Cys Ala Ala His Arg
        35                  40                  45

Pro Pro Pro Arg Gln Pro Tyr Arg Arg Arg Pro Ala Pro Ala Gln Val
    50                  55                  60

Pro Arg Ser Ser Gln Ser Asn Ala Pro Pro Pro Pro Pro Gln Gln Gly
65                  70                  75                  80

Gly Pro Arg Gly Gln Glu Glu Leu Glu Ala Ala Ile Tyr Asp Phe Met
                85                  90                  95

Arg Arg Ser Asp Lys Pro Gly Ala Phe Pro Thr Arg Ala Glu Leu Leu
            100                 105                 110

Ala Gly Arg Asn Asp Leu Ala Ala Ala Val Glu Ser Ser Gly Gly Trp
        115                 120                 125

Leu Ser Leu Gly Trp Ser Trp Ser Ser Ser Asp Asp Gly Asp Ala Arg
    130                 135                 140

Arg Pro Ala Ala Ser Ser Ala Gly Pro Gly Ala His Pro Asp Tyr Pro
145                 150                 155                 160

Pro Glu Ala Gly Pro Ser Gly Arg Ala Pro Asn Ala Ser Ala Asp Ser
                165                 170                 175

Val Arg Glu Gln Gln Glu Pro Thr Pro Ser Gly Arg Gln Pro Val Thr
            180                 185                 190

Glu Glu Thr Ala Glu Ala Gly Ser Gly Ala Gly Leu Glu Gly Met Leu
        195                 200                 205

Thr Arg Leu Arg Arg Glu Arg Glu Arg Ala Arg Pro Pro Pro His Ser
    210                 215                 220

Lys Asn Gln Ala Gly Arg Gln Gly Gln Asn Gly Ala Leu Met Asn His
225                 230                 235                 240

Asn Gly Ala Pro Gly Arg Ser Pro Thr Asp Gly Ile Tyr Thr Arg Arg
                245                 250                 255

Val Pro Asp Asn Gly Asn Ile Arg Ser Ser Tyr Ser Gln Asn Gly Ile
            260                 265                 270

Leu Glu Asp Asn Lys Pro Ser Thr Ser Ala Lys Asp Ala Trp Arg Thr
        275                 280                 285

Trp Ser Leu Asp Asn Ser Arg Phe Ser Asp Phe Gln Ala Ala Glu Ile
    290                 295                 300

Asp Pro Trp Ser Arg Glu Leu Pro Lys Arg Val Asp Leu Asp Thr Val
305                 310                 315                 320

Leu Met Gln Asp Asp Val Pro Gly Pro Ser Asn Gly Val Ala Ile Asn
                325                 330                 335

Gly Tyr Ser Ser Asp His Val Asp Ser Gly Arg Asp Glu Ile His Ala
            340                 345                 350

Arg Leu Gln Asn Leu Glu Leu Asp Leu Thr Asp Ala Leu Lys Thr Leu
        355                 360                 365

Lys Ser Arg Phe Asp Gly Val Ser Leu Asp Met Ser Asn Gly Glu Thr
    370                 375                 380

Ala Asp Val Val Asn Gly Leu Ser Asp Asp Trp Glu Phe Glu Glu Thr
385                 390                 395                 400

Lys Val Met His Ala Gln Glu Glu Leu Arg Ser Ile Arg Ala Lys Ile
                405                 410                 415

Ala Val Leu Glu Gly Lys Met Ala Leu Glu Ile Ile Glu Lys Asn Arg
            420                 425                 430

Val Ile Glu Glu Lys Gln Thr Arg Leu Asp Glu Val Glu Lys Ala Leu
```

```
        435                 440                 445

Ser Glu Leu Arg Thr Val Tyr Ile Val Trp Ser Asn Pro Ala Ser Glu
    450                 455                 460

Val Leu Leu Thr Gly Ser Phe Asp Gly Trp Thr Ser Gln Arg Arg Met
465                 470                 475                 480

Glu Lys Ser Glu Arg Gly Ile Phe Ser Leu Asn Leu Arg Leu Tyr Pro
                485                 490                 495

Gly Arg Tyr Glu Ile Lys Phe Ile Val Asp Gly Val Trp Lys Asn Asp
            500                 505                 510

Pro Leu Arg Pro Thr Val Asn Asn His Gly Asn Glu Asn Asn Leu Val
        515                 520                 525

Ile Val Thr
    530


<210> SEQ ID NO 60
<211> LENGTH: 529
<212> TYPE: PRT
<213> ORGANISM: Oryza sativa

<400> SEQUENCE: 60

Met Leu Pro Leu Leu Leu Pro Leu Pro Val Thr Pro Pro Pro Pro Leu
1               5                   10                  15

Pro Ser Pro Thr Leu Thr Leu Ala Pro Ala Ser Ala Pro Arg Arg Arg
            20                  25                  30

Leu Val Leu Leu Ala Ala Ala Ala Pro His His His His His His Arg
        35                  40                  45

Arg Arg Arg Val Tyr Arg Arg Gln Arg Ala Ala Pro Thr Gln Thr Arg
    50                  55                  60

Ala Pro Arg Arg Thr Leu Ser Ala Ser Asn Ala Ala Arg Gly Glu Glu
65                  70                  75                  80

Asp Leu Glu Glu Ala Ile Tyr Glu Phe Met Arg Arg Ser Asp Lys Pro
                85                  90                  95

Gly Ala Phe Pro Thr Arg Ala Glu Leu Val Ala Ala Gly Arg Ala Asp
            100                 105                 110

Leu Ala Ala Ala Val Asp Ala Cys Gly Gly Trp Leu Ser Leu Gly Trp
        115                 120                 125

Ser Ser Gly Gly Ala Glu Ala Gly Arg Ala Ser Ser Ser Val Gly Val
    130                 135                 140

His Pro Asp Tyr Pro Pro Glu Ala Gly Ala Ala Ala Ala Ala Gly Gly
145                 150                 155                 160

Ala Ser Asp Leu Ala Gln Gly Ala Val Trp Ala Ser Ser Arg Glu Ala
                165                 170                 175

Glu Ala Ser Pro Ser Gly Arg Gln Pro Glu Thr Glu Glu Glu Glu Thr
            180                 185                 190

Glu Thr Lys Phe Gly Thr Gly Leu Asp Gly Met Leu Thr Arg Leu Gln
        195                 200                 205

Arg Glu Arg Glu Arg Val Arg Pro Pro Leu Pro Arg Ser Ser Asp Gly
    210                 215                 220

Ala Gly Gly Glu Arg Asp Asn Val Ala Leu Met Gly Gln Ser Gly Ala
225                 230                 235                 240

Pro Ser His Ser Ala Thr Gly Gly Arg Tyr Thr Pro Lys Val Pro Asp
                245                 250                 255

Asn Gly Asn Ile His Ser Tyr His Pro Gln Asn Gly Ala Leu Glu His
            260                 265                 270
```

-continued

```
Asn Lys Ser Ser Lys Ser Leu Thr Asn Asp Ala Trp Arg Thr Trp Ser
        275                 280                 285

Leu Asp Lys Gly Gly Phe Ser Asp Phe Gln Ala Ala Glu Ile His Ser
    290                 295                 300

Thr Asn Ser Arg Lys Ser Phe Arg His Asp Gly Leu Asp Ile Leu Ala
305                 310                 315                 320

Gln Asp Asp Val His Gly Pro Ser Asn Gly Val Ala Val His Asp Tyr
                325                 330                 335

Asp Ile Asn Asp Val Asp Ser Glu Arg Asp Asp Ile His Ala Arg Leu
            340                 345                 350

Gln Asn Leu Glu Leu Asp Leu Thr Ala Ala Leu His Thr Leu Arg Ser
        355                 360                 365

Arg Phe Asp Lys Val Ile Ser Asp Met Ser Glu Gly Asp Gly Ala Lys
    370                 375                 380

Ala Pro Asn Gly Leu Ser Asp Asp Trp Glu Phe Glu Glu Thr Lys Val
385                 390                 395                 400

Met Gln Ala Gln Glu Glu Leu Arg Ser Ile Arg Ala Lys Ile Ala Val
                405                 410                 415

Leu Glu Gly Lys Met Ala Leu Glu Ile Ile Glu Lys Asn Lys Ile Ile
            420                 425                 430

Glu Glu Lys Gln Arg Arg Leu Asp Glu Ala Glu Lys Ala Leu Ser Glu
        435                 440                 445

Leu Arg Thr Val Tyr Ile Val Trp Ser Asn Pro Ala Ser Glu Val Leu
    450                 455                 460

Leu Thr Gly Ser Phe Asp Gly Trp Thr Ser Gln Arg Arg Met Glu Arg
465                 470                 475                 480

Ser Glu Arg Gly Thr Phe Ser Leu Asn Leu Arg Leu Tyr Pro Gly Arg
                485                 490                 495

Tyr Glu Ile Lys Phe Ile Val Asp Gly Val Trp Arg Asn Asp Pro Leu
            500                 505                 510

Arg Pro Leu Val Ser Asn Asn Gly His Glu Asn Asn Leu Leu Thr Val
        515                 520                 525

Thr


<210> SEQ ID NO 61
<211> LENGTH: 532
<212> TYPE: PRT
<213> ORGANISM: Arabidopsis thaliana

<400> SEQUENCE: 61

Met Val Ser Ile Asn Ser Gly Pro Ile Ser Ser Phe Val Ser Arg Tyr
1               5                   10                  15

Ser Met Ile Asp Ser Asp Thr Leu Leu His Leu Ser Ser Phe Gly Ser
            20                  25                  30

Thr Phe Asn Pro Asn Tyr Lys Ala Lys Ala Cys Ile Arg Phe Ala Arg
        35                  40                  45

Lys Val Cys Gly Ser Thr Val Leu Gly Phe Leu Glu Val Lys Pro Arg
    50                  55                  60

Lys Lys Ser Cys Cys Ser Arg Cys Asn Gly Val Ser Arg Met Cys Asn
65                  70                  75                  80

Lys Arg Asn Leu Gly Trp Asp Ser Glu Gly Ser Lys Asp Leu Glu Thr
                85                  90                  95

Glu Ile Leu Glu Phe Met Lys Asn Ser Glu Lys Pro Gly Met Phe Pro
            100                 105                 110
```

```
Ser Lys Lys Asp Leu Ile Arg Ser Gly Arg Phe Asp Leu Val Glu Arg
        115                 120                 125

Ile Val Asn Gln Gly Gly Trp Leu Ser Met Gly Trp Asp Leu Asp Glu
    130                 135                 140

Gln Glu Glu Lys Val Arg Val Asn Glu Asn Val Thr Pro Gln Asp Leu
145                 150                 155                 160

His Ile Glu Lys Gln Leu Pro Asn Cys Asn Ser Pro Glu Met Asp Lys
                165                 170                 175

Thr Leu Asn His Gly Asp Leu Asp Leu Ser Ser Asn Leu Ser Ser Ser
            180                 185                 190

Thr Glu Gln Val Glu Ser Arg Asn Asp Ser Gly Ile Glu Gly Ile Leu
        195                 200                 205

Thr Arg Leu Glu Lys Glu Arg Asn Leu Ser Leu Gly Ile Ser Val Arg
    210                 215                 220

Glu Asn Gly Lys Ser Asn Gly Ala Met His Asp Ile Ser Pro Asn Gly
225                 230                 235                 240

Ser Val Pro Trp Ser Ser Arg Ile Val Thr Ala Ser Glu Ile Gln Glu
                245                 250                 255

Val Asp Gly Ser Arg Gly Ser Gly Glu Tyr Ala Gln Ser Arg Tyr Gln
            260                 265                 270

Gly Ala Lys Ser Val Ser Gly Lys Pro Gly Leu Ser Asp Ser Pro Thr
        275                 280                 285

Ser Glu Thr Trp Arg Thr Trp Ser Met Arg Arg Ala Gly Phe Thr Asp
    290                 295                 300

Glu Asp Phe Glu Ala Ala Glu Ile Ser Ser Ser Gly Leu Thr Gly Val
305                 310                 315                 320

Lys Lys Asp Asp Thr Lys Lys Asp Ser Gly Asp Ser Met Asn Gly Lys
                325                 330                 335

Asp Arg Ile Ala Ser Ser Ser Glu Asp Val Asn Lys Thr His Ile Lys
            340                 345                 350

His Arg Leu Gln Gln Leu Gln Ser Glu Leu Ser Ser Val Leu His Ser
        355                 360                 365

Leu Arg Ser Pro Pro Asp Lys Val Val Thr Ser Lys Asp Ser Glu Thr
    370                 375                 380

Thr Ala Gly Asn Leu Glu Asn Leu Ser Asp Asp Trp Glu Tyr Lys Glu
385                 390                 395                 400

Asn Glu Ile Ile His Ala Gln Asn Lys Leu Arg Ser Thr Arg Ala Lys
                405                 410                 415

Leu Ala Val Leu Glu Gly Lys Met Ala Met Ala Ile Ile Asp Ala Gln
            420                 425                 430

Arg Ile Val Arg Glu Lys Gln Arg Arg Ile Asp His Ala Ser Arg Ala
        435                 440                 445

Leu Arg Leu Leu Arg Thr Ala Ser Ile Val Trp Pro Asn Ser Ala Ser
    450                 455                 460

Glu Val Leu Leu Thr Gly Ser Phe Asp Gly Trp Ser Thr Gln Arg Lys
465                 470                 475                 480

Met Lys Lys Ala Glu Asn Gly Val Phe Ser Leu Ser Leu Lys Leu Tyr
                485                 490                 495

Pro Gly Lys Tyr Glu Ile Lys Phe Ile Val Asp Gly Gln Trp Lys Val
            500                 505                 510

Asp Pro Leu Arg Pro Ile Val Thr Ser Gly Gly Tyr Glu Asn Asn Leu
        515                 520                 525

Leu Ile Ile Ser
```

530

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 62
gaaggtcgga gtcaacggat t 21

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 63
gaaggtgacc aagttcatgc t 21

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 64
tcgtcgccat ggaggagg 18

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 65
tcgtcgccat ggaggaga 18

<210> SEQ ID NO 66
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 66
aggaccaaag accgggcg 18

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 67
acagtctcct aggcgtctgc 20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 68
acagtctcct aggcgtctga 20

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 69
ctaccagcag gagaatagga tc 22

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 70
agttgataca ggtgcagttt a 21

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 71
agttgataca ggtgcaggtt c 21

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 72
ccatctattt ggcggcaa 18

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 73
gggagattgt ggttatctgg aac 23

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
gggagattgt ggttatctgg aat 23

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
cagctgactt caattcattt agc 23

<210> SEQ ID NO 76
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
ggagattgtg gttatctgga ac 22

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
ggagattgtg gttatctgga at 22

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
ctgacttcaa ttcatttagc actg 24

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
tccgaggttc cagagcacgg 20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 80
tccgaggttc cagagcacga 20

<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 81
tgctgtcaag atgattgtat ggag 24

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 82
gcagactcaa acaacttgct c 21

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 83
gcagactcaa acagcttgct t 21

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 84
cagctttctg aacttgagag g 21

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 85
atgttgccgt tgtagtggac 20

<210> SEQ ID NO 86

<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 86
atgttgccgt tgtagtggat 20

<210> SEQ ID NO 87
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 87
agcacgcgga gatcgaca 18

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 88
cttcaaataa atgggggcac 20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 89
cttcaaataa atgggggcaa 20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 90
cccagtggat gagaattttc 20

<210> SEQ ID NO 91
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 91
gcatgtcttt aagatataca taaataaata aac 33

<210> SEQ ID NO 92
<211> LENGTH: 29

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 92
gcatgtcttt aagatataca taaataaac 29

<210> SEQ ID NO 93
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 93
aagtaagatg cctttctgaa gttct 25

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 94
atttggcatg cggaatggct c 21

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 95
atttggcatg cggaatggct a 21

<210> SEQ ID NO 96
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 96
ttcattcata cttgataatg ccc 23

<210> SEQ ID NO 97
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 97
gaaatcattc gcccctgac 19

<210> SEQ ID NO 98
<211> LENGTH: 19
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 98
gaaatcattc gcccctgaa 19

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 99
gagctgcaga tttgttcctg 20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 100
taggcccagc actggtcaac 20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 101
taggcccagc actggtcaaa 20

<210> SEQ ID NO 102
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 102
ttacctgaga tgtttgatga ca 22

<210> SEQ ID NO 103
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 103
caagtacggc ctcccgaa 18

<210> SEQ ID NO 104
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 104
caagtacggc ctccccag 18

<210> SEQ ID NO 105
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 105
ggtgtaggag ctgaccgag 19

<210> SEQ ID NO 106
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 106
gccttgcgcg cgaggacc 18

<210> SEQ ID NO 107
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 107
gccttgcgcg cgagcacg 18

<210> SEQ ID NO 108
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 108
aagaactcgg agaagcg 17

<210> SEQ ID NO 109
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 109
ctggtgtact atggtctgat cg 22

<210> SEQ ID NO 110
<211> LENGTH: 22
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 110
ctggtgtacg atggtctgat ca 22

<210> SEQ ID NO 111
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 111
tagcttgtgt ggttcatgtt aat 23

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 112
gcatttgagg tggaggtctg 20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 113
gcatttgagg tgaaggtcta 20

<210> SEQ ID NO 114
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 114
ccagagaagc aagtgaccg 19

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 115
aggatggaac aatcagaagg c 21

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic -continued

```
      primer

<400> SEQUENCE: 116

aggatggaac aatcagaagg a                                              21


<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117

ctaccgggat acaacctcag                                                20
```

PLANT GENE FOR GRANULE DEVELOPMENT, MODIFIED CEREAL PLANTS AND GRAIN

SEQUENCE LISTING

The instant application contains a Sequence Listing which has been filed electronically in ASCII format and is hereby incorporated by reference in its entirety. Said ASCII copy, created on Oct. 29, 2018, is named 146836_00101_SL.txt and is 140,184 bytes in size.

TECHNICAL FIELD

The present invention relates to a genetic construct able to affect the development of B-type starch granules in plants of the Triticeae and Aveneae tribes, to domesticated plants of the Triticeae and Aveneae tribes in which B-type starch granules (i.e. small starch granules) are substantially absent from the grain endosperm, and to grain harvested therefrom and its use as flour or otherwise.

BACKGROUND ART

Plants of the Triticeae and Aveneae tribes include economically important cereals such as wheat, barley, rye and oats which produce grain having a starch-containing endosperm. The starch of such cereals is widely used in the food & drink industry as well as finding multiple non-food industrial applications. The starch produced by different species can vary in physical properties (such as gelatinisation profile, gel and paste properties and ease of hydrolysis) which can impact its commercial application and value. Whilst it is common for starches to be processed (e.g. chemically, enzymatically or physically) in order to modify their properties to be more suited to the intended use, such modification adds cost to the final product.

During development of the grain, starch becomes deposited in the endosperm as a semi-crystalline aggregate, termed a starch granule. Most Triticeae species have a bimodal starch granule morphology with both large lenticular A-type granules and smaller, spherical B-type granules present, and domesticated wheat and barley show very little variation in starch granule-size distribution between cultivars. Aveneae (oats), which is a tribe closely related to the Triticeae, also has B-type starch granules but instead of A-type starch granules they accumulate compound starch granules (Saccomanno et al., 2017, Journal of Cereal Science 76: 46-54).

Depending upon the intended end-use of the starch, the presence of a specific granule type can be disadvantageous or beneficial. For example, B-type granules are thought to be able to bind more water than the A-type particles leading to a greater hydration of the product. In some starch purification processes the B-type granules precipitate with proteins leading to their removal in the waste stream, thus decreasing yield and also causing the waste-stream processing to be more complex and costly. In the conversion of starch to sugars, B-type granules may degrade less readily than A-type granules resulting in a loss of potential product. An example would be in the mashing process of beer production (see Bathgate et al., 1974, In: European Brewery Convention, The Proceedings of the $14^{th}$ Congress, Salzburg; Elsevier Scientific Publishing, pages 183-196) where the presence of B-type granules can also cause a "starch haze" that leads to filtration problems. B-type granules have been reported to adversely affect flour processing and bread-making quality (see Park et al., 2009, Journal of Cereal Science 49:98-105), whilst their presence is reported to be beneficial for pasta-making (see Soh et al., 2006, Cereal Chemistry 83:513-519). The presence of B-type granules also has an effect on non-food industrial starch processes.

Although much effort has been expended to understand the synthesis of starch polymers in plants, the initiation of starch granule formation is still poorly understood. Stoddard and Sarker (2000, Cereal Chemistry, 77:445) screened 200 hexaploid wheat and 99 *Aegilops* accessions for variation in granule-size distribution and found that all hexaploid wheat and most *Aegilops* species had both A- and B-type granules. Five *Aegilops* species were identified that had A-type granules only and lacked B-type granules. Howard et al., 2011 (Journal of Experimental Botany 62(6)-2217-2228) describes using Bulked Segregant Analysis and QTL mapping to identify a major QTL for B-type granules on the short arm of chromosome 4S in *Aegilops* (Goat Grass). Briefly, Howard et al., crossed *Aegilops peregrina* (aka *Aegilops variabilis*), which naturally lacks B-type granules, with a synthetic tetraploid *Aegilops* KU37, which has both A-type and B-type granules within its endosperm, to produce a population segregating for B-type granule number. However, whilst Howard et al. report a QTL for B-type starch located on chromosome 4SS, the identity of the gene or genes responsible was not determined.

CN103554238 describes a starch synthesis related protein Flo6 in rice plants and a coding gene thereof. Rice plants containing a mutation in the gene produced grain with a loose arrangement of starch granules giving a "silty" or "floury" phenotype. In rice and barley (Franubet), mutations disabling the Flo6 gene cause disruption of starch granule structure (Suh et al., Carbohydrate Polymers 56: 85-93 (2004); Peng et al., Plant J. 77: 917-930 (2014)).

THE INVENTION

The present invention provides methods to produce cereal with modified levels of small granule types (such as B granules) within the endosperm. The term "modified" means that the level (number, weight or volume) of such small granule types (i.e. B-granules) can be decreased (relative to the normal level of that granule type within that cereal) or can be increased (relative to the normal level of that granule type within that cereal).

The present invention further provides methods to decrease the level of small granule types (e.g. B-type granules) in the grains of domesticated Triticeae species by genetic means. These means include crossing of domesticated Triticeae species with B-less plants generated by this invention (or their progeny) and/or by genetic manipulation of the gene responsible for B-type granule formation. Molecular markers can be used to enhance the efficiency of selection.

The present invention further provides methods to increase the level of small granules types (e.g. B-type granules) in the grains of domesticated Triticeae species by genetic means.

The present invention provides the genetic sequence of the gene responsible for B-granule production in wheat, and thereby provides a methods of manipulating B-granule content in wheat grain, in particular a method of reducing B-granule content or a method of increasing B-granule content.

BRIEF DESCRIPTION OF THE DRAWINGS

FIG. 3A shows: a schematic representation of the location of the QTL reported by Howard et al., and FIG. 3B shows: a graph showing the size and position of the QTL responsible for variation in B-granule number. Data in FIG. 3A and FIG. 3B were calculated using genotype data for linked markers together with granule-size phenotype for 84 $F_2$ plants of *Aegilops*. The QTL explains 44.4% of the variation in granule size distribution

FIG. 8A. A diagram of the genetic map derived from the *A. peregrina* x KU37 cross (FIG. 2). Genes with the same genetic location are boxed.

FIG. 8B. Physical maps of chromosomes 4A, 4B and 4D of *T. aestivum* cv Chinese Spring (Refseqv1, IWGSC). Genes and their orientations are indicated by arrows. Positions in by are indicated.

FIG. 10 shows alignment of FLO6 proteins. All protein sequences are orthologs of Rice FLO6 (Os03g0686900) from Ensembi plant (plants.ensembl.org) and were aligned using ClustalW (with manual fine adjustment).

FIG. 11A. Starch from TILLING mutant lines with mutations in the A-genome (aaBB) or the B-genome (AAbb) was compared with that from wild-type Kronos (AABB).

FIG. 11B. Starch from the progeny of a cross between two TILLING mutant lines (K2244×K3239) was compared with that from the single mutant parent lines and wild-type Kronos (AABB).

FIG. 11C. Shows a reduction in small-granule content similar to that seen for the Paragon AD double mutant and in *Aegilops peregrina.*

DETAILED DESCRIPTION OF THE INVENTION

Work performed by the present inventors and described for the first time within this application identified a gene as responsible for B-granule initiation in domesticated Triticeae species which was designated "Bgc-1 QTL marker gene" or "Bgc-1" and as given in SEQ ID No. 4. However, further work has demonstrated, that this gene is not in fact the gene responsible for B-granule formation in wheat. Significant further work has been required to identify the gene responsible.

Figure 1:
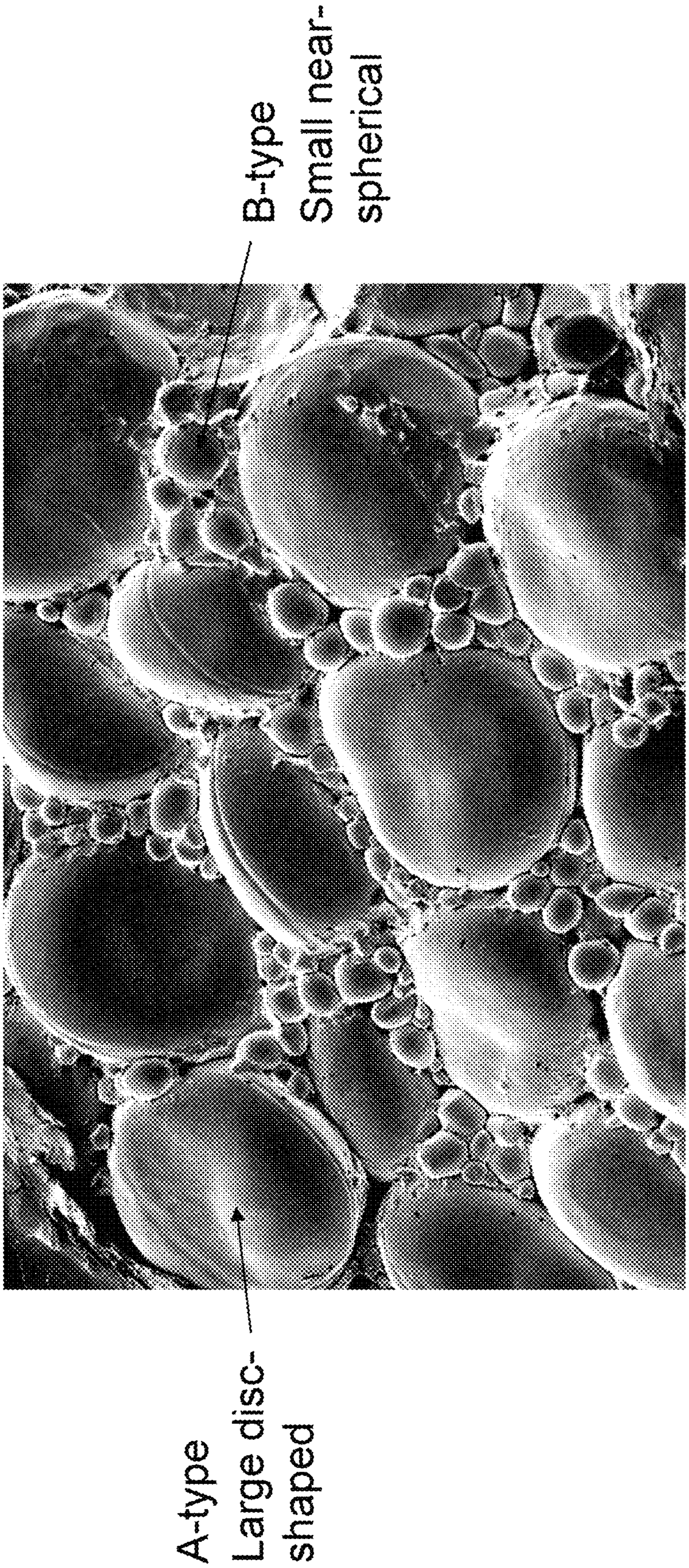
FIG. 1 is a scanning electron micrograph showing the two different starch granule types present in domesticated Triticeae, here wheat. Similar types of granules are also found in barley, rye and wild wheats.
Figure 2:
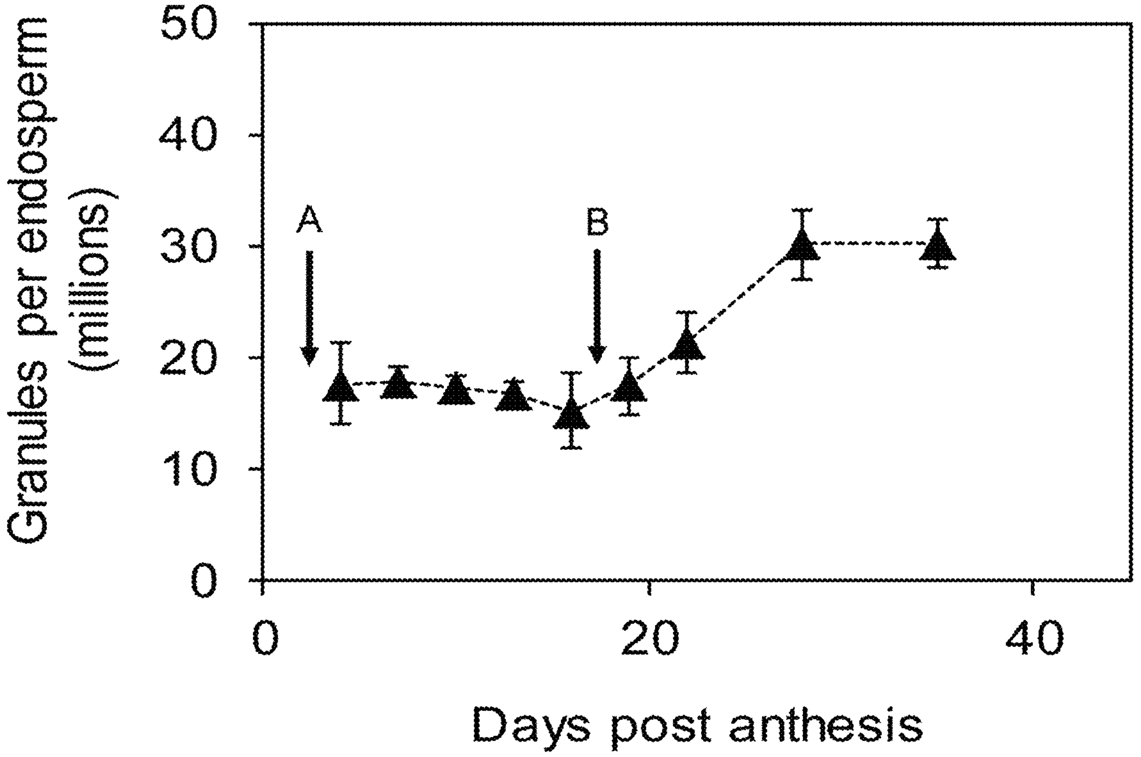
FIG. 2 is a graph showing granule initiation during grain development in *Aegilops;*

Wheat and other domesticated Triticeae species (as defined herein), other than oats but including without limitation barley and rye, produce both A-type and B-type starch granules within the grain endosperm (see FIG. 1). Granule initiation occurs at two separate time points during grain development (see FIG. 2), with A-type granules being initiated shortly after anthesis, whilst initiation of B-type granules occurs much later. Since all wheat cultivars produce both A and B-type granules, conventional methods of breeding cannot be used to eliminate the B-type granule in wheat. A similar low genetic diversity for the trait of B-type granules is also observed in barley. Oats also produce small granules within the grain endosperm which further contains compound granules (see Saccomanno et al. 2017, Journal of Cereal Science 76: 46-54). Although conventionally, for oats, the small granules are not designated as B-type granules, for convenience and consistency this terminology is used herein to also refer to the distinct population of small granules observed in oat endosperm.

Analysis of granule type within the endosperm has been reported in the literature (summarised in Saccomanno et al. 2017, Journal of Cereal Science 76: 46-54) as (where the term "simple granule" is used to refer to the small granules referenced herein as "B-type granules"):

TABLE A

| | Oats | Wheat | Barley |
|---|---|---|---|
| Simple granule diameter (μm) | 4-10 | <10 | 2-5 |
| Compound granule diameter (μm) | 20-150 | — | — |

TABLE A-continued

| | Oats | Wheat | Barley |
|---|---|---|---|
| Simple granule volume ($\mu m^3$) | — | 10-35 | 12-32 |
| Compound granule volume ($\mu m^3$) | 64 | 56.6 | 10.9 |
| A-granule volume ($\mu m^3$) | — | 1824 | 1242 |
| Simple granules (% by number) | 91% | 90% | 92% |
| Simple granules (% by volume) | 10% | <30% | 9% |

Simply for convenience of reference, the term "domesticated Triticeae species" as used herein refers to plants classified as Triticeae and also to the following other cereals and grasses: Aveneae; *Hordeum vulgare* (barley); and *Triticum aestivum* (common wheat or bread wheat), but specifically excludes *Aegilops* grasses. In particular, the term "domesticated Triticeae species" refers to Triticeae and Aveneae plants which are classified as cereals (i.e. produce edible grain). More specifically, the term "domesticated Triticeae species" refers to small grain temperate cereals classified as Triticeae and Aveneae. Non-limiting examples include common wheat, barley, rye, durum wheat, spelt wheat, triticale, einkorn wheat and oats. The term "domesticated Triticeae species" as used herein can refer to common wheat, barley, rye, durum wheat, spelt wheat, triticale, and einkorn wheat. Any cultivar of these cereals can be used in the present invention. Common wheat, barley, rye and oats are of particular interest. Preferably the cultivar is suitable for commercial growth.

Where the term "wheat" is used herein without a further qualifier, it refers a plant of the genus *Triticum* and therefore includes common wheat (also termed "bread wheat"), namely *Triticum aestivum*, durum wheat (*Triticum durum*), spelt (a form of *Triticum aestivum*) and einkorn (*Triticum boeoticum* or the domesticated form, *Triticum monococcum*). References to "durum" are to durum wheat; to "spelt" are to spelt wheat; and to "einkorn" are to einkorn wheat. Preferred forms of "wheat" as referenced herein are common wheat (also termed "bread wheat"), namely *Triticum aestivum*, and durum wheat (*Triticum durum*).

The term "B-type granule" refers to a distinct population of small granule type observed within the endosperm of wheat. B-type granules have a diameter of 10 μm or less.

It is an object of the present invention to provide a plant of domesticated Triticeae species able to produce a grain with a modified (i.e. decreased or increased) level (i.e. number or content by weight or volume) of B-type granules within the endosperm relative to the unmodified form of the grain. For example, the number of B-type granules within the endosperm can be modified by 10% or more relative to the unmodified form of the grain, for example can be modified by 20%, 30%, 40%, 50%, 60%, 70%, 80%, 90%, 95%, 98% or 99% relative to the unmodified form of the grain. For example, the number of B-type granules within the endosperm can be reduced by 10% or more relative to the unmodified form of the grain, for example can be reduced by 20%, 30%, 40%, 50%, 60%, 70%, 80%, 90%, 95%, 98% or 99% relative to the unmodified form of the grain. Alternatively, the weight of the B-type granules within the endosperm can be reduced by 10% or more relative to the unmodified form of the grain, for example can be reduced by 20%, 30%, 40%, 50%, 60%, 70%, 80%, 90%, 95%, 98% or 100% or more relative to the unmodified form of the grain. Optionally, the grain substantially lacks B-type granules. The grain can be of any domesticated Triticeae species (as herein defined), but specific mention can be made of common wheat, barley, rye, and oats. Optionally, the grain does not produce any B-type granules in the endosperm since initiation of this granule type does not occur.

Methods for measurement of granule content by number are well-known in the art. Exemplary methods include the use of a laser diffraction particle size analyser. Use of a laser diffraction particle size analyser requires a relatively large sample to be available for analysis and may not be suitable for all grain types. For example this method cannot be used to analyse oat grains which contain compound particles, as the procedure used causes the compound granules to disintegrate. A suitable alternative method analyses the sample by viewing individual grains using a microscope and manually counting the granule number within a sample view. Multiple views of each sample can be used to enhance accuracy. Further, each sample view can be photographed so that granule count can be conducted using image analysis. Granule weight and volume can be calculated following analysis of granule number. A review of granule size determination techniques can be found in Lindeboom et al., 2004, Starch 56:89-99.

In common wheat (*Triticum aestivum*), barley (*Hordeum vulgare*) or oats (*Avena sativa*) the endosperm of an unmodified grain will typically contain approximately 90% B-type granules and 10% A-type granules, when granule content is assessed by granule number. In the present invention, the modified endosperm can contain 80% B-type granules or less, for example 70% B-type granules, for example 60%, 50%, 40%, 30%, 20% or 10% B-type granules or less when assessed by granule number (with the remainder being A-type granules (common wheat, rye or barley) or compound granules (oats)).

Since B-type granules are very small, the percentage number of this granule type within the endosperm is high. However, in terms of their content by weight, the much larger A-type granules are more significant. Analysis of granule content by weight (or volume) can be obtained through calculation, following completion of analysis of granule number and size.

In common wheat, *Triticum aestivum*, the endosperm of an unmodified grain will typically contain approximately 30% B-type granules and 70% A-type granules, when granule content is assessed by weight or volume. In the present invention, the modified endosperm can contain 25% B-type granules or less, for example 20% or less, for example 10% or less, or even 5% or less B-type granules when assessed by weight or volume (with the remainder being A-type granules). For barley (*Hordeum vulgare*), the endosperm of an unmodified grain will typically contain approximately 10% B-type granules and 90% A-type granules, when granule content is assessed by weight or volume. In the present invention, the modified endosperm can contain 8% B-type granules or less, for example 5% or less, for example 3% or less, or even 1% or less B-type granules when assessed by weight or volume (with the remainder being A-type granules). For oats, the endosperm of an unmodified grain will typically contain approximately 33% of B-type granules when assessed by weight or volume, with the remainder being compound granules. In the present invention, the modified endosperm can contain 30% B-type granules or less, for example 25% or less, for example 20% or less, for example 10% or less, or even 5% or less B-type granules when assessed by weight or volume. Preferably, the present invention provides a plant of a domesticated Triticeae species wherein the percentage weight or volume of B-type granules (relative to the whole granule content of the endosperm) is reduced by 5% or more, for example is reduced by 10% or more.

Alternatively the grain can exhibit an increased B-granule content within the endosperm, for example the level (number or weight or volume) of B-type granule can be increased by at least 20%, for example at least 30%, 40%, 50%, 60%, 70%, 80%, 90% or 100% relative to the level observed in the unmodified grain. Optionally the granule number of B-type granules is increased from 90% to 95% or more, for example to 98% or 99% or more. Optionally the grain can consist predominantly of small (i.e. B-type) granules (for example in wheat, barley and oats). Optionally, when assessed by granule weight (or volume) the B-type granule content for wheat is increased from 30% to at least 50%, for example to 60% or more, to 70% or more, 80% or more or to 90% or more. Optionally, when assessed by granule weight (or volume) the B-type granule content for barley is increased from 10% to at least 30%, for example to 40% or more, to 50% or more, to 60% or more, to 70% or more, to 80% or more or to 90% or more. Optionally, when assessed by granule weight (or volume) the B-type granule content for oats is increased from 30% to at least 50%, for example to 60% or more, to 70% or more, to 80% or more or to 90% or more.

It is a further object of the present invention to provide methods for the selective modification of B-type granule content in the grain of a domesticated Triticeae species, and to provide a domesticated Triticeae species able to form grain with modified levels of B-type granules within the grain, and in particular to provide wheat and/or oats and/or barley and/or rye plants able to form grain with modified levels of B-type granules within the grain as described above. The methods include the modification of the Bgc-1 QTL marker gene or its control elements using the genetic information provided herein either by manipulation of its sequence to produce a non-functional expression product (thereby reducing B-type granule content) or by manipulation of its promoter or other elements affecting control of its expression (thereby selectively increasing or decreasing B-type granule content). Alternative methods include crossing the B-less wheat produced by the present inventors (or the progeny thereof) with domesticated Triticeae plants (preferably commercial cultivars) and selecting for progeny having the required modified levels of B-type granules within the grain or selecting for the ability to produce grain having modified levels of B-type granules. The method can further comprise a step of backcrossing and selecting plants able to produce grain with a modified number, weight or volume of B-type granules within the endosperm. Molecular markers and other genetic analysis (e.g. sequencing) can be used to enhance the efficiency of selection.

It is a further object of the present invention to provide methods for the selective modification of B-type granule content in the grain of a wheat plant, and to provide a wheat plants able to form grain with modified levels of B-type granules within the grain, and in particular to provide wheat plants able to form grain with modified levels of B-type granules within the grain as described above. The methods include the modification of the wheat Flo6 gene (also designated as TaFlo6) or its control elements using the genetic information provided herein either by manipulation of its sequence to produce a non-functional (or reduced activity) expression product (thereby reducing B-type granule content) or by manipulation of its promoter or other elements affecting control of its expression (thereby selectively increasing or decreasing B-type granule content). Alternative methods include crossing the B-less wheat produced by the present inventors (or the progeny thereof) with domesticated Triticeae plants (preferably commercial cultivars, for example of wheat) and selecting for progeny having the required modified levels of B-type granules within the grain or selecting for the ability to produce grain having modified levels of B-type granules. The method can further comprise a step of backcrossing and selecting plants able to produce grain with a modified number, weight or volume of B-type granules within the endosperm. Molecular markers and other genetic analysis (e.g. sequencing) can be used to enhance the efficiency of selection. Surprisingly, it has been found that the wheat Flo6 gene can be manipulated in wheat in a dose-dependent manner, i.e. not all of the gene copies present need to be mutated to observe a reduction in B-granule content. Thus, in a hexaploid wheat, mutation of 3 of the 6 Flo6 genes provide a phenotype having fewer B granules relative to the wild type but a further decrease in B granule content (to essentially zero B-granules) can be obtained with mutation of 4 of the 6 Flo6 genes. In a tetraploid wheat, mutation of 2 of the 4 gene copies present will result in a grain with a small decrease in B granule content relative to the wild type but a further decrease in B granule content can be obtained with mutation of 3 of the 4 Flo6 genes. Mutation of all 4 gene copies in a tetraploid wheat, where two mutated copies have nonsense mutations and 2 have missense mutations, will result in a grain with substantially no B-granules.

Thus, the present invention provides methods for the selective reduction of B-type granule number in the grain of a domesticated Triticeae species, and provides a domesticated Triticeae species plant having decreased levels of B-type granules within the grain. In particular the present invention provides wheat and/or barley and/or oats and/or rye plants with decreased levels of B-type granules within the grain, for example with substantially no B-type granules (small granules) within the grain. In particular the present invention provides wheat plants with decreased level of B-type granules within the grain, for example with substantially no B-type granules within the grain.

In one aspect, the method of the present invention can lead to the number of B-type granules being decreased by 10% or more relative to the unmodified form of the grain, for example the number of B-type granules in the grain can be reduced by 20%, 30%, 40%, 50%, 60%, 70%, 80%, 90%, 95%, 98% or 99% relative to the unmodified form of the grain. Optionally, the modified endosperm can contain 80% B-type granules or less, for example 70% B-type granules, for example 60%, 50%, 40%, 30%, 20% or 10% B-type granules or less when assessed by granule number (with the remainder being A-type granules (common wheat, rye or barley) or compound granules (oats)). Preferably, the percentage weight or volume of B-type granules (relative to the whole granule content of the endosperm) is reduced by 5% or more, for example is reduced by 10% or more.

Optionally, the method of the present invention can produce a grain which substantially lacks B-type granules. Optionally, the method can produce a grain which lacks any B-type granules in the endosperm (since initiation of this granule type does not occur). The method can be used with any domesticated Triticeae species (as herein defined), but specific mention can be made of wheat, barley, rye, and oats. Wheat is particularly of interest. Commercial cultivars are of particular interest.

Optionally, the method of the present invention can produce a wheat plant able to produce a grain comprising an endosperm which contains 25% B-type granules or less, for example 20% or less, for example 10% or less, or even 5% or less B-type granules when assessed by weight or volume (with the remainder being A-type granules). Optionally, the method of the present invention can produce a barley plant able to produce a grain comprising an endosperm which contains 8% B-type granules or less, for example 5% or less, for example 3% or less, or even 1% or less B-type granules when assessed by weight or volume (with the remainder being A-type granules). Optionally, the method of the present invention can produce an oat plant able to produce a grain comprising an endosperm which contains 30% B-type granules or less, for example 25% or less, for example 20% or less, for example 10% or less, or even 5% or less B-type granules when assessed by weight or volume (with the remainder being compound granules). The method also covers the grain formed by the plants described above.

In one aspect, the method of the present invention can lead to a domesticated Triticeae plant able to produce grain in which the level of B-type granule is increased by at least 20%, for example at least 30%, 40%, 50%, 60%, 70%, 80%, 90% or 100% relative to the level of these granules observed in the unmodified grain. Optionally the method can produce grain which consists predominantly of small (i.e. B-type) granules. Thus the grain produced can lack large A-type granules (for example in wheat, barley, and rye) or can lack compound granules (for example in oats). In one embodiment the domesticated Triticeae plant is a wheat plant.

Thus, the present invention provides methods for the selective increase of B-type granule number in the grain of a domesticated Triticeae species, and provides a domesticated Triticeae species plant having increased levels of B-type granules within the grain. In particular the present invention provides wheat and/or barley and/or oats and/or rye plants with increased levels of B-type granules (i.e. small granules) within the grain, for example with substantially all B-type granules within the grain. In one embodiment the domesticated Triticeae plant is a wheat plant.

In one aspect, the present invention provides a domesticated Triticeae species plant able to form grain wherein the level (granule number or weight or volume) of B-type granule within the endosperm is increased by at least 20%, for example at least 30%, 40%, 50%, 60%, 70%, 80%, 90% or 100% relative to the level of these granules observed in the unmodified grain. In particular the present invention provides wheat and/or barley and/or oats and/or rye plants with increased levels of B-type granules (i.e. small granules) within the grain, for example at least 30%, 40%, 50%, 60%, 70%, 80%, 90% or 100% more B-type granules relative to the number of these granules observed in the unmodified grain. Optionally the method can produce grain which consists predominantly of small (i.e. B-type) granules. Thus the grain produced can lack large A-type granules (for example in wheat, and barley). In certain embodiments (for example in oats), the method can produce grain which consists predominantly of compound granules. In one embodiment the domesticated Triticeae plant is a wheat plant.

It is a further object of the present invention to provide methods for the selection of a domesticated cereal plant of a Triticeae species (for example a cereal such as wheat, oats, barley or rye) which produces grain endosperm which lacks B-type granules by the evaluation of the genome. In particular the sequence of the gene Bgc-1 in any individual plant can be analysed for selection, for example by DNA sequencing, analysis of granule content or other techniques. In one embodiment the domesticated Triticeae plant is a wheat plant.

It is a further object of the present invention to provide methods for the selection of a domesticated cereal plant of the Triticeae species (for example a cereal such as wheat, oats, barley or rye) which produces grain endosperm which substantially consists of B-type granules by the evaluation of the genome. Preferably the domesticated cereal plant is a cultivar suitable for commercial use. In one embodiment the domesticated Triticeae plant is a wheat plant.

It is a yet further object of the present invention to provide flour milled from the grain of a plant of domesticated Triticeae species (for example a cereal such as wheat, oats, barley or rye), wherein said grain has modified levels of B-type granules. The modified levels can be an increased level or a decreased level (i.e. number) of B-type granules, as compared to the unmodified form of the grain as is described above. Optionally the modified grain can have substantially no B-type granules within the grain. Optionally the starch content of the modified grain can consist predominantly of B-type granules. The modified grain can be produced from a plant of a domesticated Triticeae species (preferably from a cultivar suitable for commercial use) according to the invention.

It is a still further object of the present invention to provide compositions of matter comprising grain and/or flour milled from the grain of a plant of domesticated Triticeae species with modified levels of B-type granules within the grain according to the present invention and as described above. In particular, the modified levels of B-type granules can be an increased level or a decreased level (i.e. number) of B-type granules, as compared to the unmodified form of the grain. Optionally the modified grain (or flour produced therefrom) can have substantially no B-type granules within the grain. Optionally the modified grain (or flour produced therefrom) can have a starch content which consists predominantly of B-type granules.

These and other objects of the invention are provided by one or more of the embodiments described below.

Manipulation of the genome of polyploid wheat and oats is particularly complex and difficult. For example, *T. aestivum* is an allohexaploid having 3 genomes, each consisting of 7 pairs of chromosomes, and each believed to originate from a different diploid parent. The genomes are identified as A, B and D. Thus, any phenotypic trait within wheat can be due to gene expression from a minimum of one of any one of the 6 homoeologous chromosomes. Additionally the polyploid wheat genome means that a mutation in any one genome can be phenotypically masked due to expression of an equivalent gene in one of the other genomes.

For the first time, the inventors have produced a wheat plant which does not produce B-type starch granules within its endosperm. Seeds of this plant have been deposited at the National Collections of Industrial, Food and Marine Bacteria (NCIMB) (Ferguson Building, Craibstone Estate, Bucksburn, Aberdeen AB21 9YA, UK) on 8 Feb. 2017 under Accession No. NCIMB 42723). The B-less wheat plants can be crossed with commercial wheat varieties to produce commercial common wheat with modified B-type granule content, for example with reduced B-type granule content as described above.

Figure 3A:
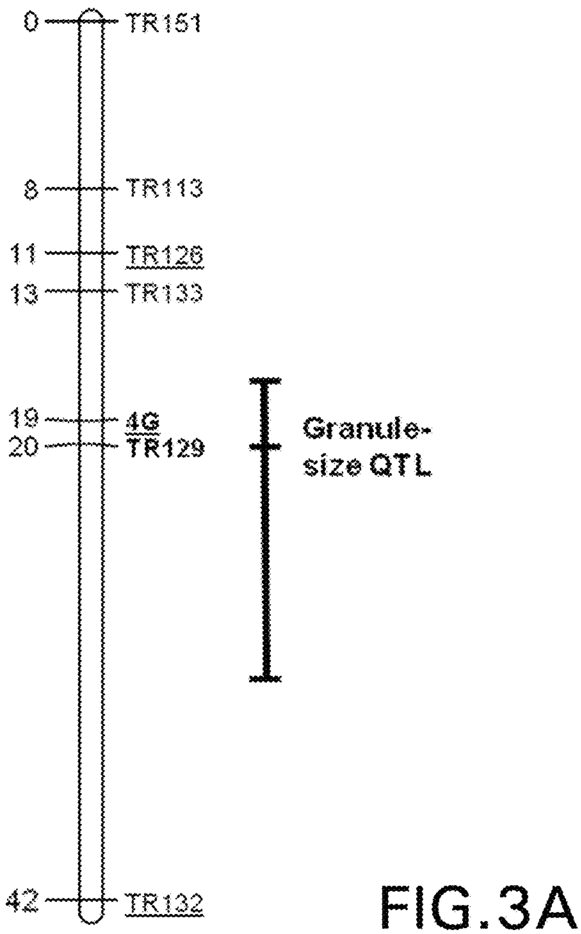
FIGS. 3A-B are a schematic and a graph relating to QTL location, and B-granule number, respectively.
Figure 3B:
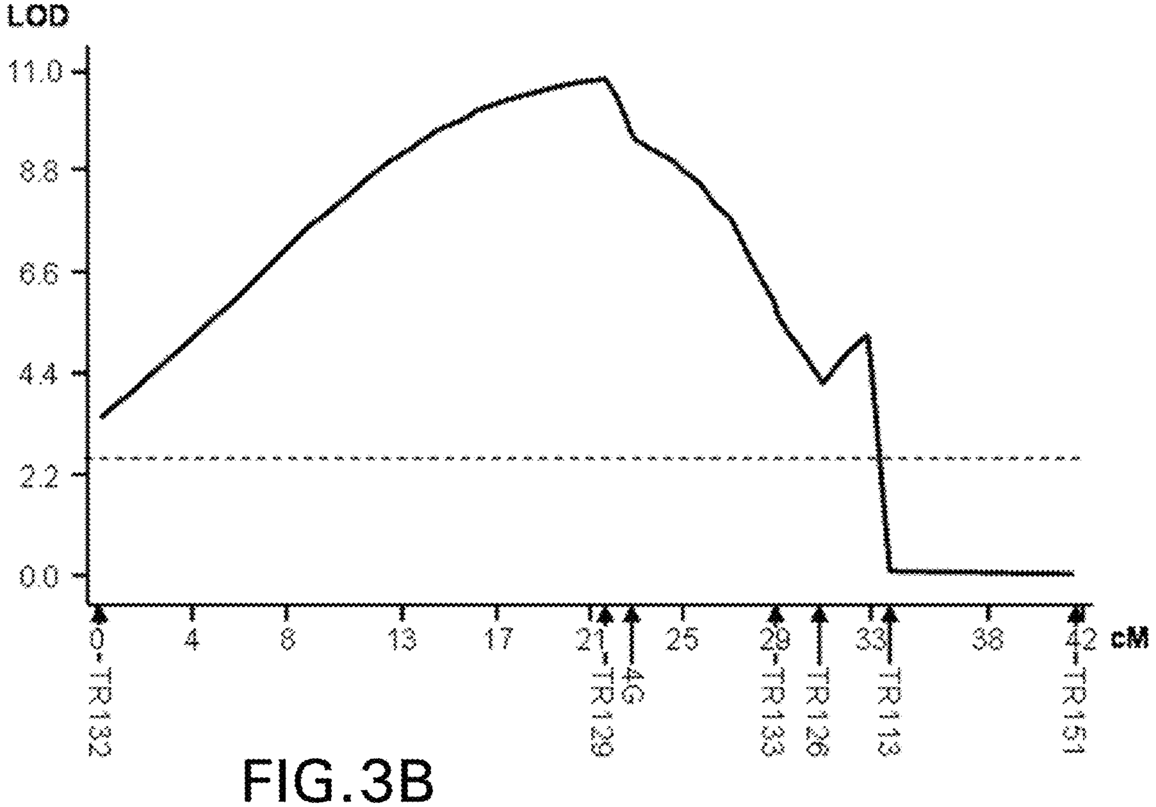

The wheat plant lacking B-type granules (*Triticum aestivum* cv Paragon) was produced following identification of a QTL locus responsible for B-type granule production in *Aegilops* (FIG. 3). The *Aegilops* gene at the QTL locus responsible for initiation of B-type starch granule synthesis has been designated as B-granule content 1 (Bgc-1).

The presence of B-type granules within the grain of domesticated Triticeae species was postulated to be due to expression of the orthologue of *Aegilops* gene Bgc-1, such that inactivation of this gene by suitable mutation (including deletion or point mutation) or by other known techniques (e.g. reduced expression due to RNAi or gene editing) can produce grain with decreased levels of B-type granules, for example grains which substantially lack B-type granules or in which B-type granules are absent. In wheat, the orthologues of Bgc-1 that control B-granule content are predicted from conservation of gene order between related species to lie on chromosomes 4AL, 4BS and 4DS.

The inventors have further found that, within wheat *Triticum aestivum* (cultivar Paragon), there are active Bgc-1 QTL marker genes that control B-granule content on two of the three group 4 chromosomes: 4AL and 4DS. A publically-available collection of deletion mutants of Paragon wheat (M4 generation) was screened for the presence/absence of genes predicted to flank Bgc-1 and a double deletion mutant, with deletions in the A and D genomes, was produced by crossing resulting in a single wheat plant which lacked B-type granules. The B genome copy of Bgc-1 is presumed to be inactive in Paragon.

The present invention provides a wheat plant having mutations or deletions in the Bgc-1 QTL marker genes on chromosomes 4AL and/or 4DS for use in the production of a progeny plant which produces decreased levels of B-type granules in its endosperm, preferably which produces no B-type granules in its endosperm.

Thus the present invention further provides grain from wheat plants which contains decreased levels of B-type granules in its endosperm (preferably which has no B-type granules in its endosperm) and to flour and/or compositions of matter produced therefrom.

A candidate Bgc-1 QTL marker gene (cBgc-1) was identified by fine mapping in *Aegilops*.

The genomic sequence for functional Bgc-1 found in the synthetic tetraploid KU37 is given as SEQ ID No. 1, with the corresponding amino acid sequence of the expressed Bgc-1 protein being set out at SEQ ID No. 4. It was postulated that expression of this gene enabled KU37 to produce B-type granules within its endosperm.

In contrast, neither native *Aegilops peregrina* nor *Aegilops crassa* produce B-type granules; analysis of their endosperms shows that only A-type granules are present. The corresponding genomic Bgc-1 sequences are given in SEQ ID Nos. 2 and 3, respectively, and the corresponding amino acid sequence are given as SEQ ID Nos. 5 and 6, respectively.

Comparison of SEQ ID Nos. 4 (KU37) and 5 (*A. peregrina*) show a single amino acid change at position 824. In KU37 the amino acid is alanine, whereas in *A. peregrina* the amino acid at this position is proline. Similarly, comparison of SEQ ID Nos. 4 (KU37) and 6 (*A. crassa*) shows a single amino acid change at position 475. In KU37 the amino acid is proline (Pro491), whereas in *A. crassa* the amino acid at the equivalent position (475) is leucine.

The present invention provides a Bgc-1 protein comprising at least one amino acid substitution mutation, for example at the position or positions functionally equivalent to Pro491 and/or Ala824 of SEQ ID No. 4.

Figure 7A:
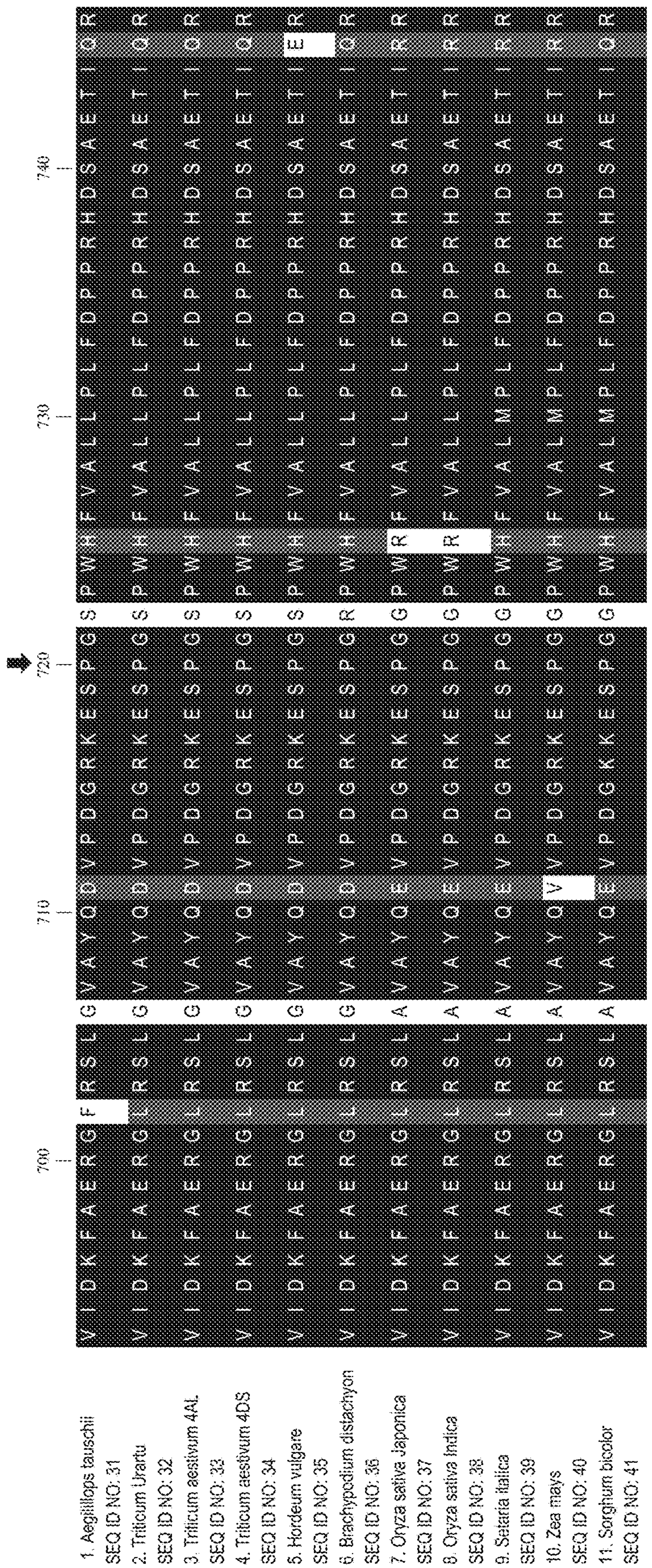
FIGS. 7A-B show alignment comparisons of protein sequences showing that in FIG. 7A. the Alanine (A, see arrow) that is altered in *A. peregrina* to Proline (P) is highly conserved in other grass species (SEQ ID Nos 31 to 41) and in FIG. 7B. the Proline (P, see arrow) that is altered in *A. crassa* to Leucine (L) is highly conserved in other grass species (SEQ ID Nos. 42 to 52).
Figure 7B:
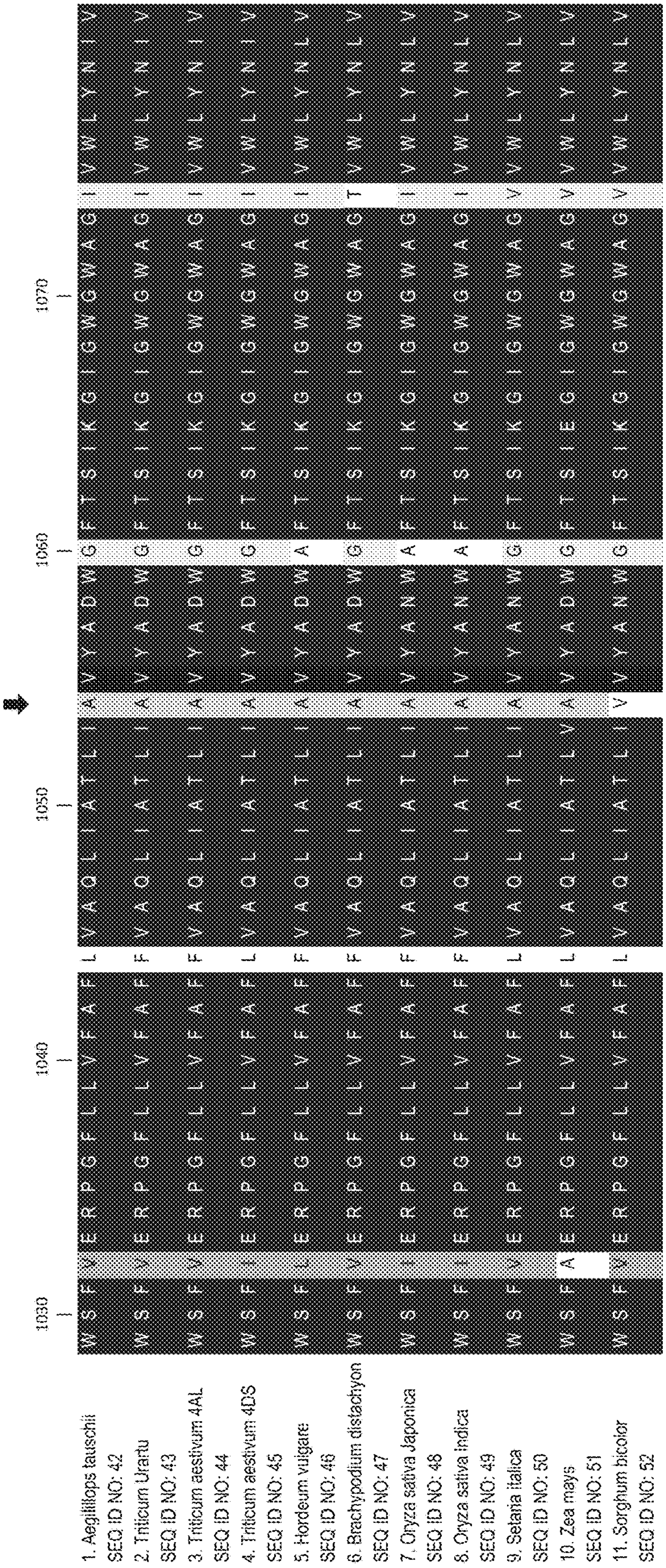

The present invention provides a genetically modified form of the gene Bgc-1 which expresses a non-functional protein. For example, the codons for Pro491 and/or Ala824 of SEQ ID No 4 (or functional equivalents thereof) can be altered to produce non-functional expression product. Optionally, the codon for Ala824 is modified to express Proline. By "functionally equivalent" it is meant that the amino acid substitution is considered to occur at the amino acid position that has the same functional role in the protein. Generally functionally equivalent substitution mutations in two or more different proteins occur at homologous amino acid positions in the amino acid sequences. An example of sequence alignment to identify functionally equivalent residues is shown in FIG. 7.

Techniques for changing a codon are well-known within the art, and include, but are not limited to: RNAi, crispr cas9, TILLING mutants, deletion mutants, site-directed point mutagenesis, random point mutagenesis, in vitro or in vivo homologous recombination (DNA shuffling and combinatorial overlap PCR), mutagenesis using uracil containing templates, oligonucleotide-directed mutagenesis, phosphorothioate-modified DNA mutagenesis, mutagenesis using gapped duplex DNA, point mismatch repair, mutagenesis using repair-deficient host strains, restriction-selection and restriction-purification, deletion mutagenesis, mutagenesis by total gene synthesis, degenerate PCR, double-strand break repair, and many others known in the art.

Also presented herein is a nucleic acid molecule encoding an altered Bgc-1 protein as defined in any the above embodiments. Also presented herein is an expression vector comprising the nucleic acid molecule described above. Also presented herein is a host cell comprising the vector described above.

A method to reduce B-type granule content in the endosperm of plants of domesticated Triticeae species comprises the step of introducing a mutation within the gene Bgc-1 which affects functionality of the expression product, for example to produce a non-functional expression product. For example, the codons for 491 Pro and/or 824 Ala (relative to SEQ ID No 4 or the functional equivalents thereof) can be modified to affect the amino acid type such that a non-functional protein is produced.

Comparison of the orthologous sequences in other grasses, including Triticeae species (*Aegilops tauschii, Triticum uratu, Triticum aestivum, Hordeum vulgare*) which, like KU37 have B-type starch granules, shows that Alanine-824 and Proline-475 (Proline 491 of SEQ ID No. 4) are highly conserved. It was postulated that the presence of Proline at position 824 in the *Aegilops peregrina* sequence and the presence of Leucine at position 475 in *A. crassa* is sufficient to prevent functional protein from being produced, and ultimately to prevent B-type granule production.

Comparison of SEQ ID Nos. 1 (KU37) and 2 (*A. peregrina*) shows that a single nucleotide point mutation causes the amino acid shift. In SEQ ID No. 1 (KU37), nucleotide 5392 is "g", whereas the equivalent nucleotide in SEQ ID No. 2 (*A. peregrina*) is 5380 which is "c". Thus the DNA codon changes from GCT in the functional protein to CCT in the non-functional protein.

Comparison of SEQ ID Nos. 1 (KU37) and 3 (*A. crassa*) shows that a single nucleotide point mutation causes the amino acid shift. In SEQ ID No. 1 (KU37), nucleotide 3213 is "c", whereas the equivalent nucleotide in SEQ ID No. 3 (*A. crassa*) is 2933 which is "t". Thus the DNA codon changes from CCG in the functional protein to CTG in the non-functional protein.

From analysis from the sequences of SEQ ID Nos. 1 to 6, it is further postulated that the BGC-1 protein is a protein pumping ATPase. The ATPase is postulated to be located in the plasma membrane.

The present invention contemplates the use of suitable genetic manipulation techniques to inactivate orthologues of Bgc-1 in different species in order to modify B-granule content. As an example, the Bgc-1 orthologues in wheat are: (A1) TRIAE_CS42_4AL_TGACv1_288750_AA0957220, (A2) TRIAE_CS42_4AL_TGACv1_290111_AA0981820, (B) TRIAE_CS42_4BS_TGACv1_328355_AA1086780, (D) TRIAE_CS42_4DS_TGACv1_361106_AA1161080.

The corresponding orthologue in barley is MLOC_52920.

The corresponding orthologue in *Triticum* uratu is TRIUR3_02152, TRIUR3_05748.

The corresponding orthologue in *Aegilops tauschii* is F775_14999.

The present invention also lists orthologues in other species. It is contemplated that Bgc-1 mutants in various species can now be generated using techniques known in the art (including RNAi, crispr cas9, TILLING mutants, deletion mutants and the selection of natural genetic variants or other techniques as listed above). The following are domesticated Triticeae species as defined herein: *Hordeum vulgare* (barley), *Triticum aestivum* (common wheat).

It is contemplated that deletion or substitution mutants of the above orthologs can now be generated using techniques known in the art.

Figures 8A, 8B:
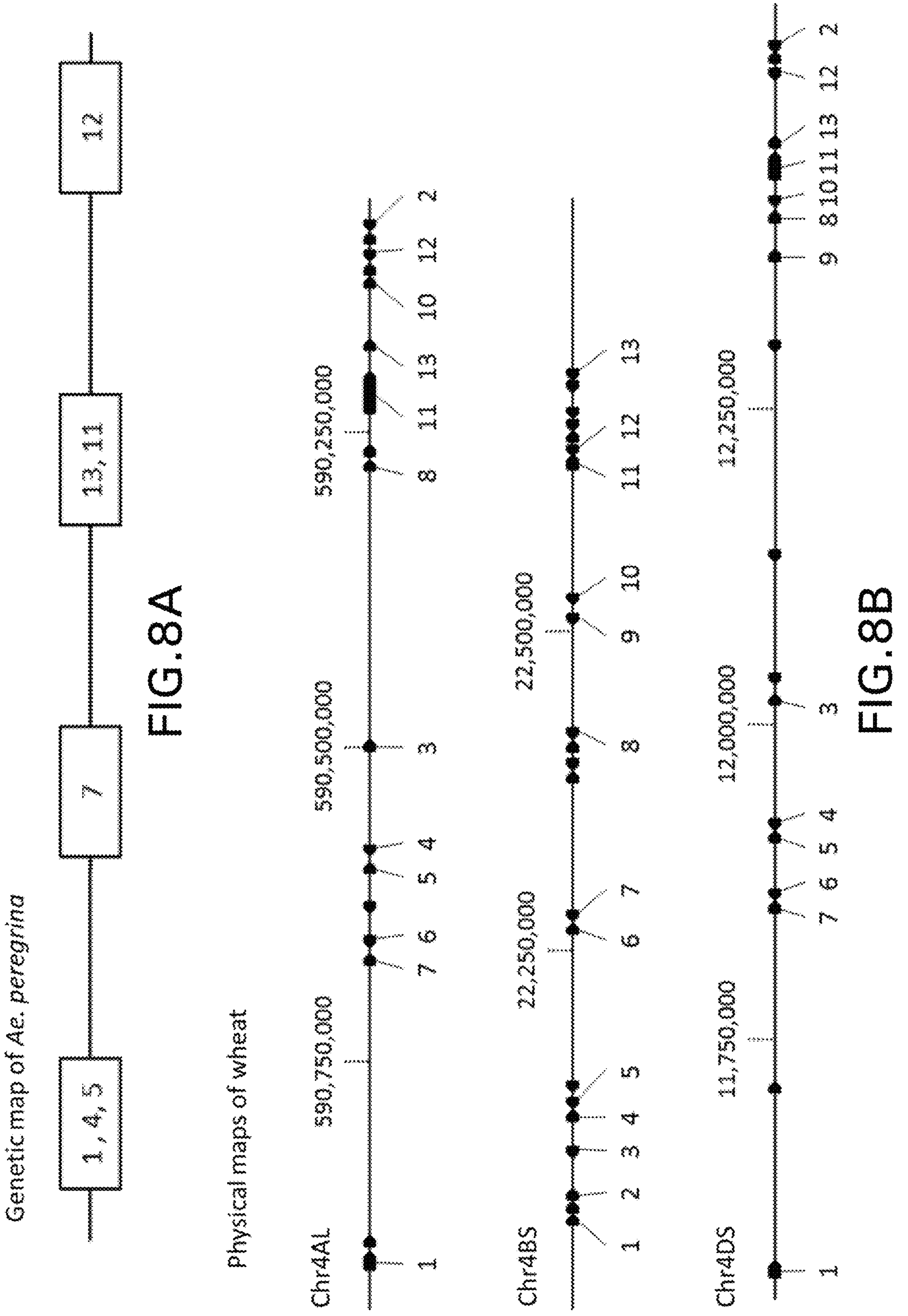
FIGS. 8A-B show physical and genetic maps of wheat and *Aegilops.*
The locations of genes in the Bgc-1 regions of *A. peregrina* and wheat are shown. Genes are numbered as in Table 2. Orthologous genes have the same number in each map.
Figure 9A:
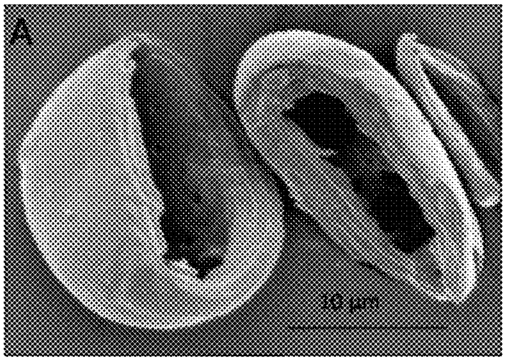
FIGS. 9A-D show SEM images of etched starch granules from Franubet barley. The growth-ring structure within the starch granules was revealed by cracking starch by grinding and then partially digesting. The granules in wild-type Nubet starch (FIGS. 9A, B) each consists of a single ring structure suggesting a single initiation point. Some of the starch granules in the mutant Franubet are compound and contain multiple separately-initiated granulae, each with their own ring structure. In some compound granules (FIGS. 9C, D), a continuous outer layer of starch rings surrounding the granulae can be seen (indicated by the arrows) suggesting that Franubet also contains some semi-compound granules.
Figure 9C:
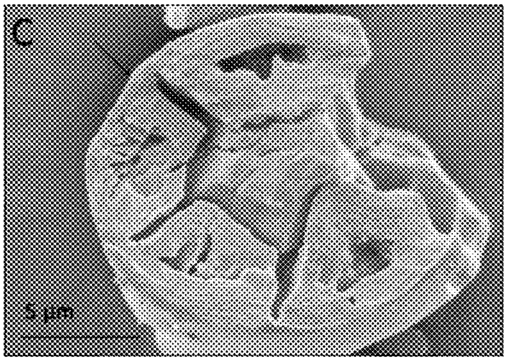
Figure 9B:
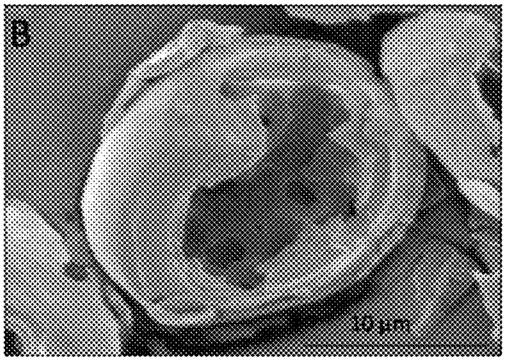
Figure 9D:
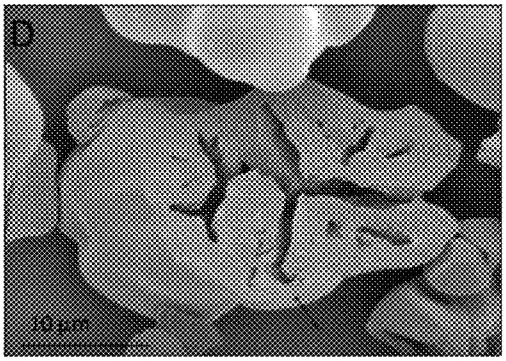

However, as noted above subsequent work has clarified that the Bgc-1 QTL marker gene (SEQ ID No. 1) and expressed protein sequence (SEQ ID No. 4), despite the initial promising results, are not responsible for B-granule initiation. Further fine mapping in *Aegilops* refined the region containing the gene responsible for controlling B-granule content (FIG. 8). Surprisingly it has been found that the gene responsible for the B-less wheat mutants generated by the inventors is Flo6, a gene which is known to affect starch formation in barley and rice, which but exhibits a very different phenotype in those species.

The wheat Flo6 gene is given in SEQ ID No. 53. Kronos TILLING mutant lines affected in the Flo6 gene were selected and are given below:

TABLE B

| Gene | Chromosome | Mutant ID | Effect on TaFlo6 |
|---|---|---|---|
| TraesCS4A01G284000 | A | K2244 | Trp291 to STOP |
| | A | K3145 | Trp400 to STOP |
| TraesCS4B01G029700 | B | K0456 | Glu469 to Lys |
| | B | K3239 | Val470 to Ile |

When lines K2244 and K3239 were crossed together and a double mutant was selected from the $F_2$ progeny it was found to lack B-type starch granules. Thus the present invention further provides grain from wheat plants which contains decreased levels of B-type granules in its endosperm (preferably which has no B-type granules in its endosperm) and to flour and/or compositions of matter produced therefrom.

The genomic sequence for functional Flo6 in wheat is given as SEQ ID No. 53 (A genome), as SEQ ID No. 55 (B genome), and as SEQ ID No. 57 (D genome), with the respective corresponding amino acid sequence of the expressed protein being set out at SEQ ID Nos. 54, 56 and 58. Expression of this gene enables enable wheat to produce B-type granules within its endosperm. There is a dosage effect to gene expression.

The present invention provides a wheat FLO6 protein comprising at least one amino acid substitution mutation, for example a STOP codon at Trp291 or Trp400 (A genome) and/or the equivalent locations in the B and/or D genomes.

The present invention provides a wheat FLO6 protein comprising at least one amino acid substitution mutation, for example a Glu469 to Lys and/or Val470 to Ile in the B genome and/or the equivalent locations in the A and/or D genomes.

The present invention provides a genetically modified form of the wheat gene Flo6 which expresses a non-functional protein. For example, the codons for at Trp291 or Trp400 of SEQ ID No 53 (or functional equivalents thereof) can be altered to produce non-functional expression product. Optionally, the codon for Glu469 (B genome) is modified to express lysine. Optionally, the codon for Val470 is modified to express Isoleucine. By "functionally equivalent" it is meant that the amino acid substitution is considered to occur at the amino acid position that has the same functional role in the protein. Generally functionally equivalent substitution mutations in two or more different proteins occur at homologous amino acid positions in the amino acid sequences. An example of sequence alignment to identify functionally equivalent residues is shown in FIG. 10.

Techniques for changing a codon are well-known within the art, and include, but are not limited to: RNAi, crispr cas9, TILLING mutants, deletion mutants, site-directed point mutagenesis, random point mutagenesis, in vitro or in vivo homologous recombination (DNA shuffling and combinatorial overlap PCR), mutagenesis using uracil containing templates, oligonucleotide-directed mutagenesis, phosphorothioate-modified DNA mutagenesis, mutagenesis using gapped duplex DNA, point mismatch repair, mutagenesis using repair-deficient host strains, restriction-selection and restriction-purification, deletion mutagenesis, mutagenesis by total gene synthesis, degenerate PCR, double-strand break repair, and many others known in the art.

Also presented herein is a nucleic acid molecule encoding an altered wheat FLO6 protein as defined in any the above embodiments. Also presented herein is an expression vector comprising the nucleic acid molecule described above. Also presented herein is a host cell comprising the vector described above.

A method to reduce B-type granule content in the endosperm of wheat plants comprises the step of introducing a mutation within the gene Flo6 which affects functionality of the expression product, for example to produce a non-functional expression product, within at least one genome, optionally within two genomes or within 3 genomes (for hexaploid wheat). For example, the codons for Trp291 or Trp400 (relative to SEQ ID No 53 or the functional equivalents thereof) can be modified to affect the amino acid type such that a non-functional protein is produced.

In particular, cereal grain (e.g. wheat, barley, rye or oat grain) with decreased levels of B-type granules in its endosperm are likely to be of commercial importance in the production of bread, the production of alcohol (for example for beer or whisky and industrial alcohol), as starch additives for food production, and for biscuits (cookies). Other uses within the food and drink industry and non-food uses are also contemplated.

Preferred or alternative features of each aspect or embodiment of the invention apply mutatis mutandis to each aspect or embodiment of the invention (unless the context demands otherwise).

The term "comprising" as used herein means consisting of, consisting essentially of, or including and each use of the word "comprising" or "comprises" can be independently revised by replacement with the term "includes", "consists essentially of" or "consists of".

Examples

Location of Bac-1 in Goat Grass (*Aegilops*)

A population of *Aegilops* which segregated for B-type granules was produced as described in Howard et al., supra.

Analysis of granule-size distribution within the segregating population suggested that a single locus (Bgc-1) is responsible for B-granule content. The region of the genome responsible for initiation of B-type granule production in *Aegilops* was identified in the F2 population as being on the short arm of chromosome 4S. The mapping population was increased by backcrossing one $F_2$ line lacking B-type granules with the *Aegilops peregrina* parent line, which introgressed the Bgc-1 region into a background that is near iso-genic with *Aegilops peregrina*. Homozygous recombinant plants were selected from the backcrossed population and the original population, and were both phenotyped and genotyped. Genotyping included identification of SNPs using RNA sequencing of the parent plants. Markers were designed to these SNPs and fine mapping refined the location of Bgc-1 to a region near the telomere of chromosome 4S in *A. peregrina*.

Figure 4:
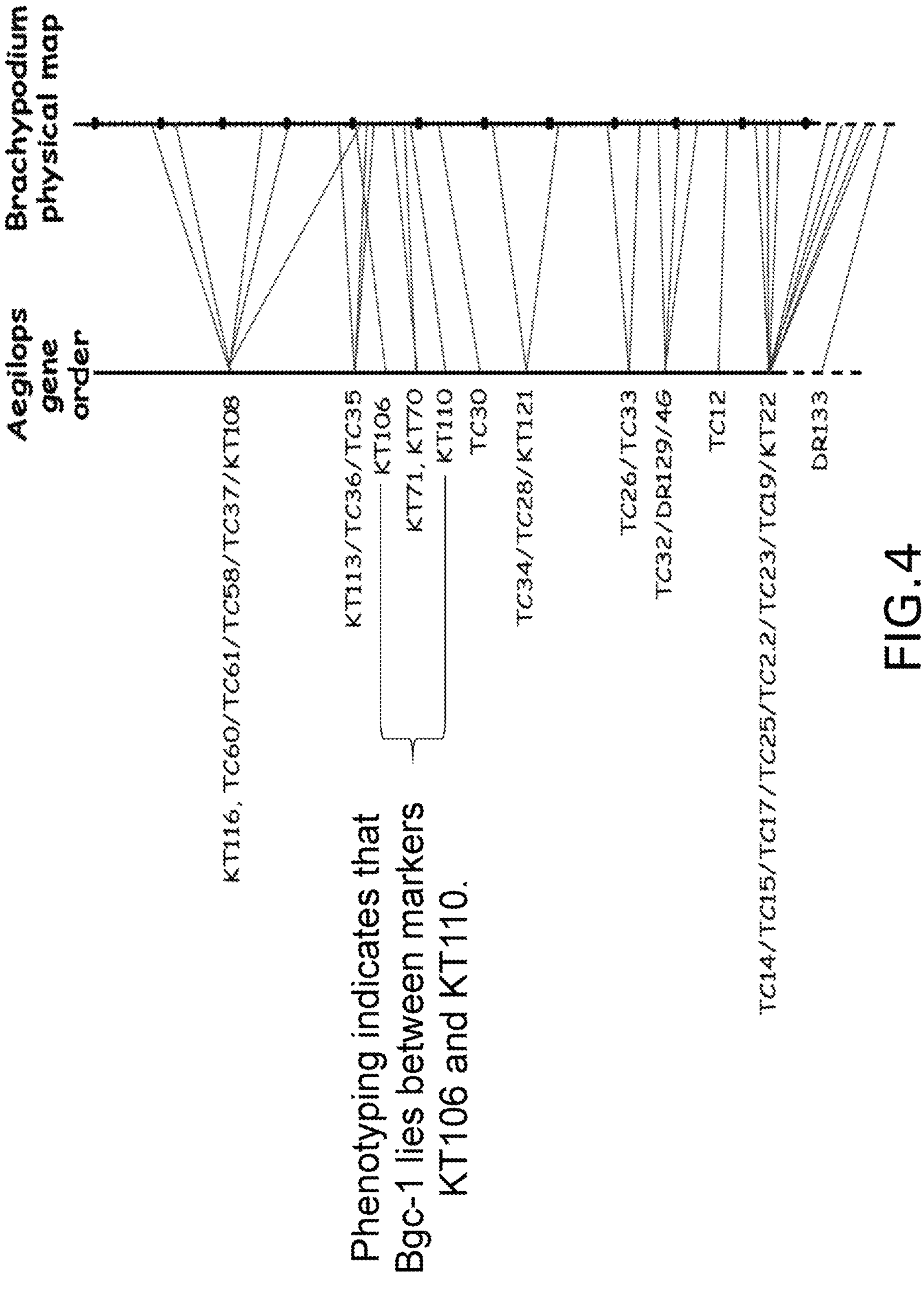
FIG. 4 shows the gene order in *Aegilops* (as determined from the mapping population) compared with that of *Brachypodium*. Markers DR129, 4G and DR133 were published in Howard et al., 2011. Phenotyping indicates that Bgc-1 lies between markers KT106 and KT110.

FIG. 4 shows results of the analysis conducted. Markers DR129, 4G and DR133 were published in Howard et al., 2011 supra. From this analysis, the markers flanking the Bgc-1 QTL marker gene were KT106 and KT110. These KASPar markers are designed to *Aegilops* genes which are orthologs of the *Brachypodium* genes BRAD11G12200 and BRAD11G12110, respectively. Comparison of this genome region with the genomes of sequenced and partly sequenced grass genomes *Aegilops tauschii, Brachypodium distachyon, Hordeum vulgare, Oryza sativa, Triticum aestivum, Triticum* uratu) reveals that the region contains ten conserved genes (Table 1).

One of the ten conserved genes (the gene amplified by marker KT71) was identified as a candidate Bgc-1 QTL marker gene (cBgc-1) by consideration of the functional annotations, patterns of gene expression, the lack of a functional protein encoded by the B-genome homoeologues in wheat, and allelic variation in protein sequence amongst *Aegilops* with and without B-type starch granules. The class of proteins encoded by Bgc-1 and its orthologues, encodes a proton-pumping ATPase located in the plasma membrane.

TABLE 1

Genes in the Bgc-1 region and their orthologues in other species. The markers found to flank Bgc-1 by mapping in *Aegilops* are shown in bold. The genes between the flanking markers in *Triticum aestivum* (A genome) and their orthologues in other species are as described in Ensembl Plants release 34 (ensemblgenomes.org).

| *Aegilops* marker | *T. aestivum* (A genome) | *Ae. tauchii* (D) | *T. uratu* (A) | *Brachypodium distachyon* | *Hordeum vulgare* (IPK) | *Hordeum vulgare* | *Oryza sativa* Japonica (RAP: Bd orthologue) |
|---|---|---|---|---|---|---|---|
| **KT106** | **TRIAE_CS42_ 4AL_TGACv1_ 288748_AA0957140** | **F775_06205** | **TRIUR3_ 17222, 3RIUR3_ 17223** | **BRADI1G12200** | **HORVU4Hr1G004470** | **MLOC_52290** | **OS03G0686900** |
| KT116 | TRIAE_CS42_ 4AL_TGACv1_ 288748_AA0957150 | F775_27418 | TRIUR3_ 17224 | Bradi1g12190 | HORVU7Hr1G018540 | MLOC_52153 | OS03G0687000 |
| | TRIAE_CS42_ 4AL_TGACv1_ 288748_AA0957160 | No orthologue | No orthologue | No orthologue | No orthologue | No orthologue | No orthologue |
| | TRIAE_CS42_ 4AL_TGACv1_ 290993_AA0991220 | No orthologue | No orthologue | No orthologue | No orthologue | No orthologue | No orthologue |
| TC35 | TRIAE_CS42_ 4AL_TGACv1_ 290993_AA0991230 | F775_12930 | TRIUR3_ 20887 | BRADI1G12180 | HORVU4Hr1G004440 | MLOC_56677 | OS06G0712500 |
| TC36 | TRIAE_CS42_ 4AL_TGACv1_ 290993_AA0991240 | F775_01647 | TRIUR3_ 20886 | BRADI1G12170 | no orthologue | MLOC_56679 | OS03G0687200 |
| KT121 | TRIAE_CS42_ 4AL_TGACv1_ 290974_AA0991080 | F775_28299 | — | BRADI1G12157 | HORVU4Hr1G004410 | MLOC_7897 | OS03G0688200 |
| | TRIAE_CS42_ 4AL_TGACv1_ 290753_AA0988980 | No orthologue | No orthologue | No orthologue | No orthologue | No orthologue | No orthologue |
| | TRIAE_CS42_ 4AL_TGACv1_ 288750_AA0957180 | F775_07147 | TRIUR3_ 22664 | BRADI1G12150 | HORVU4Hr1G004540 | — | OS03G0688300 |
| KT70 | TRIAE_CS42_ 4AL_TGACv1_ 288750_AA0957210 | F775_28757 | TRIUR3_ 02150 | BRADI1G12140 | HORVU4Hr1G004590, HORVU3Hr1G076320 | MLOC_3791 | OS03G0689100 |
| KT71 A1 | TRIAE_CS42_ 4AL_TGACv1_ 288750_AA0957220 | F775_14999 | TRIUR3_ 02152 | BRADI1G12117 | HORVU4Hr1G004820 | MLOC_52920 | OS03G0689300 |
| | TRIAE_CS42_ 4AL_TGACv1_ 290111 _AA0981830 | F775_23325 | TRIUR3_ 05747 | No orthologue | No orthologue | No orthologue | No orthologue |
| KT71 A2 | TRIAE_CS42_ 4AL_TGACv1_ 290111_AA0981820 | No orthologue | TRIUR3_ 05748 | BRADI1G12117 | No orthologue | No orthologue | OS03G0689300 |
| **KT110** | **TRIAE_CS42_ 4AL_TGACv1_ 290111_AA0981810** | **F775_02372** | **TRIUR3_ 05749** | **BRADI1G12110** | **HORVU4Hr1G004800** | **MLOC_54406, MLOC_71666** | **OS03G0689900** |

Deletion Mutants in Wheat

Deletion mutants were generated by T-irradiation (as described by Al-Kaff et al 2008, Annals of Botany 101:863-872) in the wheat cultivar Paragon (as part of the Wheat Genetic Improvement Network, WGIN project). This publically-available mutated population (M4 generation) was grown in 11-cm pots using ICL Levington Advance M2 Potting & Bedding compost) in a glasshouse with natural heat and light (during UK summer) or with 20° C. day and 15° C. night and lighting supplemented to give 16-h day length (during UK winter). DNA was prepared from seedling leaves using the methodology based on Fulton et al., 1995, Plant Molecular Biology Reporter 13:207-209.

Screening for Deletion Mutants

Figure 5:
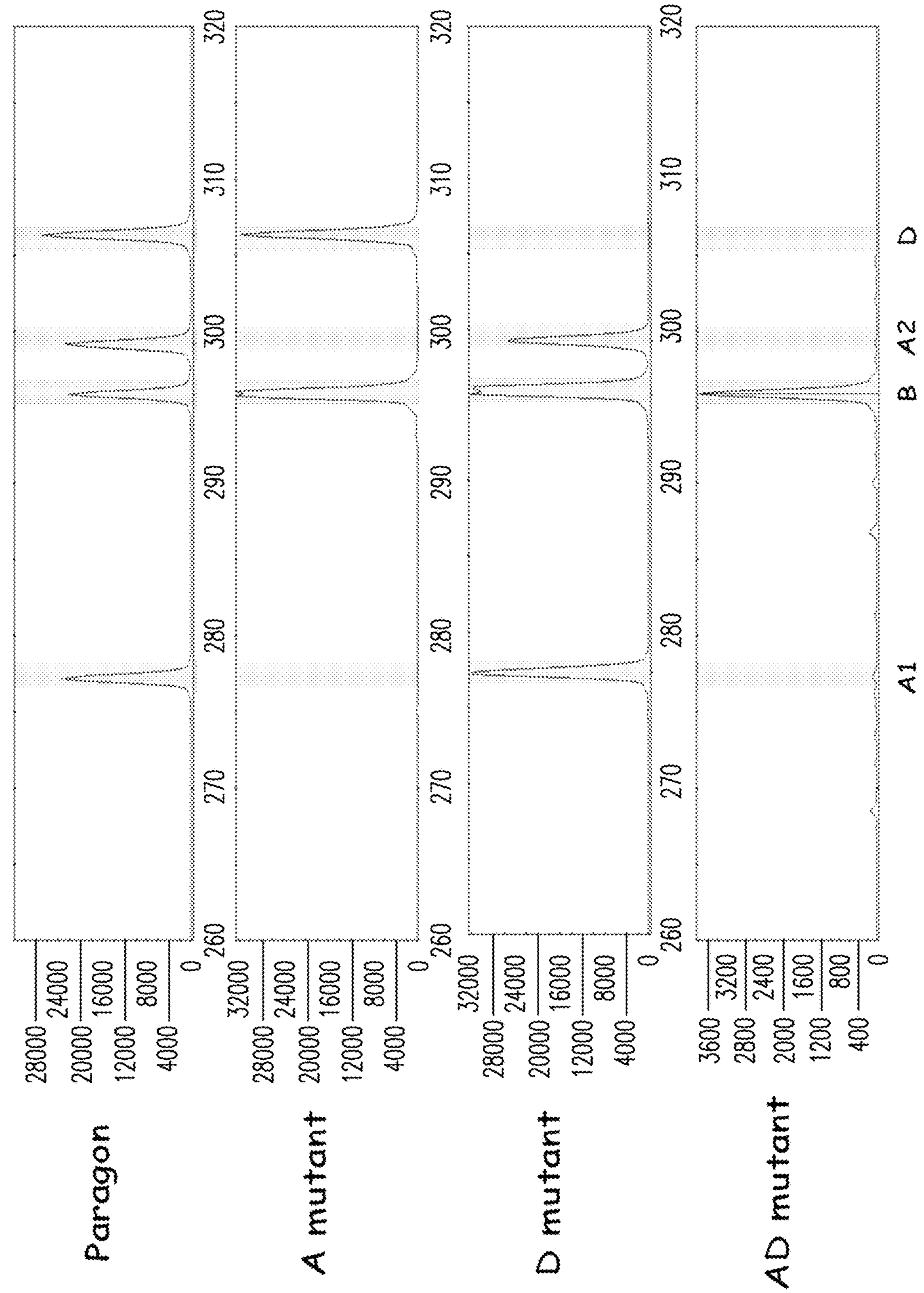
FIG. 5 shows a capillary electrophoresis electrophoretogram showing genotyping of a marker/candidate gene KT71 in wheat deletion mutants.

The deletion mutant population was screened for deletions in genes orthologous to those flanking the previously-identified *Aegilops* QTL for B-granule content on the short arm of chromosome 4S. Selection was conducted by genetic analysis of six genes (Table 1) one of which was later identified as the candidate Bgc-1 QTL marker gene, (amplified by marker KT71). Primers were designed to the six wheat genes. KT71 primers were designed to amplify all homoeologues whilst the other primers were designed to be homoeologue-specific. All the selected genes had three homoeologues except KT71 which had four. There are two copies of the KT71 gene on the A genome (genes A1 and A2), one on the B-genome (B) and one on the D-genome (D). The KT71 primers were designed to amplify fragments of the KT71 homoeologues that differed in size. The PCR products were separated by capillary electrophoresis as shown in FIG. 5. Plants lacking one or more of the four genes lack the corresponding PCR product(s) (identified by peak(s) on the electrophoretogram). Plants lacking A1 always also lack A2 suggesting that these two genes are encompassed by the same deletion on 4AL.

Some or all of the markers developed for all six genes shown in Table 2 were used to screen the Paragon deletion-mutant population. Deletion mutants of the A and D genomes were obtained and the genotype of the markers closely flanking cBgc-1 revealed the extent of the deletions (Table 3). All the deletions discovered were extensive, encompassing not only KT71 but also many of the flanking genes.

TABLE 2

PCR primers and conditions

Primers were designed to wheat genes. KT71 primers were designed to amplify all homoeologues whilst the other primers were designed to be homoeologue-specific. For 4N5.5, only a D-genome-specific primer pair was designed. Primer sequences and PCR conditions are shown. The primers are listed as SEQ ID Nos. 7 to 30 in the order shown below

| Aegilops marker | Chromosome | Wheat gene | Primer Forward 5'-3' | Primer Reverse 5'-3' | Amplicon size (bp) | Tm (° C.) | Extension time (s) | DMSO |
|---|---|---|---|---|---|---|---|---|
| TC37B | 4AL | 289950_ AA0979330 | AACTACAGAT TCATGACAGG | CTACTGCTAC CTCCTCTCTT | 85 | 60 | 30 | No |
| | 4BS | 328956_ AA1096100 | — | — | | | | |
| | 4DS | 361737_ AA1172310 | ACGGATTAGT CACAACAAGC | GTTGGGAAGA CAGATAATGC | 80 | 60 | 30 | No |
| KT71 | 4AL | 288750_ AA0957220 | GGARTTTGAT TTCCCGCCAT | [FAM]GCAGCCCA GAAGAAAATGACA | 279 | 59 | 30 | No |
| | 4AL | 290111_ AA0981820 | | | 301 | | | |
| | 4DS | 328355_ AA1086780 | | | 298 | | | |
| | 4DS | 361106_ AA1161080 | | | 310 | | | |
| TC30B | 4AL | 29007_ AA0981360 | ATCTGGTACCTGATT TCATAGTGA | CCACAACTGTACC ATTATCTACTGC | 265 | 60 | 30 | Yes |
| | 4BS | 328641_ AA1091570 | CAAGGACGCAAT CTCACCA | GCAACGAGGAGA TGAGCC | 506 | 60 | 30 | Yes |
| | 4DS | 361093_ AA1160690 | CAAGTTCTCTA CGGTTTGGAGT | TTGATCAAGAGA ATGGGGAT | 311 | 60 | 30 | Yes |
| TC34 | 4AL | 289509_ AA0972250 | ATGACACCTTT ATTTCAGCCAG | AGCTCGGTC TGCATTTGA | 639 | 62 | 30 | No |
| | 4BS | 328517_ AA1089200 | CGCTCACCATC ACCCAAG | GAGCTGAAGCGA ACGAAC | 283 | 62 | 30 | No |
| | 4DS | 362688_ AA1181550 | TGCCATCATCG GTAGTCATT | TGGTGTGCTGT TGATCCTT | 333 | 62 | 30 | No |
| 4G | 4AL | 289219_ AA0967530 | GATGAGCCGCC TCCCCAT | CCTTTGCTGA TGCAGTTCG | 304 | 60 | 30 | No |
| | 4BS | 362384_ AA1179360 | — | — | | | | |
| | 4DS | 362384_ AA1179360 | TGGAACACTGC CATCGTG | GGTGGAGCGAG ATATGAGATC | 311 | 60 | 30 | No |
| 4N5.5 | 4DS | 363571_ AA1183970 | GGCTTTGATAC TGGAACGAAT | CAGTGTAAGGC TCTGTTGCG | | | | |

For the wheat genes, the IDs given in Table 2 are preceded by:
TRIAE_CS42_[chromosome]_TGACv1_.

TABLE 3

Genotypes of the deletion mutant lines.
The markers are ordered (left to right) in the order in which they occur on the chromosome arm (telomere to centromere). PCR-positive (gene present) = '+'. PCR-negative (gene deleted) = '−'. PCR not determined = nd. PCR amplicon observed but low in abundance = FAINT.

| Chromosome arm | Line | Plant | Marker TC37b | KT71 | TC30b | TC34 | 4G | 4N5.5 |
|---|---|---|---|---|---|---|---|---|
| 4AL | A1 | 1 | − | − | − | − | + | nd |
| 4AL | A1 | 2 | FAINT | − | FAINT | − | + | nd |
| 4AL | A2 | 1 | − | − | − | − | − | nd |
| 4AL | A2 | 2 | FAINT | − | − | − | − | nd |
| 4AL | A2 | 3 | − | − | FAINT | − | − | nd |
| 4AL | A2 | 4 | − | − | − | − | − | nd |
| 4AL | A3 | 1 | − | − | − | − | − | nd |
| 4AL | A3 | 2 | − | − | − | − | − | nd |
| 4DS | D1 | 1 | − | − | FAINT | − | + | nd |
| 4DS | D1 | 2 | − | − | FAINT | − | + | nd |
| 4DS | D2 | 1 | − | − | − | − | + | nd |
| 4DS | D3 | 1 | − | − | − | − | − | − |
| 4DS | D4 | 1 | − | − | − | − | − | − |
| 4DS | D4 | 2 | − | − | − | − | − | − |
| 4DS | D4 | 3 | − | − | − | − | − | − |
| 4DS | D4 | 4 | FAINT | − | − | − | − | − |
| 4DS | D5 | 1 | + | + | + | + | − | + |
| 4DS | D5 | 2 | + | + | + | + | − | + |
| 4DS | D5 | 3 | + | + | + | + | − | + |

Stacking the Deletion Mutants

Stacking was conducted (by repeated rounds of crossing and selection) to incorporate multiple suitable deletions into a single plant.

Stacking of the A and D deletions by crossing was accomplished to produce double A/D mutant plants (derived from four $F_2$ plants).

Examination of the starch granules of the A/D double deletion mutant plants showed that they lacked B-type starch granules. Thus, the B-genome copy of Bgc-1 is postulated to be dysfunctional in these wheat plants.

Specifically, to generate plants with deletions in the Bgc-1 regions of both the A- and D-genomes, mutant lines A1-3 were crossed pairwise to lines D1-4, in all combinations. All crosses were successful except A2×D3. The $F_1$ plants were grown and allowed to self-fertilize. For each $F_2$ family, 24 grains were sown. DNA was prepared from seedling leaves and was PCR-screened using the KT71 primers only. Out of a total of 457 $F_2$ plants that were successfully screened, only one plant carried homozygous deletions on both 4AL and 4DS (FIG. 5). This double-deletion mutant plant derived from a cross between lines A1 and D4. The expected proportion of double mutants in the $F_2$ is 6%. The observed proportion of double mutants in the $F_2$ was 0.2%. The $F_2$ plants with single homozygous deletions on either the A- or D-genomes were also under-represented in the population. This suggests that the deletions are deleterious and that chromosomes carrying these large deletions are transmitted from one generation to the next with a lower frequency than wild-type (non-deleted) chromosomes.

To screen for additional double-deletion mutant plants, selected $F_2$ plants with homozygous single deletions on either 4AL or 4DS were allowed to self-fertilize and the $F_3$ seeds were each cut in half. Plants recovered from the embryo-halves of the $F_3$ seeds were screened for deletions using the KT71 primer pair. Four additional double mutant plants were discovered. Only one of the additional double mutants survived and was fertile. This second double mutant plant, like the first double mutant, derived from a cross between mutant lines A1 and D4. The first double mutant and its progeny only, were used in subsequent experiments.

Thus, two double-deletion mutant lines survived. These were derived from crosses between the same A and D genome deletions (A1×D4) but from different F1 plants. The mutant lines are therefore independent and this suggests that it is the combination of deletions of Bgc-1 regions on 4AL and 4DS rather than the combination of loci on other chromosome arms (background deletions) that is responsible for the lack of B-granules in the B-less mutants.

To screen for a wildtype segregant control line for the first 4AL/4DS double deletion mutant plant, the PCR-positive $F_2$ plants (wildtype or heterozygous for the deletion) from the A1×D4 $F_1$ plant that gave rise to the first double deletion mutant were grown and allowed to self-fertilize. An $F_2$ plant which gave progeny that were all PCR-positive (i.e. homozygous wildtype for the deletion) was selected.

Phenotypes of Single and Double Mutants

Granule analysis was conducted by microscopic examination. Howard et al., 2011 supra described suitable techniques for granule examination.

Figure 6:
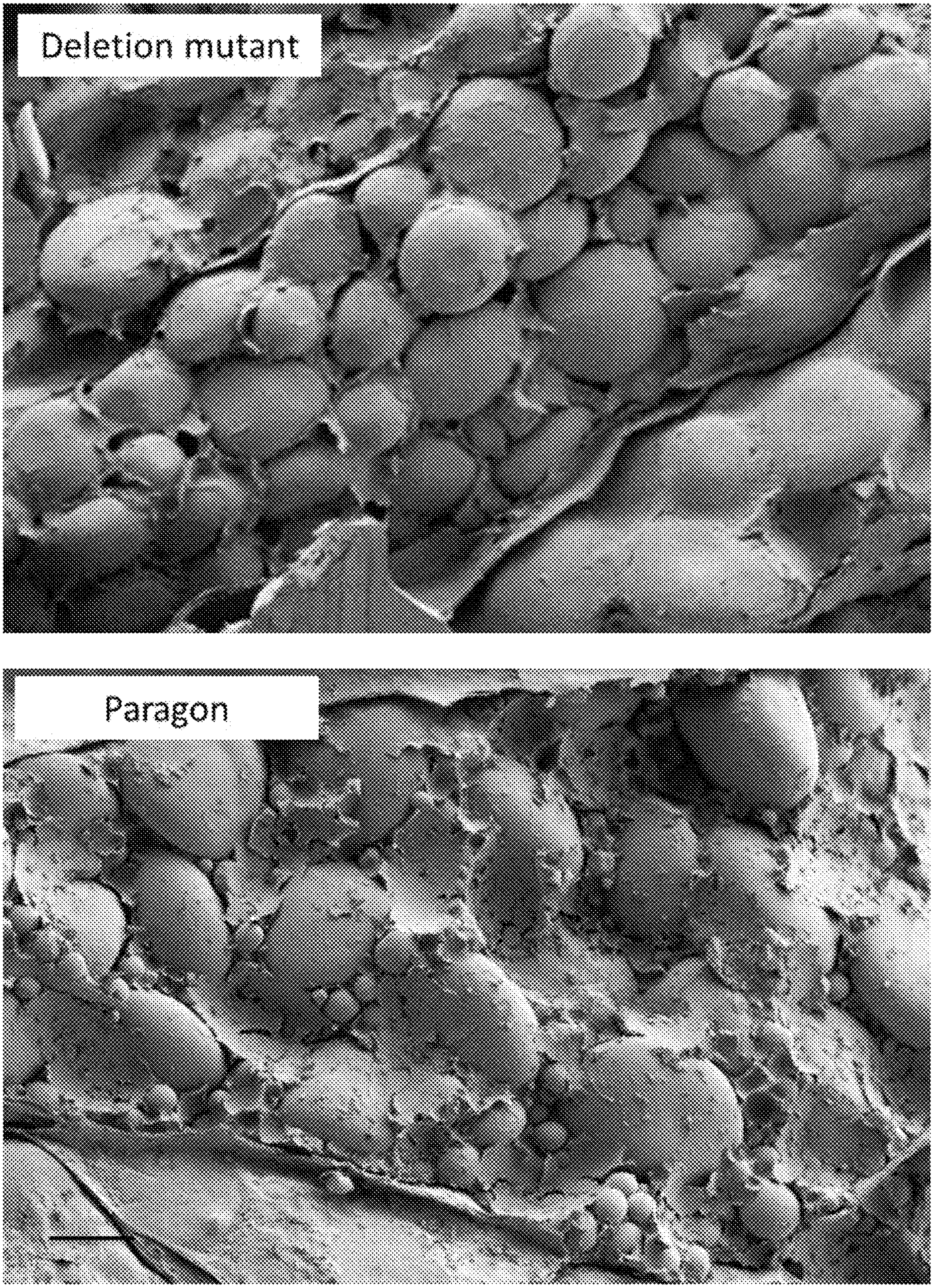
FIG. 6 are scanning electron micrographs showing the two starch-granule morphologies present in the wheat double mutant grain (lacks B-type granules) and the wheat parent cultivar Paragon (has both A- and B-type starch granules).

The starch granules from the single deletion mutants were examined microscopically and, like the normal wheat cultivar Paragon, all were found to possess A- and B-type granules (see FIG. 6). Starch from the control (wild-type segregant) also had both A- and B-type granules (data not shown). Starch from the double A/D mutant line however, was clearly abnormal in that it lacked small B-type starch granules when examined by light microscopy or SEM (see FIG. 6). The starch granules in the non-embryo halves of the four additional double mutant plants discovered in the $F_3$ screen were also found to lack B-granules. This shows that stacking deletions of the Bgc-1 regions of both chromosomes 4AL and 4DS in the same plant prevents the formation of B-type starch granules in wheat.

The progeny of the double mutant (B-less) plant were grown together with replicate wildtype segregant (Control) and Paragon plants. The height of the primary tillers of both the Control and B-less plants was statistically significantly less than that of Paragon. However, there was no difference in tiller height between the Control and B-less plants.

Grain weight, length, width and area were compared between the three genotypes. As with Paragon tillers, the Paragon grains were bigger than either the Control or B-less mutant grains. (However, the difference in grain weight between Paragon and the Control was not statistically significant). There was no difference in grain size or weight between Control and B-less mutant grains. Similarly, the starch content of both Control and B-less plants was statistically significantly less than that of Paragon but there was no statistically significant difference in starch content between the Control and B-less plants.

This analysis suggests that the background deletions in both Control and B-less plants are deleterious for plant growth. However, the lack of B-type starch granules due to deletions in the Bgc-1 region specifically, has no detectable effect on plant growth, grain size or starch content.

Starch was purified from the grains of the three genotypes: Paragon, Control and B-less mutant. Several starch functional properties were examined and for the following, there were no differences between the Control and B-less starches: protein content, moisture content, the size of the A-type starch granules and most of the DSC parameters (enthalpy of starch gelatinization, onset and peak temperatures). However, some functional properties were different between the Control and B-less starches. These included grain hardness (B-less were softer), small granule content (small starch granules are defined as those between 1 and 10 μm in diameter; B-less had fewer granules less than 10 μm in diameter), size of the small granules (B-less had larger small-starch granules, on average), amylose content (B-less had slightly lower amylose content), swelling power (B-less starch swells more) and finally, the DSC end temperature for the starch gelatinization peak (B-less end temperature was approximately 1.5° C. higher).

The lack of B-type granules was obvious when starch from mature grains was examined microscopically and was confirmed by quantitative analysis of starch-granule size distribution using image analysis. Image analysis showed that there are some small granules (with diameters between 1 and 10 μm) in the B-less mutant. This is also the case in the B-less *Aegilops* examined previously using a similar method. We assume that these small granules in the B-less mutant are small A-type granules rather than true B-type granules and this assumption is supported by the fact that the average size of this category of granules is larger in the B-less starch than in the wild-type Control.

Starch from B-less wheat grains has different functional properties than Control starch with B-granules. To some extent this is predicted from published data on the properties of purified A and B-type granules from normal wheat and barley, which can vary (Lindeboom et al, 2004, Starch 56, 89-99). However, the precise differences observed in our B-less mutant starch are mainly not as predicted. First, the amylose content of purified A-type granules has been found to be either greater (Peng et al, 1999, Cereal Chemistry 76:375-379; Takeda et al, 1999, Carbohydrate Polymers 38:109-114) or the same (Evers et al, 1974, Starch 26: 42-46; Myllarinen et al, 1998, Journal of the Institute of Brewing, 104: 343-349) as that of purified B-type granules. Thus, the amylose content of the B-less wheat starch might be predicted to be higher or the same as that of the Control. However, we observed a slightly lower amylose content. Second, the swelling power of B-less mutant starch is predicted to be lower than normal (Wei, 2010, Acta Physiologiae *Plantarum* 32:905-916; Chiotelli et al, 2002, Cereal Chemistry 79:286-293) but surprisingly was observed it to be higher. These data suggests that the A-type granules in the B-less mutant wheat differ in composition from the A-type granules in normal wheat.

The gelatinization enthalpy of B-less mutant starch was found to be the same as that of Control starch. The values obtained are within the range expected for wheat starch (7-10 J/g solids). This result is predicted by the work of Eliasson et al (1983, Physicochemical behaviour of the components of wheat flour. In: Cereals in breadmaking: a molecular colloid approach) which showed that the gelatinization enthalpy of wheat starch is independent of the granule-size distribution. However, others have found higher gelatinization enthalpies for A-type than for B-type starch granules in wheat (Peng et al., 1999, supra; Chiotelli et al, 2002, supra).

The deletion mutant plants (both Control and B-less mutant) grew less well than Paragon. The WGIN Paragon deletion mutant population is known to harbour many large deletions. This inhibition of growth is likely to be due to deletions of genes at locations in the genome other than the Bgc-1 region (background deletions). If the Bgc-1 gene was specifically manipulated, then B-granules could be eliminated without any (or with far fewer) side effects on plant growth.

The lack of any detectable decrease in grain weight or size suggests that yield of the B-less mutant may not be adversely affected. This together with the novel functional properties, indicate that B-less wheat is commercially useful. For example, uniform and on average larger-than-normal starch granules may lead to improvements in the yield of purified starch and gluten. Reduced grain hardness could lead to reduced milling energy. Increased swelling power could lead to increased bread softness and prolonged shelf life (reduced staling). B-granules are also predicted to be detrimental for malting and distilling suggesting that B-less wheat may be preferred for alcohol production.

Further details are set out below in Table 4.

TABLE 4

Growth metrics and starch functional properties. All values are expressed as mean ± SE per plant. The number of plants measured = n.

| | Normal (Paragon) | | | Control (wild-type segregant) | | | B-less mutant | | | Student's t-test (p value) Normal v | | | Mutant |
|---|---|---|---|---|---|---|---|---|---|---|---|---|---|
| | | | | | | | | | | Normal v | Normal v | Mutant v | different from control |
| | Mean | n | SE | Mean | n | SE | Mean | n | SE | Control | Mutant | control | ($p < 0.05$) |
| Growth metrics | | | | | | | | | | | | | |
| Height of primary tiller (cm) | 80.86 | 18 | 1.55 | 72.50 | 8 | 3.75 | 65.08 | 12 | 2.37 | 0.02 | 0.00 | 0.09 | No |
| Grain weight (mg) | 38.66 | 18 | 1.00 | 31.86 | 8 | 2.20 | 33.94 | 23 | 1.02 | 0.08 | 0.00 | 0.34 | No |
| Grain length (mm) | 6.24 | 18 | 0.04 | 5.64 | 7 | 0.15 | 5.73 | 26 | 0.05 | 0.00 | 0.00 | 0.51 | No |
| Grain width (mm) | 3.34 | 18 | 0.04 | 3.04 | 7 | 0.10 | 3.19 | 26 | 0.04 | 0.00 | 0.01 | 0.11 | No |
| Grain area ($mm^2$) | 17.03 | 18 | 0.29 | 14.01 | 7 | 0.73 | 14.75 | 26 | 0.24 | 0.00 | 0.00 | 0.22 | No |
| Starch content (% grain weight) | 64.8% | 4 | 1.1% | 57.8% | 4 | 2.0% | 52.0% | 4 | 1.8% | 0.02 | 0.00 | 0.08 | No |
| Starch functional properties NIR | | | | | | | | | | | | | |
| Protein content | 16.44 | 6 | 0.48 | 18.59 | 3 | 0.64 | 17.66 | 5 | 1.19 | 0.03 | 0.34 | 0.59 | No |
| Moisture content | 12.25 | 6 | 0.06 | 11.82 | 3 | 0.17 | 12.15 | 5 | 0.11 | 0.02 | 0.44 | 0.14 | No |
| Hardness | 68.45 | 6 | 2.09 | 63.33 | 3 | 1.76 | 39.62 | 5 | 4.21 | 0.16 | 0.00 | 0.01 | Yes |

TABLE 4-continued

Growth metrics and starch functional properties. All values are expressed as mean ± SE per plant. The number of plants measured = n.

| | Normal (Paragon) | | | Control (wild-type segregant) | | | B-less mutant | | | Student's t-test (p value) Normal v Control | Normal v Mutant | Mutant v control | Mutant different from control ($p < 0.05$) |
|---|---|---|---|---|---|---|---|---|---|---|---|---|---|
| | Mean | n | SE | Mean | n | SE | Mean | n | SE | | | | |
| Granule size | | | | | | | | | | | | | |
| Small granule content (% granules 1-10 um diameter) | 53% | 4 | 4% | 55% | 4 | 4% | 17% | 4 | 5% | 0.78 | 0.00 | 0.00 | Yes |
| Size of small granules ($\mu m^2$) | 25.54 | 4 | 0.66 | 23.50 | 4 | 0.64 | 38.64 | 4 | 5.26 | 0.07 | 0.05 | 0.03 | Yes |
| Size of large granules ($\mu m^2$) | 317.8 | 4 | 6.6 | 294.5 | 4 | 15.1 | 349.3 | 4 | 23.6 | 0.21 | 0.25 | 0.10 | No |
| Amylose content (% starch) | 23% | 4 | 1% | 25% | 4 | 1% | 21% | 4 | 1% | 0.26 | 0.07 | 0.01 | Yes |
| Swelling power ( ) | 9.12 | 4 | 0.27 | 9.09 | 4 | 0.32 | 11.37 | 4 | 0.39 | 0.94 | 0.00 | 0.00 | Yes |
| DSC | | | | | | | | | | | | | |
| Enthalpy of Starch Gelatinisation | 8.13 | 3 | 0.11 | 8.20 | 3 | 0.03 | 7.96 | 3 | 0.47 | 0.58 | 0.74 | 0.63 | No |
| Onset temperature (° C.) | 57.49 | 3 | 0.42 | 57.25 | 3 | 0.28 | 56.67 | 3 | 0.09 | 0.66 | 0.13 | 0.12 | No |
| Peak temperature (° C.) | 61.79 | 3 | 0.48 | 61.82 | 3 | 0.24 | 62.34 | 3 | 0.40 | 0.96 | 0.43 | 0.33 | No |
| End temperature (° C.) | 69.34 | 3 | 0.76 | 70.34 | 3 | 0.38 | 71.74 | 3 | 0.21 | 0.30 | 0.04 | 0.03 | Yes |
| Enthalpy of melting of the amylose-lipid complex | 0.39 | 3 | 0.02 | 0.46 | 3 | 0.04 | 0.67 | 3 | 0.06 | 0.24 | 0.01 | 0.04 | Yes |
| Onset temperature (° C.) | 98.53 | 3 | 0.19 | 98.72 | 3 | 0.29 | 97.52 | 3 | 0.18 | 0.60 | 0.02 | 0.02 | Yes |
| Peak temperature (° C.) | 103.52 | 3 | 0.27 | 103.89 | 3 | 0.22 | 103.26 | 3 | 0.19 | 0.35 | 0.47 | 0.09 | No |
| End temperature (° C.) | 108.02 | 3 | 0.31 | 108.79 | 3 | 0.25 | 108.28 | 3 | 0.25 | 0.13 | 0.55 | 0.22 | No |

Table 5 below gives the markers on chromosome 4S of *Aegilops*, and their corresponding genes in wheat used to identify the Flo6 gene in wheat.

RNA sequencing (RNAseq) of grains and leaves of the two parents, *A. peregrina* and KU37 was used to develop molecular markers for fine mapping. KASP assays Igc-group.com were designed to sequence differences between the sequences of the parents and tested on a sub-set of the population to identify markers linked to Flo6.

TABLE 5

| Aegilops marker | Primer (VIC) | Primer (FAM) | Primer common | Wheat 4BS Orthologue |
|---|---|---|---|---|
| | VIC tag = GAAGGT CGGAGTCAACGGATT SEQ ID NO: 62 | FAM tag = GAAGGT GACCAAGTTCATGCT SEQ ID NO: 63 | | |
| TC60 | TCGTCGCCATGGAGGA Gg SEQ ID NO: 64 | TCGTCGCCATGGAGGA Ga SEQ ID NO: 65 | AGGACCAAA GACCGGGCG SEQ ID NO: 66 | Traes CS4B01G025500 |
| TC61 | ACAGTCTCCTAGGCGT CTGc SEQ ID NO: 67 | ACAGTCTCCTAGGCGT CTGa SEQ ID NO: 68 | CTACCAGCAGG AGAATAGGATC SEQ ID NO: 69 | Traes CS4B01G025600 |
| TC58 | AGTTGATACAGGTGCA GtTTa SEQ ID NO: 70 | AGTTGATACAGGTGCA GgTTC SEQ ID NO: 71 | CCATCTATTTG GCGGCAA SEQ ID NO: 72 | Traes CS4B01G026000 |
| KT108 | GGGAGATTGTGGTTAT CTGGAAc SEQ ID NO: 73 | GGGAGATTGTGGTTAT CTGGAAt SEQ ID NO: 74 | CAGCTGACTTCA ATTCATTTAGC SEQ ID NO: 75 | Traes CS4B01G027900 |
| KT116 | GGAGATTGTGGTTATC TGGAAc SEQ ID NO: 76 | GGAGATTGTGGTTATC TGGAAt SEQ ID NO: 77 | CTGACTTCAATT CATTTAGCACTG SEQ ID NO: 78 | Traes CS4B01G027900 |
| KT113 | TCCGAgGTTCCAGAGC ACGg SEQ ID NO: 79 | TCCGAgGTTCCAGAGC ACGa SEQ ID NO: 80 | TGCTGTCAAGAT GATTGTATGGAG SEQ ID NO: 81 | Traes CS4B01G028900 |
| TC36 | GCAGACTCAAACAACT TGCTc SEQ ID NO: 82 | GCAGACTCAAACAGCT TGCTt SEQ ID NO: 83 | CAGCTTTCTGAA CTTGAGAGG SEQ ID NO: 84 | Traes CS4B01G029300 |

TABLE 5-continued

| Aegilops marker | Primer (VIC) | Primer (FAM) | Primer common | Wheat 4BS Orthologue |
|---|---|---|---|---|
| TC35 | ATGTTGCCGTTGTAGT GGAc SEQ ID NO: 85 | ATGTTGCCGTTGTAGT GGAt SEQ ID NO: 86 | AGCACGCGGAGA TCGACA SEQ ID NO: 87 | Traes CS4B01G029400 |
| KT106 | AGGATGGAACAATCAG AAGGc SEQ ID NO: 115 | AGGATGGAACAATCAG AAGGa SEQ ID NO: 116 | CTACCGGGATAC AACCTCAG SEQ ID NO: 117 | Traes CS4B01G029700 |
| KT117 | CTTCAAATAAATGGGG GCAc SEQ ID NO: 88 | CTTCAAATAAATGGGG GCAa SEQ ID NO: 89 | CCCAGTGGATGA GAATTTTC SEQ ID NO: 90 | Traes CS4B01G031000 |
| KT70 | GCATGTCTTTAAGA TATACATAAATaaa tAAAC SEQ ID NO: 91 | GCATGTCTTTAAGATA TACATAAATAAAC SEQ ID NO: 92 | AAGTAAGATGCCT TTCTGAAGTTCT SEQ ID NO: 93 | Traes CS4B01G030400 |
| KT110 | ATTTGGCATGCGGA ATGGCTc SEQ ID NO: 94 | ATTTGGCATGCGGAAT GGCTa SEQ ID NO: 95 | TTCATTCATACTT GATAATGCCC SEQ ID NO: 96 | Traes CS4B01G030500 |

Testing Candidate Gene TaFlo6

Despite the very different phenotype observed in barley and rice Flo6 mutants compared with that of B-granule-less *Aegilops* and Paragon deletion mutants, we selected Flo6 wheat TILLING mutants (wheat-tilling.com) in the tetraploid line Kronos (genome composition AB). An alignment of the wheat FLO6 protein seq is shown in FIG. 10 together with the sequences of the rice, barley and *Arabidopsis* FLO6 proteins Kronos lines with mutations in either the 4A or 4B Flo6 genes where chosen. The mutations chosen were ones which were likely to affect the function of the FLO6 protein i.e. they were nonsense (stop) or missense mutations. Both of the Kronos A-genome mutants (K2244 and K3145) have a premature stop codon in the coiled-coil domain. Kronos line (K3145) has an induced nonsense mutation (Trp400-STOP) that is in the same position as the mutation in the barley Flo6 mutant, Franubet (Trp396/STOP) (alignment in Supplementary). Two of the Kronos B-genome mutants (K3239 and K0456) have a missense mutation in the CBM48 domain.

Figure 11A:
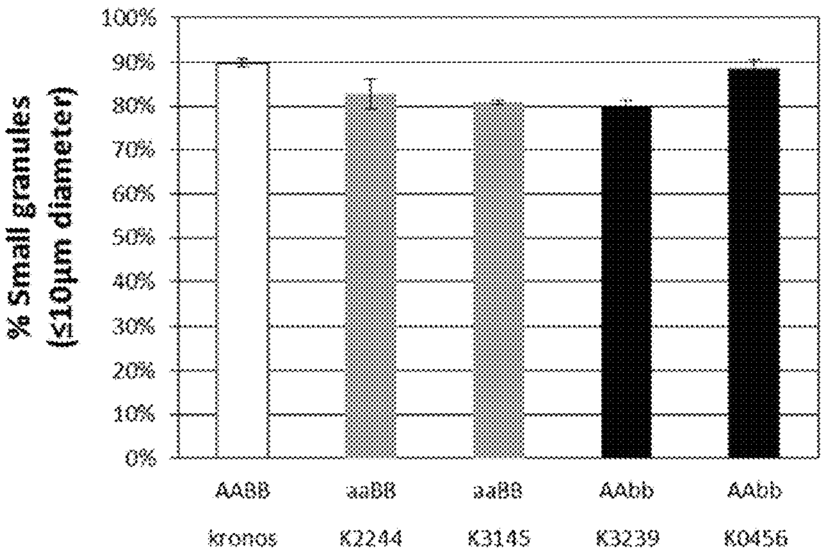
FIGS. 11A-C show data for Bgc-1 candidate gene 2. The proportion of small granules in starch from wheat TILLING mutants was examined. Starch was extracted from mature grains of Kronos and the B-granule-content was determined.
Figure 11B:
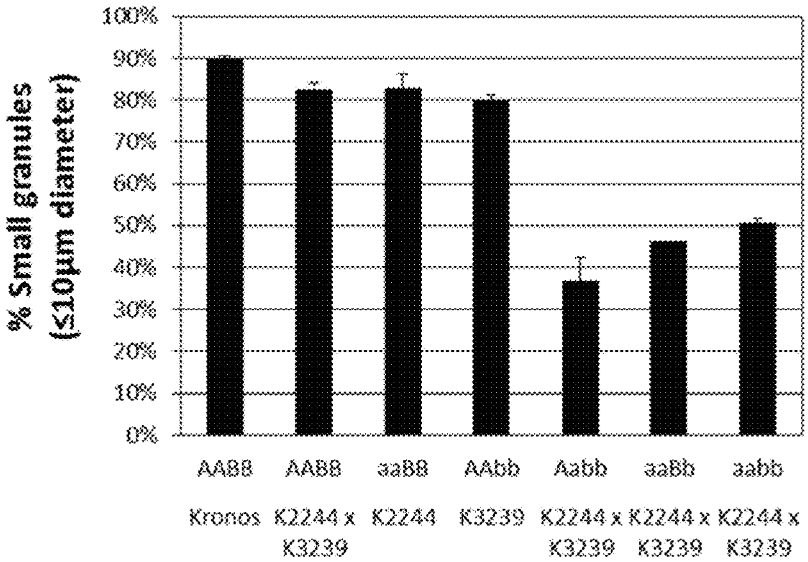
Figure 11C:
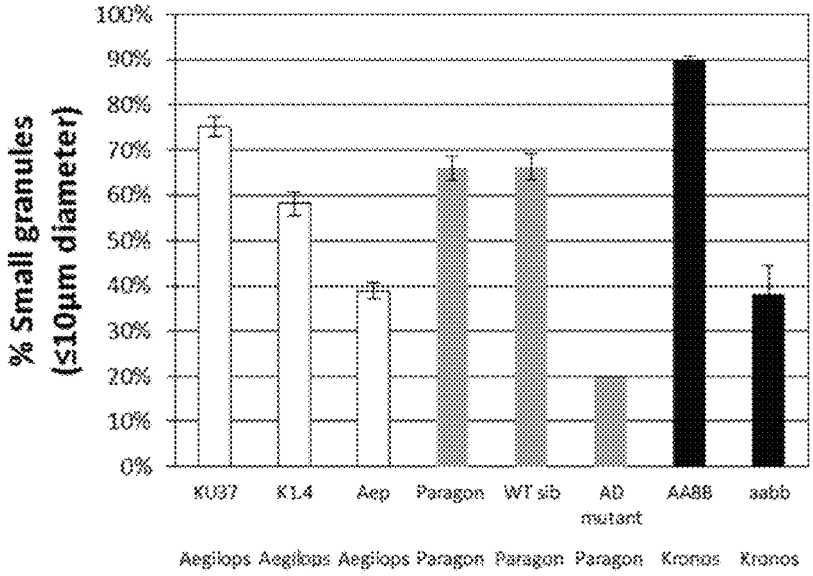

The supplied Kronos plants were grown and homozygous mutant plants selected. Starch from the single-mutant grains was observed microscopically. All lines showed a bimodal starch granule-size distribution. However, analysis of granule size distribution showed a small reduction in the proportion of small (B) granules in the two 4A nonsense mutants (K2244 and K3145) and in one of the 4B mutants (K3239) when compared with wild-type controls (FIG. 11A). Homozygous double mutant lines (and their corresponding wild-type segregant lines) were selected from a cross between the A-genome mutant, K2244 and the B-genome mutant, K3239. Starch from double mutant grain showed a drastic reduction in small-granule content (FIGS. 11B and 11C) similar to that seen for the Paragon AD double mutant and in *Aegilops peregrina* (FIG. 11C).

The Phenotype of Wheat Entirely Devoid of FLO6 Activity

The apparent discrepancy between the phenotypes of the Kronos double mutant (lacking B-granules) and Franubet barley (heterogeneous granule morphology) is not completely understood. Of the two single mutant lines used to generate the Kronos double mutant line, the B-genome line, K3239 was a missense mutant (Val470-Ile) which might not completely lack FLO6 activity. The A-genome parent line, K2244, has a nonsense mutation (Trp291-STOP) which is highly likely to prevent the production of any active FLO6. Franubet barley, on the other hand is diploid and has a nonsense mutation (W396-STOP; AK373583) which should eliminate all active FLO6. (The Franubet mutation is in the same relative position in the protein as the mutation in the K3145).

To test whether a total elimination of FLO6 activity in wheat would cause a phenotype similar to that in Franubet barley (i.e. heterogeneous starch granule morphology rather than a reduction in B-granules), the following experiments could be done. 1) Creation of a TaFlo6 triple mutant hexaploid wheat line, by crossing the Paragon double deletion mutant to a Cadenza TILLING mutant which has a nonsense mutation in Flo64B (such as line Cadenza1730). A triple mutant could be selected from the progeny of this cross. 2) A TaFlo6 triple mutant of Cadenza could be created by crossing suitable single tilling mutants together and selecting a triple mutant from the progeny of the cross.

The Effect of Flo6 Gene Dosage on Starch Granule Phenotype in Wheat

We found that the single mutants of Kronos wheat had slightly reduced numbers of B-granules compared to Kronos (FIG. 11A). This indicated that there may be a dosage effect of the Flo6 gene of B-granule content.

Using the Kronos TILLING mutants, we looked at B-granule content in individual grains with different gene dosages. This was done by taking grains from a plant that was heterozygous for at least one genome-copy of TaFlo6, cutting the grains in half, germinating and genotyping the embryo half-grain and extracting and phenotyping the starch from the non-embryo half-grain. This showed that gene dosages of less than 50% wildtype gave drastically reduced numbers of small granules (corresponding to zero B-granules) whereas gene dosages equal to or more than 50% Flo6 gave near-normal small-granule content (FIG. 11B).

Figure 12:
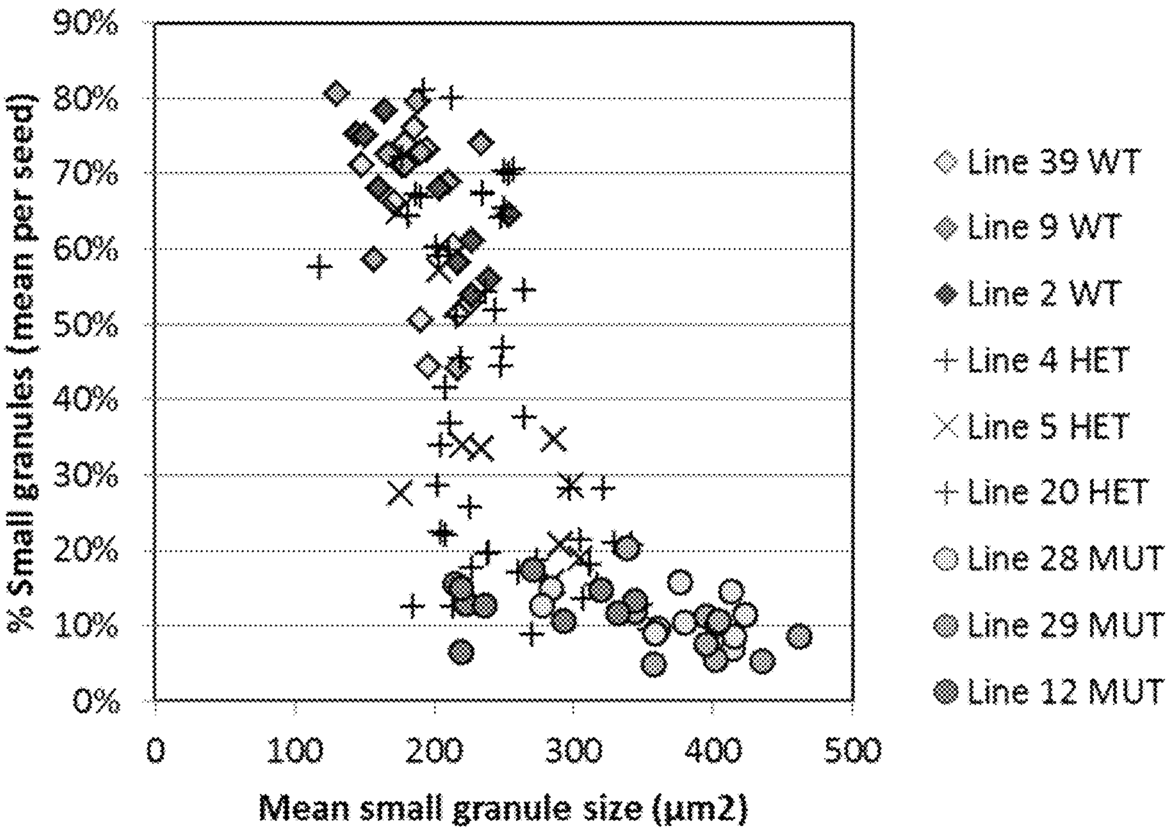
FIG. 12 shows data for Bgc-1 candidate gene 2, namely Flo6. The gene dosage effect on B-granule content in Paragon hexaploid wheat was examined. We previously identified Paragon hexaploid wheat deletion mutant lines with deletions of the Bgc-1 regions of chromosomes 4A and 4D. These single mutants had normal B-granule content. A double deletion mutant (aaBBdd) was isolated and found to lack B-granules (Chia et al., Journal of Experimental Botany 68: 5497-5509 (2017)). Here we analysed the B-granule content of the progeny (numbered lines) of another plant from the cross which was heterozygous for the A-genome deletion (AaBBdd). The genotypes of the lines shown are WT, AABBdd; HET, AaBBdd and MUT, aaBBdd.

We noticed that the phenotype of some grain from the Paragon deletion mutant population was intermediate between that of the wildtype (normal B-granule content) and that of the Paragon AD double mutant (B-granule-less). An $F_2$ plant from the Paragon deletion mutant population (generated by crossing the A- and D-genome single mutants) was studied. This plant was homozygous mutant for the 4D-genome deletion but segregating for the 4A-genome deletion (AaBBdd). The genotype of the progeny of this plant was assessed from phenotype of their grains as follows: three A-genome wildtype plants (AABBdd) were identified with grains that all had normal B-granule content; three mutant plants (aaBBdd) were identified with grains that all lacked B-granules and three heterozygous plants (AaBBdd) were identified with grains that varied in B-granule content. The B-granule content of individual grains from these nine plants is shown in FIG. 12. The grains from the 3 heterozygous plants, which should themselves be segregating the A-genome deletion, varied in % small granules. Some grains had wildtype % B granule values, some had mutant % B-granule values and some had values intermediate between those of the wildtype and the mutant. We reasoned that the grains with intermediate phenotype must be heterozygous grains having the genotype AaBBdd (heterozygous for the 4A-genome deletion, homozygous wildtype for the 4B-genome and homozygous mutant for the D-genome deletion). If so, this suggests that hexaploid wheat grains with a 50% normal Flo6 gene dosage (AaBBdd) have fewer B-granules than grains with 66% gene dosage (AABBdd) and more B-granules that grains with 33% gene dosage (aaBBdd).

All documents referred to herein are incorporated by reference. Any modifications and/or variations to described embodiments that would be apparent to one of skill in art are hereby encompassed. Whilst the invention has been described herein with reference to certain specific embodiments and examples, it should be understood that the invention is not intended to be unduly limited to these specific embodiments or examples.

The following are the genomic Bgc-1 DNA (A, B and C) and amino acid (D, E and F) sequences for *Aegilops* with B-type starch granules (KU37) and without B-type starch granules *Aegilops peregrina* and *Aegilops crassa*). The divergent nucleotides (A, B and C) and amino acids (D, E and F) are highlighted. A and D; B and E: *Aegilops peregrina*; C and F: *Aegilops crassa*. The position of amino acid changes are shown in bold and boxed. These sequences are followed by the genomic Flo6 DNA for genomes A, B and D (labelled G, K and L respectively) and their amino acid sequences (H, K and M respectively).

A

>Ku37seq_clonesD2&D3

(SEQ ID No. 1)

CAAGACCATACGTACACATAAATAAATCAGTAAATCATAAAGAAGAAGAAGAAGAAGAGCAG

AGGAGGAGGGTCCAGAAGAGTAGTTGGCGGTGGGAAGATCCAGAGGCTGCGCACTGCCTGCC

CGGCCGCCTCCACGGCCATGGCCAGCAGCAGGCAGGAGGGGAACCTCGACGCCGTCCTCAAG

GAGGCCGTCGACCTGGTAATCACTCAGTTCATCAATCAACTCCCTGCTCTTGGGGTAGTATA

GTGCTTCCTCTCTGGTTTTTAGTTAGCGTTGCGCTTCTTGGGGAAATCACCATGTGGCTCGG

CCGTCGGCCGCTGGGGTTTCTTTCCGCGCTTCGGGCGTCGCAGTTGCATTGCAGGGTGGTGG

AGTTGGCCTGCCAGCGCCTCTTCTTGTAGGTCAATTTGGGAGCGTCGATCTCCCTCCCCTGC

CTAGTGTACCGCACTGCTCTAAAATCTCACCCCCCAAATCTTACTAAGCAAAATTTCACCCA

GGCTACAACTTTGAGCTACTATTTTTTCCCAGGGCTTACAAAAACTGCAGTTTAGTTTTAAA

TTTTAAAATCTCGCAGTTTTATATATAGCTTTGATTTTTCTTTTGTCTGGACAGCGTGTGAG

GGCTGCTTGTAAATGTATTTGCTCTAGCTTCGGATTATTTTGATTTTTCTTTTGTCTGGACA

GTGTATGAGGGCTGATCACAAGAAGTACATACTTTTTCCTCTGTTTGATTAGAATTTTTATG

ATCCTCTGTTTGATTAATTTTTTTTTTTTGTCTCTTGGTTCTCTCTTCTGGGTTCCTTAGAG

TAGCAGGCTGCAGCTAGCATACTTGCTCGTTCAGATTTTGCTCATGCTAATGGTACTTGTTT

GGTTTTGTTAAAAGAGATTGCCGTAACAAAATTTCAGGAGCACATCCCAATTGATGAAGTGT

TTGAGAACCTTCGGTGCAGCCACGAGGGGCTCGCTTCCGAGCAGGCGCAGCAGCGGCTACAG

ATCTTTGGCCCGAACAAGCTCGAGGAGAAGGAGGTCAGGTTCTTTCAGCCCATTTGATTATG

GGGAAGATTTTGTCCTTGCTCTTCTTGAGAGCAGTAATGTTCTTCTCATTGATGTTATGCAC

TTGAGTAAGTTGGAGTGTTTGATGGCTGCAGGAGAGCAAGTTCCTCAAGTTTCTGGGGTTCA

TGTGGAATCCACTGTCATGGGTCATGGAGGCTGCGGCGATCATGGCCATCGCGCTGGCGAAC

GGAGGGGTAAGACCCAGCACATAGTATTGCAGAATTTGTGGTGATGAGTGATGTTGTATGTC

CTGCTCTGTTCTCAATATATATGTGGGATGTGTTCTGTCACCACCAGGGGAAGCCACCAGAT

TGGCAAGACTTTGTCGGTATCATCACGCTGCTACTTATAAACTCCACCATCAGTTTCATCGA

GGAAAACAATGCCGGAAATGCTGCCGCCGCGCTTATGGCACGTCTTGCGCCAAAAGCCAAGG

TCCATATATTCACTTAATTTGTGGCATTTCCCCTGTTTCTGCACGTATCACCTTGTTGGAGT

CCATTTTAATTTGTGAAACTCATTATTATATTGCTAAGTAGGTTCTCCGTGACGGTCGTTGG

-continued

ACCGAGGAGGAGGCAGCCGTCCTTGTGCCTGGGGACATCATCAGCATCAAACTTGGAGATAT

CATTCCTGCCGACGCCCGCCTCCTAGACGGCGATCCTTTGAAGATTGATCAGGTTTTTTCTG

TCCTTCACATCCGAGTCACCTTCAGCTTTGCTTTTACTTATTTAGATTTCCTATTTCCTCAT

CTCACTACTTGGTCTCTTATTTATAGTCTGCCCTGACTGGAGAATCGCTGCCAGCCACCAAA

GGTCCTGGTGACGGCGTCTACTCTGGTTCGACGGTCAAGCAGGGCGAGATCGAGGCTGTTGT

CATAGCAACTGGTGTGCACACTTTCTTTGGGAAGGCCGCACATCTCGTCGACTCCACCAACC

AAGTTGGCCATTTCCAACAGGCAAGCTTGACAAGCCTCGGATACTTTTATCGAATTGTATCA

TCGCTACATTGATGTTTTCATTATCATGCGATTGACGCAGGTGTTGACAGCCATCGGGAACT

TTTGCATTTGCTCGATTGGTGTGGGGATGTTCATAGAGATCATTGTCATGTATCCTATCCAG

CACAGGGCGTACCGCCCTGGGATCGACAACCTTTTGGTGCTTCTCATTGGAGGCATTCCCAT

AGCGATGCCCACAGTCTTGTCGGTCACCATGGCGATTGGGTCTCATCGCTTGTCTCAACAGG

TATGCATCATTCCAGGGACAGTGTCTCTTAACCATATTGTGACCAGACCTGAACTTCTGCAC

TATGCAATCAATTCCTGAGTTTTCTTCCTGCAGGGAGCTATAACAAAGAGAATGACTGCAAT

CGAAGAGATGGCCGGCATGGATGTTCTTTGCAGTGATAAGACTGGAACCCTGACTCTAAATA

AGCTCAGCGTGGACAAGAACCTAATCGAGGTAAGGTTCACTTGAACACTCACTTTTTGTTAT

CTCATATGTAACCTCAGAGCACTTACATACTTTTTTGGTGCAGGTTTTTGAAAAAGGAGTG

ACTCAGGACCAGGTGATTCTGATGGCTGCTAGAGCATCCCGGATAGAAAATCAAGATGCCAT

TGATACGGCGATTGTTGGGATGCTAGGCGATCCAAAAGAGGTACATTGATTTGTCGAATAAT

GAGACGTACAGCTATCACGTTTATTTGCTAAAATGGATACCTGTTAACTCTCCCCGTAGGCG

CGTGCCGGTATTCAAGAGGTTCACTTTCTGCCGTTCAATCCTACCGACAAAAGAACCGCGTT

GACATACATTGATGGCGATGGAAAGATGTACCGTGTTAGCAAAGGTGCACCAGAGCAGGTAT

AATCTTTTTTTACTGCAAAAAGCTTAAAAAACATTTGCATAATGATGTAAATTGATTTCACA

AATTGACCTGCAGATTCTTAACCTGGCCTACAACAAGTCAGAGATCGCACAAAAAGTCCACA

CTGTCATCGACAAGTTCGCGGAACGTGGACTTCGGTCACTTGGTGTAGCATATCAGGTGAGA

AAGGTTCTGGGTGTGCCCCTTCACAGTGCAGTTGAAGCTTGCAAGGCAGGAACTTAGTGGTG

GTCATTCTTTTCTGCCTTGTAGGACGTGCCAGATAGGAGGAAAGAGAGCCCGGGTAGCCCGT

GGCATTTTGTTGCTCTCTTGCCACTCTTTGATCCACCGAGGCACGACAGCGCAGAAACAATT

CAAAGGGCACTTAACCTTGGTGTGAATGTGAAGATGATCACAGGTACACTGCCAATTGGGTT

GTTACTACTTTTTTGCTCTGTTCTTAAATATCCAATTCGATGAAGATGATCACAAGTAAATG

CACTACCGGTTGAATTCTATTTTGTTCTCTTCTCTCTATTCTTAAATCTCCCAATTTTTATG

AGCACCATGTCTTTGATGTTTACTATTTTTTATTTGTGATGTCATGTAAGGACCCCTTAAAA

AGCTGTGCCATAAGTAGAGTTGGAACATTGAACATATGCTGTATCTTATCTTGTTTTATTAT

AATTTCAGTTTCAATAATTTTGGTAATACATCTTATTGTGCTTTTCCCCCCTAAGGCGACCA

GCTAGCGATTGGGAAGGAAACAGGGCGTCGTCTAGGAATGGGTACAAACATGTACCCATCAT

CTGCTTTGCTGGGGCAGAACAAGGATGAGTCTATTGCTGATTTACCAGTCGATGATCTAATT

GAGAAAGCCGATGGTTTTGCTGGCGTATTCCCAGGTATGTGCTGTAATCAGTTAGAAGAAAA

TAAAATCAAAGAAATGAAAAAGGAACATAACAATAATAATATAATGGTAACATTTGTTCTTT

GCTCAGAACACAAATATGAGATTGTGAAACGCCTACAAGCACGGAAGCACATTTGTGGAATG

ACTGGTGATGGCGTAAATGATGCACCAGCCCTAAAGAAAGCTGATATTGGTATAGCGGTTGC

CGATGCGACAGATGCAGCGAGGAGTGCTTCTGATATCGTACTAACCGAACCTGGTCTAAGTG

-continued

TGATCATTAGTGCCGTCCTTACCAGTCGAGCCATTTTCCAGCGGATGAAGAACTACACTGTA

TGTCAGATTGACCCCAGTGGATGAGAATTTTCTTTGCCCCCATTTATTTGAAGAGTTATTCC

TACATTTATGCTTGTGTCATTTAGCCCATATGCTAATCCAATTTCATGCTTGCAGATCTATG

CGGTTTCAATTACGATACGTATTGTGGTATGTTTGATTGACACTATAAAAGTTTGCCAAAGT

GCATTGGCTCATGCTCTGTTTTACATAGTTGATGATTCTCTTACGTGTCAATTATAACTATT

CGTTTAATGAATTTTTTCTTTTAACATTGATGTTCCAGTATATGATGTTTTCATCTTGATCT

GTGAAATTATGTCCATGAAGCTAACATTTTTTTATTTTGTGATTATGCATCTGATTCCTCTT

TACCCCCTAACAGCTTGGATTTATGCTACTTGCCCTCATATGGGAGTTTGATTTCCCGCCAT

TTATGGTCCTGATCATAGCAATTTTGAATGATGGTACAATTCTTTCTTTTCCTTCCATTCTC

CCCGCGCTTCCCGTGCCTACAATATCACCGTATTAAGTAGAAAATTATATTATAGTGCTCAC

CCTGAAGGCCTGAACCATTTTGTGGCATGAACAGGTACCATAATGACAATATCGAAGGATCG

AGTAAAGCCTTCCCCACTACCTGACAGCTGGAAGTTGGCTGAAATTTTCACAACTGGGGTGG

TTCTTGGCGGATACTTGGCAATGATGACTGTCATTTTCTTCTGGGCTGCATACAAGACTAAC

TTTTTCCCTGTAAGGAGTACCTAAGTGAAATTAAATTCTGTTTTTTTTTCTAAAACATTGAT

TGCAGATAATGAAGTAACCTCTTGATATGTGGCCCACGAAGCTACCAACTATTAGGACCAAT

ATGCTAGTTTGTGATCTGATCCTCAGACATGCATTGACACTTGTTGTTCAATAAATTTTCAG

AGGGTCTTTCATGTGAAAAGCCTTGAGAAGACAGCTCAAGATGACTTCAAAATGCTTGCCTC

TGCTGTATACCTTCAAGTCAGCACCATCAGCCAAGCTCTCATCTTCGTTACAAGGTCTCGAA

GTTGGTCGTTCGTCGAGCGCCCTGGCTTTCTCCTGGTCTTCGCTTTCTTTGTCGCGCAGCTG

GTATTTTTTCTCACGGTCTCACCCACTGTTTGCTTTACATGTAAGTACACAAGTCAAGTTCC

AGTGAGCAAGTTTCAAGTTTCACCACCCCCTTCAAAAAATGCAGATAGCTACACTGATCGCT

GTATACGCCGACTGGGGATTCACTTCGATCAAAGGCATCGGATGGGGCTGGGCTGGCATCGT

GTGGCTCTACAACATCGTCTTCTACTTCCCGCTTGACATCATCAAGTTCTTCATCCGATACG

CTCTGAGCGGCAAAGCATGGGATCTTGTCATTGACCAAAGAGTAGTTCAAAATTTCAAATTG

CACCACCATATTTTTCCTTGTCTTTTTTAGCTATTGAGAACCCAATACATTCTATGCATCTT

GTAAATGATGGTTCATTTCTCCTTTTTCTTTATAGATCGCATTTACAAGGAAGAAGCACTTT

GGTAAGGAAGAGAGGGAGCTCAAGTGGGCCCATGCACAGAGGACACTCCATGGGCTGCAGCC

GCCGGATGCCAAGCTGTTTCCTGAGAAGGCAGGCTACAACGAGCTGAATCAAATGGCCGAGG

AGGCGAAGCGGAGGGCTGAGATTGCAAGGTATGTAGGACCTGATTCCCAGCAGGCACTTGCA

TGAAATTCCACGTATGGGATGCATTCCAAGATCACCCTATTTCTTGACAATTATGAATCCAA

CTTATGTGCTTATTAATGACGGTACATGGCATGCAGGCTCAGGGAGCTCCACACTCTCAAGG

GGCATGTGGAGTCAGTTGTGAAGCTGAAGGGCCTCGACATCGACACCATTCAGCAATCTTAC

ACCGTGTGATAGATTCAAGTATCCTTAAAAGTTACTGTAGAAGAGAGAGTATATCCTTGCTG

CCTAGGAATAACAGACTTTTGATAGGTTGCTTTTGCCCCCTCTTATATAGTTGACTGCTGAT

ACGTCGTGGGAATAAAACGGTTACTACACATCTCAGCTGCTCTCCAGTCGCTGGTTCGTTGT

GCTTCATGTAAAGGAATACAGTTATCCTGTCTCTTGCTTCTGCAACTGGGGGTTTTA

B
>A. peregrina_clones F1&F2

(SEQ ID No. 2)

CAAGACCATACGTACACATAAATAAATCATTGAATCCCAAAGAAGAAGAAGAAGAAGAGCAG

AGGAGGAGGGTCCAGAAGAGTAGTTGGCGGTGGGAAGATCCAGAGGCTGCGCACTGCCTGCC

-continued

CGGCCGCCCCCGTCGCCATGGCCAGCAGCAGGCAGGAGGGGAACCTCGACGCCGTCCTCAAG

GAGGCCGTCGACCTGGTAATCACTCAGTTCATCAATCAACTCCCTGCTCTTGGGGTAGTATA

GTGCTTCCTCTCTGGTTTTTAGTTAGCGTTGCGCTTCTTGGGGAAATCACCATGTGGCTCGG

CCGTCGGCCGCTGGGGTTTCTTTCCGCGCTTCGGGCGTCGCAGTTGCATTGCAGGGTGGTGG

AGTTGGCCTGCCAGCGCCTCTTCTTGTAGGTCAATTTGGGAGCGTCGATCTCCCTCCCCTGC

CTAGTGTACCGCACTGCTCTAAAATCTCACCCCCCAAATCTTACTAAGCAAAATTTCACCCA

GGCTACAACTTTGAGCTACTATTTTTTCCCAGGGCTTACAAAAACTGCAGTTTAGTTTTAAA

TTTTAAAATCTCGCAGTTTTATATATAGCTTTGATTTTTATTTTGTCTGGACAGCGTATGAG

GGCTGCTTGTAAATGTATTTGCTCTAGCTTCGGATTATTTTGATTTTTCTTTTGTCTGGACA

GTGTATGACGGCTGATCACAAGAAGTACATACTTTTTCCTCTGTTTGATTAGAATTTTTATG

ATCCTCTGTTTGATTAGAATTTTTTTTTTGTCTCTTGGTTCTCTCTTCTGGGTTCCTTAGAG

TAGCAGGCTGCAGCTAGCATACTTGCACGTTCAGATTTTGCTCATGCTAATGGTACTTGTTT

GGTTTTGATAAAAGAGATTGCCGTAACAAAATTTCAGGAGCACATCCCAATTGATGAAGTGT

TTGAGAACCTTCGGTGCAGCCACGAGGGGCTCGCTTCCGAGCAGGCGCAGCAGCGGCTGCAG

ATCTTTGGCCCGAACAAGCTCGAGGAGAAGGAGGTCAGGTTCTTTCAGCCCATTTGATTATG

GGGAAGATTTTGTCCTTGCTCTTCTTGAGAGCAGTAATGTTCTTCTCATTGATGTTATGCAC

TTGAGTAAGTTGGAGTGTTTGATGGCTGCAGGAGAGCAAGTTCCTCAAGTTTCTGGGGTTCA

TGTGGAATCCACTGTCATGGGTCATGGAGGCTGCGGCGATCATGGCCATCGCGCTGGCGAAC

GGAGGGGTAAGACCCAGCACATAGTATTGCAGAATTTGTGGTGATGAGTGATGTTGTATGTC

CTGCTCTGTTCTCAATATATATGTGGGATGTGTTCTGTCACCACCAGGGGAAGCCACCAGAT

TGGCAAGACTTTGTCGGTATCATCACGCTGCTACTTATAAACTCCACCATCAGTTTCATCGA

GGAAAACAATGCCGGAAATGCTGCCGCCGCGCTTATGGCACGTCTTGCACCAAAAGCCAAGG

TCCATATATTCACTTAATTTGTGGCATTTCCCCTGTTTCTGCACGTATCACCTTGTTGGAGT

CCATTTTAACTTGTGAAACTCATTATTATATTGCTAAGTAGGTTCTCCGTGACGGTCGTTGG

ACCGAGGAGGAGGCAGCCGTCCTTGTGCCTGGGGACATCATCAGCATCAAACTTGGAGATAT

CATTCCTGCCGACGCCCGCCTCCTAGACGGCGATCCTTTGAAGATTGATCAGGTTTTTTCTG

TCCTTCACATCCGAGTCACCTTCAGCTTTGCTTTTACTTATTTAGATTTCCTATTTCCTCAT

CTCACTACTTGGTCTTTTATTTATAGTCTGCCCTGACTGGAGAATCGCTGCCAGCCACCAAA

GGTCCTGGTGACGGCGTCTACTCTGGTTCGACGGTCAAGCAGGGCGAGATCGAGGCTGTTGT

CATAGCAACTGGTGTGCACACTTTCTTTGGGAAGGCCGCACATCTCGTCGACTCCACCAACC

AAGTTGGCCATTTCCAACAGGCAAGCTTGACAAGCCTCGGATACTTTTATCGAATTGTATCA

TCGCTACATTGATGTTTTCATTATCATGCGATTGACGCAGGTGTTGACAGCCATCGGGAACT

TTTGCATTTGCTCGATTGGTGTGGGGATGTTCATAGAGATCATTGTCATGTATCCTATCCAG

CACAGGGCGTACCGCCCTGGGATCGACAACCTTTTGGTGCTTCTCATTGGAGGCATTCCCAT

AGCGATGCCCACAGTCTTGTCGGTCACCATGGCGATTGGGTCTCATCGCTTGTCTCAACAGG

TATGCATCATTCCAGGGACAGTGTCTCTTAACCATATTGTGACCAGACCTGAACTTCTGCAC

CATGCAATCAATTCCTGAGTTTTCTTCCTGCAGGGAGCTATAACAAAGAGAATGACTGCAAT

CGAAGAGATGGCCGGCATGGATGTTCTTTGCAGTGATAAGACTGGAACCCTGACTCTAAATA

AGCTCAGCGTGGACAAGAACCTAATCGAGGTAAGGTTCACTTGAACACTCACTTTTTGTTAT

CTCATATGTAACACCAAAGCACTTGCATACTTTCTTGGTCCAGGTTTTTGAAAAAGGAGTGA

CTCAGGACCAGGTGATTCTGATGGCTGCTAGAGCATCCCGGATAGAAAATCAAGATGCCATT

-continued

GATACGGCGATTGTTGGGATGCTAGGCGATCCAAAAGAGGTACATTGATTCGTCGAATAATG
AGACGTACAGCTATCACGTTTATTTGCTAAAATGGATACCTGTTAACTCTCCCCGTAGGCGC
GTGCCGGTATTCAAGAGGTTCATTTTCTGCCGTTTAATCCTACCGACAAAAGAACTGCGTTG
ACATACATTGATGGCGATGGAAAGATGTACCGTGTTAGCAAAGGTGCACCAGAGCAGGTATA
ATCTTTTCTTACTGCAAAAAGCTTAAAAAACATTTGCATAATGATGTAAATTGATTTCACAA
ATTGACCTGCAGATTCTTAACCTGGCCTACAACAAGTCAGAGATCGCACAAAAAGTCCACAC
TGTCATCGACAAGTTCGCGGAACGTGGACTTCGGTCACTTGGTGTAGCATATCAGGTGAGAA
AGGTTCTGGGTGTGCCCCTTCACAGTGCAGTTGAAGTTTGCAAGGCAGGAACTTAGTGGTGG
TCATTCTTTTCTGCCTTGTAGGACGTGCCAGATAGGAGGAAAGAGAGCCCGGGTAGCCCGTG
GCATTTTGTTGCTCTCTTGCCACTCTTTGATCCACCGAGGCACGACAGCGCAGAAACAATTC
AAAGGGCACTTAACCTTGGTGTGAATGTGAAGATGATCACAGGTACACTGCCAATTGGGTTG
TTACTACTTTTTTGCTCTGTTCTTAAATATCCAATTCGATGAAGATGATCACAAGTAAATGC
ACTACCGGTTGAATTCTATTTTGTTCTCTTCTCTCTATTCTTAAATCTCCCAATTTTTATGA
GCACCATGTCTTTGATGTTTACTATTTTTTATTTGTGATGTCATGTAAGTACCCCTTAAAAA
GCTGTGCCATAAGTAATTGAACATATGCTGTATCTTATCTTGTTTTATTATAATTTCAGTTT
CAGTAATTTTGGTAATACATCTTATTGTGCTTTTCCCCCCTAAGGCGACCAGCTAGCGATTG
GGAAGGAAACAGGGCGTCGTCTAGGAATGGGTACAAACATGTACCCATCATCTGCTTTGCTG
GGGCAGAACAAGGATGAGTCTATTGCTGATTTACCAGTCGATGATCTAATTGAGAAAGCCGA
TGGTTTTGCTGGCGTATTCCCAGGTATGTGTTGTAATCAGTTAGAAGAAAATAAAATCAAAG
AAATGAAAAAGGAACATAACAATAATAATATAATGGTAACATTTGTTCTTTGCTCAGAACAC
AAATATGAGATTGTGAAACGCCTACAAGCACGGAAGCACATTTGTGGAATGACTGGTGATGG
CGTAAATGATGCACCAGCCCTAAAGAAAGCTGATATTGGTATAGCGGTTGCCGATGCGACAG
ATGCAGCGAGGAGTGCTTCTGATATCGTACTAACCGAACCTGGTCTAAGTGTGATCATTAGT
GCCGTCCTTACCAGTCGAGCCATTTTCCAGCGGATGAAGAACTACACTGTATGTCAGATTGA
ACCCAGTGGATGAGAATTTTCTGTGCCCCCATTTATTTGAAGAGTTATTCCTACATTTATGC
TTGTGTCATTTAGCCCATATGCTAATCCAATTTCATGCTTGCAGATCTATGCGGTTTCAATT
ACGATACGTATTGTGGTATGTTTGATTGACACTATAAAAGTTTGCCAAAGTGCATTGGCTCA
TGCTCTGTTTTACATAGTTGATGATTCTCTTAGGTGTCAATTATAACTATTCGTTTAATGAA
TTTTTTCTTTTAACACTGATGTTCCAGTATATGATGTTTTCATCTTGATCTGTGAAATTATG
TCCATGAAGCTAACATTTTTTTATTTTGTGATTATGCATCTGATTCCTCTTTACCCCCTAAC
AGCTTGGATTTATGCTACTTGCCCTCATATGGGAGTTTGATTTCCCGCCATTTATGGTCCTG
ATCATAGCAATTTTGAATGATGGTACAATTCTTTCTTTTCCTTCCATTCTCCCCGCGCTTCC
CGTGCCTACAATATCACCGTATTAAGTAGAAAATTATATTATAGTGCTCACCCTGAAGGCCT
GAACCATTTTGTGGCATGAACAGGTACCATAATGACAATATCGAAGGATCGAGTAAAGCCTT
CCCCACTACCTGACAGCTGGAAGTTGGCTGAAATTTTCACAACTGGGGTGGTTCTTGGCGGA
TACTTGGCAATGATGACTGTCATTTTCTTCTGGGCTGCATACAAGACTAACTTTTTCCCTGT
AAGGAGTACCTAAGTGAAATTAAATTCTGTTTTTTTTCTAAAACATTGATTGCAGATAATGA
AGTAACCTCTTGATATCTGGCCCACGAAGCTACCAACTATTAGGACCAATATGCTAGTTTGT
GATCTGATCCTCAGACATGCATTGACACTTGTTGTTCAATAAATTTTCAGAGGGTCTTTCAT
GTGAAAAGCCTTGAGAAGACAGCTCAAGATGACTTCAAAATGCTTGCCTCTGCTGTATACCT

-continued

TCAAGTCAGCACCATCAGCCAAGCTCTCATCTTCGTTACAAGGTCTCGAAGCTGGTCGTTCG

TCGAGCGCCCTGGCTTTCTCCTGGTCTTCGCTTTCTTTGTCGCGCAGCTGGTATTTTTTCTC

ACGGTCTCACCCACTGTTTGCTTTACATGTAAGTACACAAGTCAAGTTCCAGTGAGCAAGTT

TCAAGTTTCACCACCCCCTTCAAAAAATGCAGATAGCTACACTGATCCCTGTATACGCCGAC

TGGGGATTCACTTCGATTAAAGGCATCGGATGGGGCTGGGCTGGCATCGTGTGGCTCTACAA

CATCGTCTTCTACTTCCCGCTTGACATCATCAAGTTCTTCATCCGATACGCTCTGAGCGGCA

AAGCATGGGATCTTGTCATTGACCAAAGAGTAGTTCAAAATTTCAAATTGCACCACCATATT

TTTCCTTCTCTTTTTTAGCTATTGAGAACCCAATACATTCTATGCATCTTGTAAATGATGGT

TCATTTCTCCTTTTTCTTTATAGATCGCATTTACAAGGAAGAAGCACTTTGGTAAGGAAGAG

AGGGAGCTCAAGTGGGCCCATGCACAGAGGACACTCCATGGGCTGCAGCCGCCGGATGCCAA

GCTGTTTCCTGAGAAGGCAGGCTACAACGAGCTGAATCAAATGGCCGAGGAGGCGAAGCGGA

GGGCTGAGATTGCAAGGTATGTAGGACCTGATTCCCAGCAGGCACTTGCATGAAATTCCACG

TATGGGATGCATTCCAAGACCAGCCTATTTCTTGACAATTATGAATCCAACTTATGTGCTTA

TTAATGACGGTACATGGCAGGCTCAGGGAGCTCCACACTCTCAAGGGGCATGTGGAGTCAGT

TGTGAAGCTGAAGGGCCTCGACATCGACACCATTCAGCAATCTTACACCGTGTGATAGATTC

AAGTATCCTTAAAAGTTACTGTAGAAGAGAGAGTATGTCCTTGCTGCCTAGGAATAACAGAC

TTTTGATAGGTTGCTTTTGCCCCCTCTTTGTTGACTGCTGATACATCGTGGGAATAAAACGG

TTACTACATCTCAGTTGCTCTCCAATTGCTGGTTCGTTGTGCTTCATGTAAAGGAATACAGT

TATCCTGTCTCTTGCCTCTGCAACTGGGGGTTTTA

C

>A._crassa_clones1&2&4&5

(SEQ ID No. 3)

GGCCGTCGACCTGGTAATTAACCAACGCCCTGCTCTTGGGGTGGCGCTTCCTGTGGTTTCTA

GTGGCCGCGGTGCTTGGATGTGGATGGGTTGCCGTTGCGCGCAGCTGGGCTTTTTTACCGGG

GCTTAGCAGTGTTCTTCTAGTTCTATAGGTCAATTCTTGTTCGGCATCGCCCTTTGTTTTGT

TACTAATTATTACGAATCCCGCAACTCTAGATCACCATCTTCTAGGCCTGCTCTGTTTTGTT

GCCAACAGAGGATCCCCTGCCTCGTTGGTTTACTCACATTAGTTCCTGAGAATCTCACACTA

GAACTTCTGATTGTTTTTTGCGTGCCGTGTAGGAGGGCTGCCCTGTCAATGTATTTACTCTA

GCTTTGTAGTATTATTTTGTATCTTTTTTTTGTTCTAACTTAAGGTGACTGGACCGTGGGAA

AAAGTGTGTACTCATGATCCTCTGTTTAATTGGATTTGATTTTTTTTTTGGCCTCTTAGCTT

GGTTCTCTCTTCTGGGTTCCTTGGAGTAGTAGGCTGCAGCTAGCATGCTTGCACGTTCAGAA

TTGCTCATGGTAATGGTACTTGTTTGGTTTGCTAAAAGCGATCGTCGCAACAAAATTTCAGG

AGCACATCCCGATCGATGAAGTGTTCGAGAAGCTTCGGTGCAGCCACCAGGGGCTCACTTCC

GAGCAGGCGCAGCAGCGGCTGCAGATCTTCGGCCCGAACAAGCTCGAGGAGAAGGAGGTCAG

GTTCATTCGGCCCATTTGATTGTGGGGAAGATTTTGTCTTTGCTCTTCTTGAGAGCAGTAAT

GTTCTTCTCATTGATGTTATGCACTTGATTAAGTTGGAGCGTTTGATGGCTGCAGGAGAGCA

AGTTCCTCAAGTTTCTGGGGTTCATGTGGAACCCACTCTCATGGGTCATGGAGGCTGCGGCG

ATCATGGCCATCGCGTTGGCCAACGGAGGGGTAAGACCTAACACGTATATAGCAGAATTTGT

GGTGATGTTTTAGTTGGGTGCTGAGTGGAGTGCACGTCTTGCTCTGTTCTCAACATGTGARA

AGATGTGTGTTCTGTAATCAGGGGAAGCCACCAGATTGGCAAGACTTTGTCGGTATCATCAC

GCTGCTGCTTGTAAACTCCACCATCAGTTTCATCGAGGARAACAATGCCGGAAATGCCGCCG

CCGCGCTTATGGCCCGTCTTGCACCAAAAGCCAAGGTCTATATTCAGTTTAATTTGTGGGGG

-continued

TTTTCTGTCCCCTGTTTCTGGATGTACGTGTCACCTTGTCGGAGTCCATTTGAACAGTGAAA

CTCAATTCTTATGTTGCTAAGTAGGTCCTCCGTGATGGTCGTTGGACCGAGGAGGAGGCAGC

CGTCCTTGTGCCTGGGGACATCGTCAGTATCAAACTTGGAGATATCATTCCTGCCGACGCCC

GCCTCCTAGACGGCGATCCTTTGAAGATTGATCAGGTTCTTTCTGTCCTTCACATTCAAGTC

ACCTTCAGCTTTGCTTTTACTTATGTAGATTTCCTCGTCTCACTACTTGGTCTCTTATTTAT

AGTCTGCCCTGACCGGAGAATCGCTGCCAGCCACCAAAGGTCCTGGTGACGGCGTCTACTCT

GGTTCGACGGTCAAGCAGGGCGAGATCGAGGCTGTTGTCATAGCAACTGGTGTGCACACTTT

CTTTGGAAAGGCTGCACATCTCGTCGACTCCACCAACCAAGTTGGCCATTTCCAACAGGCAA

GCTTGACAAGCCTCGGATACTTTTATCGAATTGTATCATCGCTACATTGATGTTTTCATTAT

CAAGCGATTGATGCAGGTGTTGACAGCCATCGGGAACTTTTGCATTTGCTCGATTGCTGTGG

GGATGTTCATAGAGATCATTGTCATGTATCCTATCCAGCACAGGGCGTACCGCCCTGGGATC

GACAACCTTTTGGTGCTTCTCATTGGAGGCATTCCCATAGCGATGCCCACAGTCTTGTCGGT

CACCATGGCGATTGGGTCTCATCGCTTGTCTCAACAGGTATGCATCATTCCAGGGACAGTGT

CTCTTAACCATATTGTGACTAGACCTGAACTTCTGCACTAAGCAATCAATTCCTGAGTTCTC

TTCCTGCAGGGAGCTATAACAAAGAGAATGACTGCAATCGAAGAGATGGCCGGCATGGATGT

TCTTTGCAGTGATAAGACTGGAACCCTGACTCTAAATAAGCTCAGCGTGGACAAGAACATTA

TCGAGGTTCACTTGAACACTAGCTTTGTATTATCCCACATGTTACCTCAAAGCACCTACATA

CTTTTTTTGGTCCAGGTTTTTGAAAAAGGAGTGACTCAGGACCAGGTGATTCTGATGGCTGC

TAGAGCATCCCGGATAGAAAATCAAGATGCCATTGATACGGCAATAGTTGGCATGCTAGGTG

ATCCAAAAGAGGTACATTGATTTGTCGAATAGTGAGATGTACACCTGTCATGTTTATTTGCT

AAATAGACATCTATCAACGCTTCCCATAGGCACGGGCCGGTATTCAAGAGATCCATTTTCTG

CCGTTCAATCCTACCGACAAAAGAACTGCGTTGACATACATTGATAGCGATGGAAAGATGTA

CCGAGTTAGCAAAGGTGCACCAGAGCAGGTATAATATTTTTTACTGCAAAAAGCTTAAAAAA

CATTTGCATAATGAGTAAATTGATTTCACAAATTGACCTGCAGATTCTTAACCTGGCCTACA

ACAAGTCAGAGATCGCACAAAAAGTCCACACTGTCATCGACAAGTTCGCGGAACGTGGACTT

CGGTCACTTGGTGTAGCATATCAGGTGAGAAAGGTTCTGGGGGTGCCCCTTCACAATGCAGT

TGAAGCTTGCAAGGCAGGAACTTAGTGGTGGTCATTCTTTTCTGCCTTGTAGGACGTGCCAG

ACGGAAGGAAAGAGAGCCTGGGTAGCCCGTGGCATTTTGTTGCTCTCTTGCCACTCTTTGAT

CCACCGAGGCACGACAGCGCAGAAACAATTCAAAGGGCACTTAACCTTGGTGTGAATGTGAA

GATGATCACAGGTACACTGCCAATTGGGTTGTTACTACCTTTCTGCTCTGTTCTTAAATATT

CAATTCGATGAAGATGATCACAAGTAAATGCACTACCGGTTGAATTCTATATTGTTCTCTTC

TCTCTATTCTTAAATCTCCCAATTTTTATGAGCACCATGTCTTTGATGTTTACTATTTTTGA

TTTGTGATGTCATGTAAGTATCCCTTAAAAAGCTGTGCCATAAGTAGAGTTAGAACGTTGAA

CCATATGCCGTATCTTATCTTGTTTTATTTATAATTTCAGTTTCAATAATTTTGGTAATACA

TCTCATTGTGCATTTTTTTTTTGTTTTTCCTTAGGCGACCAGCTAGCGATTGGGAAGGAAACA

GGGCGTCGTCTAGGAATGGGTACAAACATGTACCCTTCATCTGCTTTGCTGGGGCAGAACAA

GGATGAGTCTATTGCTGATTTACCAGTCGATGATCTAATTGAGAAAGCCGATGGTTTTGCTG

GCGTATTCCCAGGTATGTGTTGTAACCAGTTAGAAGAAAATAAAATCAAAGAAATGAAAAAG

GAACATAACAATAATAATATAATGGTAACATTTTTTCTTTGCTCAGAACACAAATATGAGAT

TGTGAAACGCCTACAAGCACGGAAGCACATTTGTGGAATGACTGGCGATGGCGTAAACGATG

-continued

CACCAGCCCTAAAGAAAGCTGATATTGGTATAGCGGTTGCCGATGCGACAGATGCAGCGAGG

AGTGCTTCTGATATCGTACTCACCGAACCTGGTCTAAGTGTGATCATTAGTGCCGTCCTTAC

CAGTCGAGCGATTTTCCAGCGGATGAAGAACTACACTGTATGTCAGATTGAACCCAGTGGAT

GAGAATTTTCTTTGCCCCCATTTATTTGAAGAGTTATTCCTACATTTATGCTTGTGTCATTT

AGCCCATATGCTAATCCACCTTCATGCTTGCAGATCTATGCGGTTTCAATTACGATACGTAT

TGTGGTATGTTTGATTGACACTATAAGTTTGCCAAAGTGCATTGGCTCATGCTCTGTTTTAC

ATAGTTGATGATTCTCTTAGGTGTCAATTATAACTATTCGTTTAATGAATTTTTTCTTTTAA

CACTGATGTTCCAGTATATGATGTTTTCATCTTGATCTGTGAAATTATGTCCATGAAGCTAA

CATTTTTTTTATTTTGTGATTATGCATCTGATTCCTCTTTACCCCCCACCAGCTTGGATTTA

TGCTACTTGCCCTCATATGGGAGTTTGATTTCCCGCCATTTATGGTCCTGATCATAGCAATT

TTGNATGATGGTACATTACTTTCTTTTCCTTCCATTCCTCCGGCGCTTCCCGCGCCTCACAA

TATCACCGTATTAAGTACAAAATTATATTGTAGTGCTCACCCTTAACCATTTTGTGGCATGA

ACAGGTACCATAATGACAATATCGAAGGATCGAGTAAAGCCTTCTCCACTACCTGACAGCTG

GAAGTTGGCTGAAATTTTTACAACTGGGGTGGTTCTTGGCGGATACTTGGCAATGATGACTG

TCATTTTCTTCTGGGCTGCATACAAGACTAACTTTTTCCCTGTAAGGAGTACCTAAATGAAA

CTAAATTCTGTTTTTTCTTCTGTAAGGAGTACCTAAATGAAAATCGCTTGATATGTTGTTCA

CCAAGCTACCAACTATTAGGACCATTATACTAGTTTGTGATCTGATCCTCAGACATGCATTG

ACACTTGTTGTTCAATAAATTTTCAGAGGGTCTTTCATGTAAAAAGCCTTGAGAAGACCGCT

CAAGATGACTTCAAAATGCTTGCCTCTGCTGTATACCTTCAAGTCAGCACCATCAGCCAAGC

TCTCATCTTCGTTACAAGGTCTCGAAGCTGGTCGTTCGTCGAGCGCCCCGGCTTTCTCCTGG

TCTTTGCTTTCTTGGTCGCACAGCTGGTATTTTTTTTTCTCACGGCCTCGCCCTCCTCGCTT

TGCTTTACATGTATGTAAATTTACAAGTCAAGTTCCAGTAGCAAGTTTCACCACCTCCTTCA

AAATGCAGATAGCTACACTGATCGCTGTATACGCCGACTGGGGATTCACTTCGATCAAAGGC

ATCGGATGGGGCTGGGCTGGCATCGTGTGGCTCTACAACATCGTCTTCTACTTCCCGCTTGA

CATCATCAAGTTCTTCATCCGATACGCTCTGAGCGGCAAAGCATGGGATCTTGTCATTGACC

AAAGAGTAATTCAAATTGCACCACCATATTTTTCCTTCTCTTTTTAGCTATTGAGAACCCAC

TACATTCGATGCATCTTGTAAATGACGGTTCATTTGTCCATTTTCTTTATAGATCGCGTTTA

CAAGGAAGAAGCACTTTGGTAAGGAAGAGAGGGAGCTCAAGTGGGCCCATGCACAGAGGACG

CTCCATGGGCTGCAGCCACCGAATGCCAAGCTGTTCCCTGAGAAGGCGGGCTACAACGAGCT

CTGTCAGATGGCCGAGGAGGCGAAACGGAGGGCCGAGATTGCAAGGTATGTAGGGCTAGATA

CCCAGCAGGCACTTGCAAATTAGAGAATCCCATCTTCCATATTTTTTGACAACTACTCCCTA

TGTTAGCTTAAAAAACGCTCTTATATTATGGGGTGGAGGGAGTATGAGTCTAACTACGTGCT

TGTTGATTGTGCATGGCAGGCTCAGGGAGCTCCACACTCTCAAGGGGCATGT

D
>Ku37seq_clonesD2&D3

(SEQ ID No. 4)

MASSRQEGNLDAVLKEAVDLEHIPIDEVFENLRCSHEGLASEQAQQRLQIFGPNKL

EEKEESKFLKFLGFMWNPLSWVMEAAAIMAIALANGGGKPPDWQDFVGIITLLLINS

TISFIEENNAGNAAAALMARLAPKAKVLRDGRWTEEEAAVLVPGDIISIKLGDIIPADA

RLLDGDPLKIDQSALTGESLPATKGPGDGVYSGSTVKQGEIEAVVIATGVHTFFGK

AAHLVDSTNQVGHFQQASLTSLGYFYRIVLTAIGNFCICSIGVGMFIEIIVMYPIQHRA

YRPGIDNLLVLLIGGIPIAMPTVLSVTMAIGSHRLSQQGAITKRMTAIEEMAGMDVLC

-continued

SDKTGTLTLNKLSVDKNLIEVFEKGVTQDQVILMAARASRIENQDAIDTAIVGMLGD

PKEARAGIQEVHFLPFNPTDKRTALTYIDGDGKMYRVSKGAPEQILNLAYNKSEIAQ

KVHTVIDKFAERGLRSLGVAYQDVPDRRKESPGSPWHFVALLPLFDPPRHDSAETI

QRALNLGVNVKMITGDQLAIGKETGRRLGMGTNMYPSSALLGQNKDESIADLPVD

DLIEKADGFAGVFPEHKYEIVKRLQARKHICGMTGDGVNDAPALKKADIGIAVADAT

DAARSASDIVLTEPGLSVIISAVLTSRAIFQRMKNYTIYAVSITIRIVLGFMLLALIWEFD

FPPFMVLIIAILNDGTIMTISKDRVKPSPLPDSWKLAEIFTTGVVLGGYLAMMTVIFFW

AAYKTNFFPRVFHVKSLEKTAQDDFKMLASAVYLQVSTISQALIFVTRSRSWSFVE

RPGFLLVFAFFVAQLIATLIAYADWGFTSIKGIGWGWAGIVWLYNIVFYFPLDIIKFFI

RYALSGKAWDLVIDQRIAFTRKKHFGKEERELKWAHAQRTLHGLQPPDAKLFPEK

AGYNELNQMAEEAKRRAEIARLRELHTLKGHVESVVKLKGLDIDTIQQSYTV

E
>A. peregrina seq_clonesF1&F2
(SEQ ID No. 5)
MASSRQEGNLDAVLKEAVDLEHIPIDEVFENLRCSHEGLASEQAQQRLQIFGPNKL

EEKEESKFLKFLGFMWNPLSWVMEAAAIMAIALANGGGKPPDWQDFVGIITLLLINS

TISFIEENNAGNAAAALMARLAPKAKVLRDGRWTEEEAAVLVPGDIISIKLGDIIPADA

RLLDGDPLKIDQSALTGESLPATKGPGDGVYSGSTVKQGEIEAVVIATGVHTFFGK

AAHLVDSTNQVGHFQQASLTSLGYFYRIVLTAIGNFCICSIGVGMFIEIIVMYPIQHRA

YRPGIDNLLVLLIGGIPIAMPTVLSVTMAIGSHRLSQQGAITKRMTAIEEMAGMDVLC

SDKTGTLTLNKLSVDKNLIEVFEKGVTQDQVILMAARASRIENQDAIDTAIVGMLGD

PKEARAGIQEVHFLPFNPTDKRTALTYIDGDGKMYRVSKGAPEQILNLAYNKSEIAQ

KVHTVIDKFAERGLRSLGVAYQDVPDRRKESPGSPWHFVALLPLFDPPRHDSAETI

QRALNLGVNVKMITGDQLAIGKETGRRLGMGTNMYPSSALLGQNKDESIADLPVD

DLIEKADGFAGVFPEHKYEIVKRLQARKHICGMTGDGVNDAPALKKADIGIAVADAT

DAARSASDIVLTEPGLSVIISAVLTSRAIFQRMKNYTIYAVSITIRIVLGFMLLALIWEFD

FPPFMVLIIAILNDGTIMTISKDRVKPSPLPDSWKLAEIFTTGVVLGGYLAMMTVIFFW

AAYKTNFFPRVFHVKSLEKTAQDDFKMLASAVYLQVSTISQALIFVTRSRSWSFVE

RPGFLLVFAFFVAQLIATLIPVYADWGFTSIKGIGWGWAGIVWLYNIVFYFPLDIIKFFI

RYALSGKAWDLVIDQRIAFTRKKHFGKEERELKWAHAQRTLHGLQPPDAKLFPEK

AGYNELNQMAEEAKRRAEIARLRELHTLKGHVESVVKLKGLDIDTIQQSYTV

F
>A._crassa_clones1&2&4&5
(SEQ ID No. 6)
AVDLEHIPIDEVFEKLRCSHQGLTSEQAQQRLQIFGPNKLEEKEESKFLKFLGFMW

NPLSWVMEAAAIMAIALANGGGKPPDWQDFVGIITLLLVNSTISFIEENNAGNAAAA

LMARLAPKAKVLRDGRWTEEEAAVLVPGDIVSIKLGDIIPADARLLDGDPLKIDQSAL

TGESLPATKGPGDGVYSGSTVKQGEIEAVVIATGVHTFFGKAAHLVDSTNQVGHF

QQASLTSLGYFYRIVLTAIGNFCICSIAVGMFIEIIVMYPIQHRAYRPGIDNLLVLLIGGI

PIAMPTVLSVTMAIGSHRLSQQGAITKRMTAIEEMAGMDVLCSDKTGTLTLNKLSVD

KNIIEVFEKGVTQDQVILMAARASRIENQDAIDTAIVGMLGDPKEARAGIQEIHFLPF

NPTDKRTALTYIDSDGKMYRVSKGAPEQILNLAYNKSEIAQKVHTVIDKFAERGLRS

LGVAYQDVPDGRKESLGSPWHFVALLPLFDPPRHDSAETIQRALNLGVNVKMITG

-continued

DQLAIGKETGRRLGMGTNMYPSSALLGQNKDESIADLPVDDLIEKADGFAGVFPEH

KYEIVKRLQARKHICGMTGDGVNDAPALKKADIGIAVADATDAARSASDIVLTEPGL

SVIISAVLTSRAIFQRMKNYTIYAVSITIRIVLGFMLLALIWEFDFPPFMVLIIAILNDGTI

MTISKDRVKPSPLPDSWKLAEIFTTGVVLGGYLAMMTVIFFWAAYKTNFFPRVFHV

KSLEKTAQDDFKMLASAVYLQVSTISQALIFVTRSRSWSFVERPGFLLVFAFLVAQLI

ATLIAVYADWGFTSIKGIGWGWAGIVWLYNIVFYFPLDIIKFFIRYALSGKAWDLVIDQ

RIAFTRKKHFGKEERELKWAHAQRTLHGLQPPNAKLFPEKAGYNELCQMAEEEAKR

RAEIARLRELHTLKGH

G TaFlo6 4A
MRRSDKPGAFPTRAELLAAGRADLAAAVESSGGWLSLGWSWSSDDDARRPAAS

TAGPGVHPEYPPEAGPSGRPPNSAADSVREQQEPAPSGRQPETEETEEAGSGAG

LEGMLARLRRERERARPPPRSKNQAGGRGQNGALMNHNGAPSRSPTNGMYTRR

IPVNGNIHRSHSQNGIPEDNKSSSSANDAWRTWSLDKSRFSDFEAAEIHPLSRKPP

KHVDLNTVLIEDDVPGPSNGVVINDYPSDHVDSERDEIHARFQNLEFDLADSLKTLR

SRFDGVSSYMSNGEEADVVNGFSDDWEFEETKVMHAQEELRTIRAKIAVLEGKVA

LEIIEKNKIIEEKQTRLDEVEKALSELRTVSVVWPNPASEVLLTGSFDGWTSQRRME

QSESGIFSYNLRLYPGRYEVMACYSAFIVTAFSSSDSGCWFVLQIKFIVDGVWKND

PLRPSVNNHGNENNLMIVT

H TaFlo6 4A
CAGACGCAGGCACGGCAACGGGTCACGGAGAGCTCGCCGCGGCAGGGACGTGACGTGTGTG

GTGGTGGACGGCGCTCGCGTGGCTCAGTTTTTTTTCCCCGTTTCCCCCCCTCCCTCCTCCGCTC

TCCAGTCCAGGGAAAGCTCCCGCCCTCGCCGCTCGGGGAGCGGCAGAGAAATGCGACGGCGA

TGCCCCCCTTCCTCCCCTCGNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNNNNNNNNNNNNNNN

NNNNNNNNNNNNNNNNGCCGCCACCGCGTCTTCGCCGCCGCCGCCGCCTACGGGCCGCAGCC

CTGCCGCGGCCGCGTCTGCGTCTGCGCCGCCTACAGGCCCCCGCCGCGGCAGCCCTACCGCC

GCCAGCCCGCCCCCGCCCCGGCCCCGCGCCCGCCCAATGCGCCCGCGCCGCCGCAGCGCGG

CCCGCGGGGCCAGGAGGAGCTCGAGGAGGCGATCTACGACTTCATGCGCCGCTCCGACAAGC

CCGGCGCCTTCCCCACCCGCGCCGAGCTCCTCGCCGCGGGGCGCGCCGACCTCGCCGCCGC

CGTCGAGTCCAGCGGAGGCTGGCTCTCCCTCGGATGGTCCTGGTCCTCCGACGACGACGCGC

GGCGGCCGGCTGCGTCAACGGCCGGCCCCGGCGTGCACCCTGAATACCCGCCCGAGGCGGG

TCCTTCTGGCCGACCGCCAAACTCGGCCGCGGATTCCGTAAGGTGGGTAACCGAGCCGCTCTG

TAATGTAATGTGTCCCCCTCTGTTGATTGCTCTGCGACGACTTGCTGAATTCCGAGTGTTGCAGG

GAGCAGCAGGAACCGGCGCCGTCTGGGAGGCAGCCGGAGACGGAGGAGACAGAGTGGGTGC

CTGCTAAATCTCTTTTGAGTTATTTTGATTGATATATGCTGGTTCCTTATTGATTTTGCTTGTTGCT

ACGTAATCGATTGCAGGGAGGCAGGGTCTGGGGCAGGCCTGGAGGGAATGCTCGCCAGGCTG

CGGAGAGAGAGGGAGCGTGCGCGGCCACCGCCACGCAGCAAGAATCAAGCGGGAGGGCGAG

GTCAAAATGGCGGTATGTGCAGCTTCGACTCTTGGCGTTCTATCGAAACATGTGTTGTTTTCAGT

TGTGCAACATGAGCATCTTCTTTGCAAACAGTTATATGTTTGTTGATAAGGGAACACCAACTTTTG

CAACCAATGAAACTTTGCATAGTATACAGCTCATTGTGCCATATTGTTTAGTTACAGCCCGTGGA

-continued

AGGCTTAATGCTCTGCTGGATAAAATTAATGCTAAGCTCATGCCGGGCAGGAAGGAAGTGCCGC

CGACAATAGTTCATGCAAAAGCTGTCTGTTCTCACGGACCGGACTTCCCTTTCCCCCGACATATA

TAACTAGCAGTGCAGTAGTTTAGCGCTTTCCATTTAAGGTTGCAAAGGGGACAAACATACCGTTT

TTTGTTCTATGTCGCTTTCTAAAAATAGAAGCGTGGCGTTAGAACTTTCTTTCTCATGATCCGACA

TATTTTTTGTCGTCGTGCTACTGCTTAATGTAAAGTTGTTTGCACCTTGACAGCACTGCAATTATT

TGAGTAATCGTGAATCTACAGAAGACTACCACATTATTTTGTTTGTGCCTTTTAATCATAGTAGTA

ATATGTTCTGTTACATACAACTGGTTTAGCTTTGTTATTACTCTGCCCATTTCAGCATTTGGTCCTT

CCAAGCTAATGGCTTTTTTGTGTTAAATCTCTTACAATACACGGAGGATAATTCATTTTCTATTTCA

AATATGCTGCTGTTAATAGTTGCCCCCTAACACCTAAATGAATTGAAGGGTCCATGCTCCCTAGA

TATACATGGTTGATTGAAGTTAGTAGACTCTGCGTTTTGCAAATATATTTACTAATTAATGACCGC

TTTAAGATTGACCATGTGTTTAGGTATTTTACTGATTTAGTGCACACGGATCATTTTCTCGGTAC

TCTATTAGTATCAACAGTAAAAAGTACACATTGTAAACTTTTGGCTGGAGACTCGGAGAGGAAAA

TTGAAAGAGTTCCACCTTATATAATAGAAAATAGCGTTGGTTTGTTATTGATGGACAACTAATGGA

TATTTTTTGTTAGAGAGCTTCTGGATAATTATGTATGTGAACCTTTATTCTGATGTACCATATACTT

AATTTCTAGCTGGTGTTTCTTCATTTGTATATTAATGATCATACTTCTGTGTTACATACATGCAGCT

TTAATGAACCATAATGGAGCTCCTAGTCGAAGTCCAACTAATGGCATGTACACTCGAAGGATACC

TGTGAATGGAAATATACACCGCTCTCATTCTCAAAATGGAATACCAGAGGACAACAAATCAAGTA

GTTCGGCCAATGATGCATGGCGAACATGGTCTCTTGACAAGAGTCGGTTTTCTGATTTTGAAGGT

TATATGATAACTTAACTTTCTTTCGTTGCGCATCATATCTGTTATGATTATTTCATAACATGTTTAAT

ATGCTGACAGCCGCTGAGATCCATCCTTTGAGCAGAAAACCACCAAAACATGTTGACCTGAACA

CTGTGTTGATAGAAGATGATGTTCCTGGACCATCTAATGGTGTGGTTATAAATGATTATCCTAGT

GATCATGTAGACTCTGAAAGAGATGAGATACATGCACGTTTTCAAAATTTGGAATTCGATCTTGC

AGATTCTCTTAAGACATTAAGATCAAGATTTGATGGAGTTTCGTCATATATGGTGTGTCTCGTCTC

TCGTATCATCTTCTTTACTTATCTATCTTTTGTTGTGAAATACTGGTGGGATACGTGATCTTGAGA

TTTTAGTGTGGTTTTGCATTCAGTTTTCTTCACTTATGCATTTGTAAAGTTGTTTATGCATTGTACT

AGACATGGCTCTGCTGTTCCTAACAAAACACACCTGAAGATGTGGTTCTGCTTGCTCTAATTTTC

TCTTTATGCACTAAACACTGTCTGCATCATACCCTCGCCCATCACTAGAAAAGTGCCATCTTTGG

ATGCATGCAGTCAAATTTTTTGATTTTGACTAACACTGTAACAGTATCCTCATCAATATGCAGTCT

GACAACATGAAAATGGTACAAGTTCATTTGCCAACGGAACAACTTCCATAAATTTTGATTTTATAT

CTGTAGATATTCACTGTATATCCACTATCTTTTCTTGCAATGTTGTGATTTCGCAACGCAAACAAA

TGACTATAGCTAATAATATTCCCTTGCAATGCTGATTGCTGAATGTAGTTGTGTTCTCTACGAGGA

AGTAGTTAGCTAGTCGCAAAATAAAAAGCACAGGTACGGAGACATGGACACAGCGATACGCCTA

GGGGACACGGGATACGGCATTAAACAGCCATTCAGGGATACGGCGAGTATATATGAAAAAAATT

AAAACATGCCATGTAATATAGAGTTAAAAAAATGAAGAGAAACTGAGATAAGATCAGAATACTGC

CCCATTTCCATTTGTTGTATTGTTTTTCAAGTGCTCAATGATTGAATTAATTGATCCTCTAGACCCA

TGTCATTGCAACTTGCAAAATACATCAAATGCTAGTATTAGTCTATTAGAGAGTAGAGACTGGAG

AAGACATGCAACAAAGGATGCAGGTGTAACTTTCACCCTCACCCATGGACGATTGGCCACCGGT

GGTGGCGCTCCCAAACGCCATGCTCCCTAACATCAAGCAACAATCAAAACAGCAGCACCAGGCA

CCAGCATGCAAGTGAGCAGCAGCTCAAGAGCAAGCAGCAACGGCATGGACGCATGGGGAAGC

AAGCAGCAGACTCAACAGCAAGAAATCGAGCAAAGATATGAAGAGGTTGAGAAGAGGCTGCTG

GGGTTATCTGCTTGAGCGTGGTTGCCATCGGGCGGTTGAGTCCAGGGGGCGGCGGTGATAGC

-continued

GCGTTCGACTTGGAGCAGCGTTCCTTTAGTGGCAAGCGTGTGTGCGACCTTGCAAAATAGGGTT

TGTATCGGGCCAAGGCTGTTATTGAGCTTCCTGTGTCCCCAACGTATTCCATACGTATCCCAGCT

GTGTCTTTGTTTTTTCCTTTCTTTAATTAGGAAATCAGGGGATACTGGGGGACACGCGTATCTTG

GCATGTCCGGCCATATCGCCGTGTCGCAACGAATTAGGACGGCAATTCGGCAGTTTCGGCCGT

TTCCATGCTTTGTTGGTCGCAATGATTTAGTTTGCAAATTATTACACATTCTTGTTTTTAGAACCAT

TGTATTACTGGTAGGAAGTTTCTGATTTTCGAGACTTGGCCCACGCTGATATGAAACTAAAACGA

TAATGGAAGATCTTGATGCATCTCATCTTGATTTTTCTAGAGGCAATATACTTGTTCTGAGCATCC

ATCTTTGCCCTTCCATTTTCCAGTCAAATGGCGAAGAAGCAGATGTGGTAAATGGGTTCTCTGAT

GATTGGGAATTTGAAGAGACAAAAGTAATGCATGCCCAGGAAGAATTACGGACAATCCGTGCTA

AAATAGCAGTATTAGAAGGCAAGGTGGCGCTAGAAATAATGTATGGTCACTCACAATTGAATGTT

GTTCATCTACGCTTTTTATTTTGTATCAATCTCTTTTATGACTTATTCTGTTGATATCAGTGAGAAG

AACAAAATAATTGAAGAAAAGCAAACGAGGCTTGATGAAGTTGAGAAGGCTTTGAGTGAGCTCC

GCACAGTATCTGTTGTATGGCCCAATCCTGCTTCAGAAGTTCTATTGACCGGTTCTTTTGATGGG

TGGACAAGCCAAGTAAGTGCATGTTCCTATTCTCTGCTTAATTAGTAAATATATAAACTTCAGTAA

CTAACTATAAAATGAGTGGCAGTTCGTGATTTCAATTTCTATCACTCTTTGGTGTTAGTTGTCAGG

TGAATTCCATTGATTTATGTATTAAGTTGAATATTAATGAAGAGAGAAGCTGGATCTATTGCTGCT

CTCCTAAGTTGTGTAAATGCAATTTACTGCCAACACCTTATCATGTGCACAGTTAATTCATTTCTT

AATGAGTGCAAAACAAACACAATACTCCCTCCGGTCCATATTACGGAGGGAGTACTTAATTTGAT

GTGGTTCACACACAAGTAAAGTAACTTCAGGAACTAGCAACATGATAGTTACGAGAATGGTAGG

GATCGAAGGCGCCCAAGTGCTTTGAAAGATGTTTATTACGTATATGTTTCTAGGAGTAAAGCAAG

TTTTTAATCTGATTTTGGTTGTTGGTGCTGTTTTTGGCATAGGCACAATTGTGACAACACGTGTCC

ATAACTTTTGTGTTAGAAATACTACGTGCTATTTGGATTTGGAAGTTTAGAAACATTGTTTTATATG

CCAAAAGAAAAAGGAAAAGCACATGGAATCTTCATATATTTGTTAATACTCCTTCCGTTCCTTTTT

ATGGCTTGTATTGGTTTGTTGGAAAGTCAAACTTTTCTCCCTTTGACCAAGTTTATAAAAGAATCA

ATGTATGCAATACTAAATACATAAAATATGGAAATATTTTTCATGAAGGGTCTGATGATACTGATTT

GGCATTGTAGATGTTGATACTTTTTTCTATATAAACTTGGTCAAAGATGGAAAAGGTGGACTTTAA

AAAAACATCTTATAAAAAGGAACGGAGGGAGTATGTATTTATCATTTTATATTAAGTGGAAACTGA

AGCAGCACAATTTTACAAGAGCTTCACTAGGCAAGACCTAGCAACAAATATACTACCTCTGCAAC

TTTTTATAAGACATTTTTAGAGTCTATGACAATGTGAAAAATGTCTCATATTAAGTTAGGGAGGGA

GTATATCTTTATCTGGTACCTTTAGCTGAGATTTAGTCAGTTCCTAGGAGGATACTGGTCACATG

ACTGACATATCCAAAAGGATGTTCAGTAGTTCAAGCACATATAGGATAGGTACTAGATGTAGAAG

CCTGAAGGACAACATTCTGCCATTATAGATCTTAGTTTCACTTTCATATGTATGGGGGTGCTGTTT

AGTTTTATTTTGTATACATGATATTTGCATTTCCATGGAGCACACAACACAATTCAGATCAGCCAG

CAGAAGAATGTTAGTAGTACAAATCAAATTTGGTTCTAGAGTAAGAAATATTACCTGTGTCCCAAA

TTACTTGTCTTAGATTTGTCTAGATAGGGATGTACCTATCTAGACAAATCTAAGACAAGTAATTCA

GGACGGAGGGAGTATGAATTTGTTATGCCATTTCACCTCTCTTGTCGCTCCTTTGATATAACTTT

CAAGATATTGAATATTTAAACATCTAATTATATGAATGTCCATGGAATGTTGTCTGCTTTGGGCTG

TGTACTGCAGGAAGTCTCTTTGTTACGTACTCCCTCTGTACCGAAATACATGTCGCTGGAGTAGC

AGTAAGTCAACTACTCCAGCGACATGTATTTCGGTACAGAGGGAGTAATATATATAGCTCTGTGC

TTGCCTGCTTAATCACACTCTGTTCCATGTGCCTATGACACGTTTTGTCATCTATCTACACATCAT

-continued

CATCGCTATCGTCTTATTCTTGAGTATAATCAAACACTGGACTATTTCCTTTTTGTAGAGAAGGAT

GGAACAATCAGAAAGCGGCATTTTTTCGTATAACCTGAGGTTGTATCCCGGTAGATATGAGGTAA

TGGCGTGCTATTCTGCTTTCATTGTCACTGCTTTCTCGTCATCTGATAGTGGGTGTTGGTTTGTG

CTTCAGATTAAATTTATTGTTGATGGTGTTTGGAAGAACGACCCGCTGCGCCCTAGCGTGAACAA

CCATGGGAACGAAAACAACCTTATGATTGTCACTTGACCTGCATCCTTGTAGCAACTGTGTAGAT

TATAGATTGTCATCAACAATGATTGGTGCCAACTGATTAGATCTCTTCTTTCTTCCGTGTAGCTTA

TCAGTTTTTCCTGCCTGTCGTTTCTTCATTATTTCTTAGAGAGCCACGCACAACTTCAGGGTGTTG

TCTTCGCCCCGCTGAGATGGGAGAAGAATGTAGCTGTTGGTGTGTGTGTTCTTTCCTTCCCCCT

CTTTCATCTCCCTGGAGAAGCATAGTGGGGCACTCGAACGCCCCGGTGGCGGTTGGGGGTAGT

TCGCCGTCGGTGTCTCAGGTGTGTGTAACAATGTACATATCCCGTGATAGCAAAGTTGTCCATG

GTTAGTTTGTCAAGGTGGTGGCGTGCCTGTCAGTGTGCACGCACTGGTTCTTACTATAAGATCC

AGGCCGGGAACTCATCCGATAGAACAGAGCATGTCATCGTTGTGATATGCATTGGTTGGGATAG

CTATAGCTCGGCAGAAGGTTAGCAGCTCGGGCACAAATACAGAACACAGTGGAAATGTGAGTCT

CCATTGGGTCATGACGGTACAGTTGAACCAACCACAAGTACAGTGAAATCGTTCATC

J TaFlo6 4B

MPPPRQPYRRPAPAPAPAPRPSNAPAPAPPQRGPRDQEELEAAIYDFMRRSDKP

GAFPTRAELLAAGRADLAAAVESSGGWLSLGWSWSSDDDARRPAASTAGPGVHP

DYPPEAGASGRAPNATADSVREQQEPTPSGRQPETEETQEAGSGAGLEGMLTRL

RRERERARPPPRSKNRAGGQGQNGALMNHNGAPSRSPTDGMYTRRIPVNGNIH

RSHSQNGIPEDNKSSSSANDAWRTWSLDKSRFSDFEAAEIHPLSRKPPKRADLDT

VLIEDDVPGPSNGVVINDYPSDHVDSERDEIHARFQNLEFDLADSLKTLRSRFDGV

SSYMSNGEEADVVNGFSDDWEFEETKVMHAQEELRTIRAKIAVLEGKVALEIIDKN

KIIEEKQTRLDEVEKALSELRTVSVVWPNPASEVLLTGSFDGWTSQRRMEQSEGGI

FSYNLRLYPGRYEIKFIVDGVWKNDPLRPTVNNNGNENNLMIVT

K TaFlo6 4B

TCGATCAATCAAAAAGCAAAGCTTATTAAAGCCTGCCCTTCCGTGGCCCGGACGTCGATG

ATCTGTGGGCAGTGGAGCGCGGCGACGGCGGCCGGCGGCGGCGGCAGCGCATGATAGCGT

GGCAGTCAACTAGGCCGACATACCACACCCATACGCCGAGGCCAGGCACGGCAACGGGTC

ACGGGGAGCTCGCCGCGACAGGGACGTGACGTGTGTGGTGGTGGACGGCGCTCGCGTGGT

TTTTTTTTTTTCCCGTTTGCNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNGCCACCGCGTCTTC

GCCGCCACCGCCGACGGGCCGCAGCCCTGCCGCGGCCGCGTCTGCGTCTGCGCCGCCTAC

ATGCCCCCGCCGCGGCAGCCCTACCGCCGGCCCGCCCCCGCCCCGGCCCCGGCCCCGCGC

CCGTCCAATGCGCCCGCGCCCGCGCCGCCGCAGCGCGGCCCTCGGGACCAGGAGGAGCTC

GAGGCGGCGATCTACGACTTCATGCGCCGCTCCGACAAGCCCGGCGCGTTCCCCACCCGC

GCCGAGCTCCTCGCCGCGGGGCGCGCCGACCTCGCCGCCGCCGTCGAGTCCAGCGGAGGC

TGGCTCTCCCTCGGATGGTCCTGGTCCTCCGACGACGACGCGCGACGGCCGGCTGCGTCA

ACGGCCGGCCCCGGCGTGCACCCTGACTACCCGCCCGAGGCGGGTGCCTCTGGCCGAGCG

CCGAATGCGACGGCGGATTCCGTAAGGTGGGTAACCGAGCCGCTCTGTAATGTAATGCGC

-continued

CCCTCTGTTGATTGCTCTGCGACGACTTGCTGAATTCCGAGTGTTGCAGGGAGCAGCAGG

AACCCACGCCGTCTGGGAGGCAGCCAGAGACGGAGGAGACACAGTGGGTGCCTGCTAAAT

CTCTTTGGAGTTATTTTGATGATTGATATGTTGGTTCCTTATTGATTTTGCTTGTTGCTC

CTTAATCGATTGCAGGGAGGCAGGGTCTGGGGCAGGCCTGGAGGGGATGCTCACCAGGCT

GCGGAGAGAGAGGGAGCGTGCGCGGCCACCGCCACGCAGCAAGAATCGAGCGGGAGGGCA

AGGTCAAAATGGCGGTACGTGCATTTTCAACTCTCGGCGTTCTATCGAAACATATCTTCT

TTGCAAACAGTTATATGTTTGTTGATAAGGTTTGCAACCAATGAAACTTTGCATAGCAAA

GAGCTCATTGTTCCATATTGTTTAGTTACAGCCCGTGGAAGGCTTAAGACTCTGTTGGAT

AAAATTAATGCTAAGCTCATGCCGGGCAGGAAGGAAGTGCCGCCGCCGACAATAGTTCGT

GCAAAAGCTGTCTTTCTCACAGGCCGGACTTCCCTTTCCCCCGACATATATAACTTGCAG

TGCAGTAGTTTAGCGCTTTCCATTTAAGGTTGCAAAGGGGACAAACGTACCGTTTTTTGT

TCTATGTCGCTTTCTAAAAATAGAAGCGTGGCATTAGAACTTTATTTCTCATGATCCGAC

ATATTTTTTGTCGTCGTGCTACTGCTTAATGTAAAGTTGTTTGCACCTGGACAGCACTGC

AATTATTTGTGTAATTGTGAATCTACGTAAGACTACCACATTATTTTGTTTGTGCCTTTT

AATCATAGTGGTAATATGTTCTATTACATACAACTGGTTTAGCTTTGTTATTACTCTGCC

CATTTCAGCATTTGGTCCTTCCAAGCTAATGGCCTTTTTGTGTTAAATCTCTTACAATAC

ATGGAGGATAATTCATTTTCCATTTCAAATATGCTCTGTTAATAGTTGCCCCTGAATTGA

AGGGTCCATGCTCCCTAGATATACATGGTTGATTGAAGTTAGTAGACTGCGATTTGCAAA

TATATTTACTAATTAAGGACCGCTTTAAGATTGACCATGTGTTTAGGTATTTTACTGATT

TAGTGCACAGGGATCATTTTCTCGGTACTCTATTAGTATCAACAGTAAAAAGTACACATT

GTGAACTTTTGGCTGGAGACTCAGAGAGGAAAATTGAAAGAGTTCCACCTTATATAATAG

AAAATAGCATTGGTTTGTTATTGATGGAATGGATAATTTTTGTTAGAGAGCTTCTGGGTA

ATTATGTATGTGAACCTTTATTCTGATGTACCAAATACTTAATTTCTAGCTAGTGTTTCT

TCATTTGTATATTAATAATCATACTTCTGTGTTACATACATGCAGCTTTAATGAACCATA

ATGGAGCTCCTAGTCGAAGTCCAACTGATGGCATGTACACTCGAAGGATACCTGTGAATG

GAAATATACATCGCTCTCATTCTCAAAATGGAATACCAGAGGACAACAAATCAAGTAGTT

CAGCCAATGATGCATGGCGAACATGGTCTCTTGACAAGAGTCGGTTTTCTGATTTTGAAG

GTTATATGATAACTTAACTTTCTTTTGTTGCGCATCATATCTGTTATGATTATTTCATAA

CATGTTTAATATGCTGACAGCCGCTGAGATCCATCCTTTGAGCAGAAAACCACCAAAACG

TGCTGACCTGGACACTGTGTTGATAGAAGATGATGTTCCCGGACCATCTAATGGTGTGGT

TATAAATGATTATCCTAGTGATCATGTAGACTCTGAAAGAGATGAGATACATGCACGTTT

TCAAAATTTGGAATTCGATCTTGCAGATTCTCTTAAGACATTAAGATCAAGATTTGATGG

AGTTTCGTCATATATGGTGTGTCTCGTATCATCTTCTTTACTTATCTATCTTTTGTTGTG

AAATACTGGTGGGATACGTGATCTTGAGATTTTAGTGTGGTTTTGCATTCAGTTTTCTTC

ACTTATGCATTTGTAAAGTTGTTTATGCATTGTACTAGACATGGCTCTGCTGTTCCAAAC

AAAACACACCCGAAGATATGGTTCTGCTTGCTCTAATTTTCTCTTTATGCACTTAACACT

GCCTGCATCATACCCTCGCCCATCACTAGAAAAGTGCCATCTTGGGATGCATGCAGTCAA

ATTTTTTGATTTTGACTAACACTGTAACAGTATCCTCATCAATATGCAGTCTGACATGAA

AATTGTACGAGTTCATTTGCCAACGGAATAACTTCCATAAATTTTGATTTTATATCTGTA

GATATTCACTGTATATCCCCTATCTTTTCTTGCAATGTTGTGATTTCGCAAGGCAAACAA

-continued

ATGATTATAGCTAATAATATTCCCTTGCAGTGCTGATTGCTGAATGTAGTTGTGTTCTCT

ACGAGGAAGTAGTTGGCTAGTCGCAATCTAAAAAGCACAGATACGGAGACATGGACACGT

CGATACGCCTACGGGACACGGGATACGGCATTTTCCAAAAACAGCCATTCAGGGATACGG

CGAGTATATATGGAAAAAATTAAAACATGCCATGTAATATAGAGTTAAAAACAAAAAAAA

TGAAGAGAAACTGAGATAAGATCAGAATACTGCCCCATTTCCATTTGTTGTATTGTTTTT

CAAGTGCTTAATGATTGAATTAATTGATCCTCTAGACCCATGTCATTGCAACTTGCAAAA

TACATCAAATGCTAGTATTAGTCTGTTAGAGAGTAGAGACTGGAGAAGACATGCAACAAA

GGATGCAGGTGTAACTTTCACCCTCACCCACGGACGTTGGCCACCGGCGGTGGTGCTCCC

AGACACCATGCTCCCTAACGTCAAGCAACAATCAAAACAGCAGCACCAGGCACCAGCATG

CAAGTGAGCAGCAGCTCAAGAGCAAGCAGCAACGGCATGGACGCATGGGGAAGCAAGCAG

CAGACTCAACAGCAAGAAATCGAGCAAAGATATGAAGAGGTTGAGGCTGCTGGGGTTATC

TGCTCGAGCGTGGTTGCCATCGAGTGGTTGNNNNNNNNNNNNNNNNNNNNNNNNNNNNNN

NNNNNNNNNNNNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNNNNNNNNNNNN

NNNNNNNNNNNNNNNNNNNNTGGAGCAGCGTTCCTTTAGTGGCGACCGTGTGTGCGACCT

TGCAAAATAGGGTTTGTATCGGGCCGAGGCTGTTATTGAGCTTCCTGTGTCCCCAACGTA

TTCCATACGCATCCCAGCTGTGTCTTTGTTTTTTTTTCCTTTTTTTTAATTAGGAAATCA

GGGGATACTGGGGGACACGCGTATCCCAGCATGTCCGGCCGCTTCGCCGTGTCCCACCGA

ATTAGGATGGCAATTCGGCAGTTTTGGCCATTTCCATGCTTTGTAGGTCGCAATGATTTA

GTTTGCAAATTATTACACACTCTTGTTATTTAGAACCATCGTATTACTGGTAGGAAGTTT

CTGATCTTCGAGATTCAGCCGACGCTGATATGAAACTAAAATGATAATGGAAGATCTTGA

TGCATCTCATTTTGATTTTTCTAGAGGTAATATACTTGTTCTGAGCATCCATCTTTGCCC

TTCCATTTTCCAGTCAAATGGCGAAGAAGCAGATGTGGTAAATGGGTTCTCTGATGATTG

GGAATTTGAAGAGACAAAAGTAATGCATGCCCAGGAAGAATTACGGACAATCCGTGCTAA

AATAGCAGTATTAGAAGGCAAGGTGGCGCTCGAAATAATGTATGGTCACTCACAATTGAA

TGTTGATCATCTACGCTTTTTATTTTGTATCAATCTCTTTTATGACTTATTCTGTTGATA

TCAGTGACAAGAACAAAATAATTGAAGAAAAGCAAACGAGGCTTGATGAAGTTGAGAAGG

CTTTGAGTGAGCTCCGCACAGTATCTGTTGTATGGCCCAATCCTGCTTCAGAAGTTCTAT

TGACCGGTTCTTTTGATGGGTGGACAAGCCAAGTAAGTGCATGTTCCGATTGTCTGCTTA

ATTAATAAATATATAAACTTCACTAACTAACTACAAAATGGGTGGCAGTTCATGATTTCA

ATTTCTATCACCCTTTGGTGTTAGTTGTCAGGTGAATTCCATTGATTTATGTATTAAGTT

GAATACTATTGAAGAGAGAAGCCGGTTCTATTGCTGCTCTCCTAAGTTGTGTAAATGCAA

TTTACTGCCAACATCTTCTCATGTGCACAGTTAATTCATTTATTAATGAGTGCAAAACAA

GCACATATAAATTAGATGCAGCAAGTTACATGGAAACCTCATCTTAGGGAACATACTCCC

-continued

TCCGATCCATATTACAGAGGGAGTACTTAGTTTGATGTGGTTCACACACAAGTAAAGTAA

CTTCAGGAACTAGCAACATGGTAGTTACGAGAATGGTAGGGATCAAGGCACCAAGTGCTT

TGAAAGATGTTTATTACGTATATGTTTCTAGGAGTAAAGCAAGTTTTTAATCTGATTTTG

GTTGTTGGTGCTGTTTTTGGCATAGGCACAATTGTGATGACACGTGTCCATAACTTTTGT

GTTAGAAATACTACGTGCTATTTGGATTTGAAAGGTTAGAAACATTGTTTTATATGCCAA

AAGAAAAAAGGAAAAGCACATGGAATCTTCATAAATTTGTTAATACTCCTTCCGTTCCTT

TTTATGACTTGTATTGGTTTGTTGGAAAGTCAAACTTTTTTACCTTTGACCAAGTTTATA

AAAAGTCAATGTATGCAATACTAAATACATAAAATATGGAAATATTTTTCATGAAGGGTC

TGATGATACTCATTTGGCATTGTAGATGTTGATAATTTTTTCTATATAAACTTCGTCAAA

GATAGAAAAGGTGGACTTAAAAAAACATCTTATAAAAAGGGACGGAGGGAGCATGTATTT

ATCATTCTATATTAAGTGGAAACTGAAGCAGCACAATTTTACAAGAGCTCACTAGGCAAG

ACCTATCAACAAATATACTACCTCTGCAACTTTTTATAAGACATTTTTAGAGTCTATGAC

AATGTGAAAAACGTGTTATATTAAGTTACGGAGGGAGTATGTCTTTATCTGGTACCTTTA

GCTGAGATTTAGTCAGTTCCTAGGAGGATACTGGTCACATGACTGACATATCCAAAAAGA

TGTTCTTCAGTTCGAGCACATATAGGATAGGTACTAGATGTAGAAGCCTGAAGGACAACA

TTCTGCCATTATAGATCTTAGTTTCACTTCCATATGTATGGGGGTGCTGTTTAGTTTTGT

CATCTATCTATATATCGTTGTCGCTATCGTCTTATTCTTGAGTATAATCAAACACTGGAC

TTTTTCCTTTTTTGTAGAGAAGGATGGAACAATCAGAAGGAGGCATTTTTTCGTATAACC

TGAGGTTGTATCCTGGTAGATATGAGGTAATGGCGCGCTATTCTTACTTCACTGTCACTT

CTTTCACTTCATCTGATAGTGGGTGTTGGTTTGTGCTTCAGATTAAATTTATTGTTGATG

GTGTTTGGAAGAACGACCCGCTGCGCCCTACTGTGAACAACAATGGGAACGAAAACAACC

TTATGATTGTCACTTGACCTGCATCCTTGTAGCAACTGTGTAGATTATAGATTGTCATCA

ACAATGATTGGTGCCAACTGATTAGATATGTTCTTTCTTCCTTGTAGCTTATCAGTTTTT

GCCGCCTGTCATCTCTTGATTTTCTTTTAGAGAGCCACGCGCGACTTTGAACAGTGTAGG

GTCAGGGTGTTGTCTTCACCCCCGCTGAGATGGGAGAAGAATATAGCTCAATGTTTGTGC

GTTCTTTCCTTTCCTCTCTTTCTTCTCCCTGGAGAAGCATAGTGGGGCACTCAAATGCCC

CGGTGGCGGTTGGGGGCAGTTCGCCGTCGGTGTCGGTGTGGGTAACAATGTACATATCTC

GTGATAGGAAAGTTGTCCATGGTTAGTTTGTCAAGGTGGCGGCGTGCCTGTCAGTATGCG

CGCACTGGTTCTTACTAAGATCCAGGCCGGGAACTCATCTGATAGAACTCACTCGGCAGA

AGGTTAGCAGCTCATGCACAGATACAAAACACAGTGGAAATGTGAGCCTCCATTGGGTCA

TCACAGTACAGTTGAAGGCACATTATGCCTGAAACCAACCACAAGTACAGTGAAATAGTT

TATCTTCCATTTTAACAACTTACAAGAAAGAAATTAACCACCCCATTGTTGTTTCTTTCA

TTTTCAACAACTTACAAGAAATTAACCACCCCATTGTTGTCTACAGTACATTTCTTCCTC

TCTTTCCCCGCCCACTTCATCTATAGATTGATTGATTTCATAACAGCAGAACCAAAAAAT

TATAAGAACACAGAAGGGAAATAGCTACTGTGGTATGTATAAGACACGTGAATTAATCAC

CTGACCTTATTCTACCCCCTTCTTCCCCATTGCATCAAGCATCTCTGGTCCCCTTGAACC

TGTACCACCTGGCGCAGATCATGAAGTAGACAAAGTTGAAGACGCCAATGCCGGCGATCA

TCCAGTAGAAGAGGTCGAGCCTGCCCTTGTTGAGGTCCTGCGCCAGCCAGTTCTGGCCGG

CCCCCGTGGTCCGGTGCACGATCGTCGTCAGGAAGCCGCTGAGGTAGTTCCCCAGGGCGA

GGTTGCAGAAGGCGAGCGCGCCGGCGACGCTCCTCATGTGCTCCGGGATCTCCTTGTAGT

-continued

AGAACTCGATCTGGCTGATGAGGTTGAATGCCTCGGAGAGGCCGAGGATCATGAGCTGCG

GCACCATCCAGAAGCTGGACATGGCGGAGATGCCGCCCCCCGTCTGCGTCGTGCCGATGT

TGGGCTGGTTGAGCGCGATGTCCCTGCGCCGGTCCTCGACGACGGCGGAGATGATCATGG

CGACGGTGGAGAGCGCGATCCCGATGCCCTGGCGCTGGAGCAGCGTGAAGCCCTCGTCCT

TGCCGGTGACCTTGCGGAGGCGCGGCACGAGGAGCCGGTCGTAGATGGGGATCCAGAGCG

TCTGCGCGAGCATGGCGAAGACGGTGAATGACGCGGCGGGGACGTGGAAGCTGCTGCCGA

GGCGGCGGTCGGACTGCAGCGCGGAGAAGACGACGTAGGTGGACTGCTGCACCACGGCCA

CGTAGTAGATGATCCCGGTGGACCAGACGGGCACGATGCGGATGAGGCATTTCACCTCCT

CCACCTGCTGCACGGTGCAGAGCCGCCAGGGGTCGGCCGCGGTGGCGCCGCCGGGGCGCA

CCTCGTCCTGGGACGCCACCATGGCCGCCTTGTCGAGGCACCGGAACTGGTCCGTGTGCG

CAAGCTTGGTGACGATGGCCGAGGTGTGCGGCGGGTCGAACAGGTCCTGCTTGGGGTCCT

TGGCCTGCTTGAGCGAGCGCTTGGCGAAGGCGGCGGCGAAGACCTGCACGATGGTGGTGA

AGGGGGAGCCCTCGGGGATGACGCGCACGTAGAGGCGCGTGCCCATGAAGAAGAGCACGC

AGGCGAGGAACATGAGCGCGGTGGGGATGCCGAGGCCGATGGCCCAGTTGACGTTGCTCT

GCACGTAGATGATGACGGTGGCGGAGACGAGCATGGCGGAGGTGAAGGTGAAGTAGTACC

AGTTGAAGAAGCTGTTGATCCCGCGCTTGCCCGACTCGGTGTGCGGGTCGAACTGGTCGG

CGCCGAACGGCATGCTGCAGGGCCGGATCCCCGCGGAGCCGATCACCAGGAAGGCGAAGG

CGATGAAGAGGACGGCGAGCTGGTAGGAGGTGGCCTTCTCGCAGACCTCCCCCACGCCGC

AGTCCGCCGGGTGCAGGCTGTCCGCGCCCGCCGTCAGCGTCAGGAAGAACATGCCCTGGG

ATGAACAGGCAAGCGTTAGTCAGTGCTGGAGAGAAACGAACACAGGCTTTGTCAAGAAGA

TCTTGTTAGTTGCTACTCCCTCCGTTCCGAAATATAAGTCGTTGAACTGGTAATAGTTCG

AAGCTGCGCAACGTTCAGAATTCACACGGCCGTGTGCATCGATTGATGCAGAGGCAGGTG

GTTTTTACCTCCTTTTCGAAGAAGAAAAAATGATTCAATCAAGTTATTCCCAGTTTACTG

CACTGCCCCAACACTCCCTGCTTCCTCGCCTCGCCTCGCCGTGCACACGCGGCCGCCCCA

CCCCACCCACCTCGCCGCGCGCGCGCGGGTCCGGCCGGCAGCATCCTGTGCGCGTGGTCA

CCACCAAATCCCCGCTCCGGTCCACGGATCCAGCGGCCACGCGCACCGCCGGGGGAACAC

GACACAGCGCGCGCGCTGGCTGCACCCCACTCCCCCCGCCCGAACTCGATCCCCATCCCC

CGAGTGGCTGTCGTTGTCAGTCAGGCAGGCGGAGAAGCTTCCGCTTCCAGCACAGCAGCT

CGGCGGAGCCAGCCCAATGGCGATACTATTCTCATGATCGAGACAGGGGTGGGTGGCCAC

TGGCCAGCGATCGCGGCGACTGACATTGACGCGGCAACGTGGGGTGCTTCCGGTTGGGTG

CTCCTGGACAAGGCACGGATCGCTCTCGTGGCAAGAGAGATGCGCGTGTCCTGGAGCGTG

CGGTGCGCGCCATTTTCCCACGGAACCGGACGGACGGCCGGTGGCCGCCGCGTTGAGGCG

GTCAATGTTGACATGCCACTCCGGCTGGCCCGCAGCGAAGACCGCTCGTGGCTGGGTCGC

GCAACTAGTTGGCAGACAAACGCATAGTACACGTCCTCTGCCAAACAAAAC

L TaFlo6 4D

MPPFLLSLSLPALTLPLPPAPAPAPRRHRVFAAPAYGPQPCRGRVCVCAAYRPPP

RQPYRRQPAPAPAPDPRPRPSNAPAPPQRDPRGQEEVEEAIYDFMRRSDKPGAF

PTRAELLAAGRADLAAAVESSGGWLSLGWSWSSDDDARRPAASSAGPGVHPDY

PPEAGPSGRPPNSAADSVREQQEPTRSGRQPETEETEEAGSGAGLEGMLARLRR

ERERARPPPRSKNQAGGQGQNGALMNHNGAPSRSPTDGMYTRRIPVNGNIHRS

HSQNGIPEANKSSSSANDAWRTWSLDKSRFSDFEAAEIHPLSRKPPKRADLDTVLI

-continued

EDDVPGPSNGVVINDYPSDHVDSERDEIHARFQNLEFDLADSLKTLRSRFDGVSSY

MSNGEEADVVNGFSDDWEFEETKVMHAQEELRTIRAKIAVLEGKVALEIIEKNKIIEE

KQTRLDEVEKALSELRTVSVVWPNPASEVLLTGSFDGWTSQRRMEQSESGIFSYN

LRLYPGRYEVMACYSASIVTTFTSSDSGCSFVLQIKFIVDGVWKNDPLRPTVNNHG

NENNLMIVT

M TaFlo6 4D
ATCCAACGGTTCTAACGTAGTTCGCTGGGAAAACGTCCCCGGCTGCCGTCGGCCAGTTAA

GATTTCCCTTCTTTTAGCTCTGCGTTTAGCAAATACTCCGTACTAGACAAAAAGGTAGAG

GGAAGTTCACAAGCAGAGCCGTCGGCCAGAAAAGCGCAAAACGCACCAGGGTTCTCACAC

GACACGCCTCGACGTTTCCATCTTTCGTCACGCCGTGCTTCCATCCATCCATCCGTCGAT

CAATCAAAAAGCAAAGCTTATTAAAGTCCGCCCTTCCGTGGCCCGGACGTCGATGATCTG

TGGGCAGCGGAGCGCGGCGACGGCGACCGGCGGCGGCAGCGGCAGCGCAGGGTAAGCGTG

GCAGTCGACCAGGCCGACATACTACACCCATACGCCGAGGGCCAGGCGCAGGCACGGCAA

CGGGTCACGGAGAGCTCGCCGCGACAGGGACGTGACGAGCTGGCTCTACTCTACTAGTGG

TGGTGGACGGCGCTGGCGTCGCTCTATTTTTTTTCGTTTTCCCCCTCCCTCCTCCGCTCT

CCGGTTCCGGGAAAGCTCCCGCCCTCGCCGCTCGGGGAGCGGCAGAGAAATGCGACGGCG

ATGCCCCCCTTCCTCCTCTCGCTGTCCCTCCCAGCCCTAACCCTACCCCTGCCTCCCGCC

CCCGCCCCCGCCCCTCGCCGCCACCGCGTCTTCGCGGCGCCCGCCTACGGGCCGCAGCCC

TGCCGCGGCCGCGTCTGCGTCTGCGCCGCCTACAGGCCCCCGCCGCGGCAGCCCTACCGC

CGCCAGCCCGCCCCGGCCCCGGCCCCGGACCCGCGCCCGCGCCCGTCCAATGCGCCCGCG

CCGCCGCAGCGCGACCCTCGGGGCCAGGAGGAGGTCGAGGAAGCGATCTACGACTTCATG

CGCCGCTCCGACAAGCCCGGCGCGTTCCCCACCCGCGCCGAGCTCCTCGCCGCGGGGCGC

GCCGACCTCGCCGCCGCCGTCGAGTCCAGCGGAGGCTGGCTCTCCCTCGGATGGTCCTGG

TCCTCCGACGACGACGCGCGGCGGCCGGCCGCGTCGTCGGCCGGCCCCGGCGTGCACCCT

GACTACCCGCCCGAGGCGGGTCCTTCTGGCCGACCGCCAAACTCGGCGGCGGATTCCGTA

AGGTGGGTAACCGAGCCGCTCTGTGATGTGTAATGTACCCCTCTGTTGATTGCTCTGCGA

CGACTTGCTGAATTCCGAGTGTTGCAGGGAGCAGCAGGAACCGACGCGGTCTGGGAGGCA

GCCGGAGACGGAGGAGACAGAGTGGGTGCCTGCTAAATCTCTTTTGAGTTATTTTGATTG

ATATGTTGGTTCCTTATTGATTTTGCTTCTTGCTCCGTAATCGATTGCAGGGAGGCAGGG

TCTGGAGCAGGCCTGGAGGGAATGCTCGCCAGGCTGCGGAGAGAGAGGGAGCGTGCGCGG

CCACCGCCACGCAGCAAGAATCAAGCGGGAGGGCAAGGTCAAAATGGCGGTACGCGCATT

TTCGATTCTCCGCGTTCTATCGAAACATGTGTTGTTTTCAGTTGTGCAGCATGAGCATCT

TCTTTGCAAACAGTTATATGTTTGTTGATAAGGTAACACCAACTTTTGCAACCAATGGAA

CTTTGCATAGCATAGAGCTCATTGTGCCATAATGTTTAGTTACAGCCCGTGGAAGGTGGC

TTAACGCTCTGCTGGATAAAATTAATGCTAAGCTCATGCCGGGCAGGAAGGAAGTGCCGT

TGACAATAGTTCATGCAAAAGCTGTCTGTTCTCACGGACCGGACTTCCCTTTCCCCTGAC

ATATATAACTAGCAGTTCAGTAGTTTAGCGCTTTCCATTTAAGGTTGCAAAGGGGACAAA

CGTACCGTTTTTTGTTCTATGTCGCATTCTAAAAATAGAAGTTTGGCATTAGAACTTTAT

TTCTCATGATCCGACATATTTTTTGTCGTCGTGCTACTGCTTGATGTAAAGTTGTTTGCA

CCTTGACAGCACTGCAATTATTTGAGTAATCGTGAATCTACGGAAGACTACCACATTATT

TTGTTTGTGCCTTTTAATCATAGTAGTAATATGTTCTGTTACATACAACTGGTTTAGCTT

-continued

TGTTATTACTCTGCCCATTTCAGCATTTGGTCCTTCCAAGCTAATGGCCCTTTTGTGTTA

AATCTCTTACAATACATGGAGCATAATTCATTTTCCATTTCAAATTGCCTCTGTTAATAG

TTGCCCCCTAACACCTAAATGAATTGAAGGGTCCATGCTCCCTAGATATACATGGTTGAT

TGAAGTTAGTAGACTCTGCGATTTGCAAATATATTTACTAATTAAGGACCGCTTTAAGAT

TGACCATGTGTTTAGGTATTTTACTGATTTAGTGCACACGGATCATTTTCTCGGTACTCT

ATTAGTATCAACAGTAAAAAGTACACATTGTAAACTTTTGGCTGGAGACTCAGAGAGGAA

AATTGAAAGAGTTCCACCTTATATAATTGAAAGAGTAGAAAATAGTGTTGGTTTGTTATT

GATGGACAACTAATGGATAATTTTTGTTAGAGAGCTTCTGGATAATTATGTATGTGAACC

TTTATTCTGATGTACCATATACTTAATTTCTAGCTGGTGTTTCTTCATTTGTATATTAAT

GATCATACTTCTGTGTTACATACATGCAGCTTTAATGAACCATAATGGAGCTCCTAGTCG

AAGTCCAACTGATGGCATGTACACTCGAAGGATACCTGTGAATGGAAATATACATCGCTC

TCATTCTCAAAATGGAATACCAGAGGCCAACAAATCAAGTAGTTCGGCCAATGATGCATG

GCGAACATGGTCTCTTGACAAGAGTCGGTTTTCTGATTTTGAAGGTTATATGATAACTTA

ACTTTCTTTTGTTGCACATCATATCTTATGATTATTTCATAACATGTTTAATATGCTGAC

AGCCGCTGAGATCCATCCTTTGAGCAGAAAACCACCGAAACGTGCTGACCTGGACACTGT

GTTGATAGAAGATGATGTTCCCGGACCATCTAATGGTGTGGTTATAAATGATTATCCTAG

TGATCATGTAGACTCTGAAAGAGATGAGATACATGCACGTTTTCAAAATTTGGAATTCGA

TCTTGCAGATTCTCTTAAGACATTAAGATCAAGATTTGATGGAGTTTCGTCATATATGGT

GTGTCTCGTATCATCTTCTTTACTTATCTATCTTTTGTTGTGAAATACTGATGGGATACG

TGATCTTGAGATTTTAGTGTGGTTTTGCATTCAGTTTTCTTCACTTGTGCATTTGTAAAG

TTGTTTATGCATTGTACTAGACATGGCTCTGCTGTTCCTAACAAAACACACCCGAAGATA

TGGTTCTGCTTGCTCTAATTTTCTCTTTATGCACTTAACACTGCCTGCATCATACCCTCG

CACATCACTAGAAAAGTGCCATCTTGGGATGCATGCAGTCAAATTTTTTGATTTTGACTA

ACACTGTAACAGTATCCTCATCAATATGCAGTCTGACAACATGAAAACGGTACAAGTTCA

TTTGCCAACGGAACAACTTCCATAAATTTTGATTTTATATCTGTAGATATTCACTGTATA

TCCCCTATCTTGTCTTGCAATGTTGTGATTTCGCAACGCAAACAAATGATTATCGCTAAT

AATATTCCCTTGCAGTGCTGATTGCTGAATGTAGTTGTGTTCTCTACGAGGAAGTAGTTA

GCTAGTCGCGATATAAAAAGCACAGATACGGAGACATGGACACGGCGATACGCCTAGGGG

ACACGGGATACGGCATTAAACAGCCATTCAGGGATACGGCGAGTATATATGAAAAAAATT

AAAACATGCCATGTAATATAGAGTTAAAAAAATGAAGAGAAACTGAGATAAGATCAGAAT

ACTGCCCCATTTCCATTTGTTGTATTGTTTTTCAAGTGTTCAATGACTGAATTAATTGAT

CCTCTAGACCCATGTCATTGCAACTTGCAAAATACATCAAATGCTAGTATTAGTCTATTA

GAGAGTAGAGACTGGAGAAGACATGCAACAAAGGATGCAGGTGTAACTTTCACCCTCACC

CACGGACGATTAGCCACCGGCAGTGGCGCTCCCAAACGCCATGCTCCCTAACATCAAGCA

ACAATCAAAACAGCAGAACCAGGCACCAGCATGCAAGTGAGCAGCAGCTCAAGAGCAAGC

AGCAACGGCATGGACGCATGGGGAAGCAAGCAGCAGACTCAACAGCAAGAAATCGAGCAA

AGATATGAAGAGGTTGAGAAGAGGCTGCTGGGGTTATCTGCTCGAGCGTGGTTGTCATCG

GGCGGTTGAGTCCAGGGGGCGGTGGCGATAGCGCGTTCGACTTGGAGCAGCGTTCCTTTA

GTGGCAAGCGTGTGTGCGACCTTGCAAAATAGGGTTTGTATCGGGCCGAGGCTGTTATTG

AGCTTCCTGTGTCCCCAACGTATTCCATACGTATCCCAGCTGTGTCTTTGTTTTTCTCCT

TTCTTTAATTAGGAAATCAGGGGATACTGGGGGACACGCGTATCCCGGCATGTCCGGCCA

-continued

TATCGCCGTGTCGCACCGAATTAGGACGGCAATTCGGCAGTTTCGGCCGTTTCCATGCTT

TGTTGGTCGCAATGATTTAGTTTGCAAATTATTACACATTCTTGTTTTTTAGAACCATTG

TATTACTGGTAGGAAGTTTCTGATTTTCGAGACTCGGCCGACGCTGATATGAAACTAAAA

CGATAATGGAAGATCTTGATGCATCTCATCTTGACTTTTCTAGAGGCAATATACTTGTTC

TGAGCATCCATCTTTGCCCTTCCATTTTCCAGTCAAATGGCGAAGAAGCAGATGTGGTAA

ACGGGTTCTCTGATGATTGGGAATTTGAAGAGACAAAAGTAATGCATGCCCAGGAAGAAT

TACGGACAATCCGTGCTAAAATAGCAGTATTAGAAGGCAAGGTGGCGCTTGAAATAATGT

ATGGTCACTCACAATTGAATGTTGATCATCTACGCTTTTTATTTTGTATCAATCTCTTTT

ATGACTTATTCTGTTGATATCAGTGAGAAGAACAAAATAATTGAAGAAAAGCAAACGAGG

CTTGATGAAGTTGAGAAGGCTTTGAGTGAGCTCCGCACAGTATCTGTTGTATGGCCCAAT

CCTGCTTCAGAAGTTCTATTGACCGGTTCTTTTGATGGGTGGACAAGCCAAGTAAGTCCA

TGTCCCAATTCTCTGCTTAATTAATAAATATATAAACTTCACCAAGTAACTACAAAATGG

GTGGCAGTTCATGATTTCAATTTCTATCACTCTTTGGTGTTAGTTGTCAGGTGAATTCCA

TTGATTTATGTATTAAGTTGAATATTAATGAAGAGAGAAGCTGGTTCTATTGCTGCTCTC

CTAAGTTGTGTAAATGCAATTTACTGCCAACACCTTATCATGTGCACAGTTAATTCATTT

CTTAATGAGTGCAAAACAAACACATACAGCAAGTTATATGGAAACCTGCATCTTAGGGAA

CATACTCCCTCCAGTCCATATTACAGAGGGGGTACTTAATTTGATGTGGTTCACACACAA

GTAAAGTAACTTCAGGAACTAGCAACATGGTAGTTACGAGAATGGTAGGGATCGAAGGCG

CCAAGTGCTTTGAAAGATGTTTATTACGTATATGTTTCTAGGAGTAAAGCAAGTTTGTAA

TCTGATTTTGGTTGTTGGTGCTGTTTTTGGCATAGGCACAATTGTGATGACACGTGTCCA

TAACCTTTGTGTTAGAAATACTACGTGTTATTTGGATTTGAAAGGTTAGAAACATTGTTT

TATATGCCAAAAGAAAAAGGAAAAGCACATGGAATCTTCATATATTTGTTAATACTCCTT

CCATTCCTTTTTATGACTTGTATTGGTTTGTTGGAAAGTCAAGCTTTTCTACCTTTGACC

AAGTTTATAAAAAAAAATCAATGTATGAATACTAAATACATACAATATGGAAATATTTTT

CATGAAGGGTCTGATGATACTGATTTGGTATTGTAGATATTGATACTTTTTTCTATATAA

ACTTGGTCAAAGATGGAAAAGGTGGACTTTAAAAAAACATCTTATAAAAAGGAACGGAGG

GAGTATGTATTTATCATTTTATATTAAGTGGAAACTGAAGCAGCACAATTTTACAAGAGC

TTCACTAGGCAAGACCTAGCAACAAATATACTACCTCTGCAACTTTTTATAAGACATTTT

TAGAGTCTATGACAATGTGAAAAACGTTTCATATTAAGTTAGGGAGGGAGCATATCTTTA

TCTGGTACCTTTAGCTGAGATTTAGTCAGTTCCTAGGAGGATACTGGTCACATGACTGAC

ATATCCAAAAAGATGTTCTTCAGTTCGAGCACATATAGGATAGGTACTAGATGTAGAAGC

CTGAAGGACAACATTCTGCCATTATAGATCTTAGTTTCACTTCCATATGTATGGGGGTGC

TGTTTAGTTTTATTTTGTATACATGATATTTGCATTTCCATGGAGCACACAGCACAATTC

AGATCAGCCAGCAGAAGAATGTTAGTAATACAAATCAAATTTGGTTCTAGAGTAAGAAAT

ATTACCTGCGTCCCAAATTACTTGATCTAAGACAAGTAATTCGGGACGGATGGAGTATGA

ATTTGTTATGCCATTTCACCTCTCTTGTCGCTCCTTTGATATAACTTTCAAGATATTGAA

TAATTAAACATCTAATTGTATGAATGTCCATGGAATGTTGTCTGCTTTGGGCTGTGTACT

GCAGGAAGTCTCTCTGTTAATATATATAGCTCTGTGTTTGCCTGCTTAATCACATTCTGT

TCCATGTCATGCCTATGACACGTTTTGTCATCTATACATCGTCATCGCTATCGCCTTATT

CTTGAGTATAATCAAACACTGGACTATTTTCCTTTTTGTAGAGAAGGATGGAACAATCAG

-continued

AAAGCGGCATTTTTTCGTATAACCTGAGGTTGTATCCCGGTAGATATGAGGTAATGGCGT

GCTACTCTGCTTCCATTGTCACTACTTTCACATCATCTGATAGTGGGTGTTCGTTTGTGC

TTCAGATTAAATTTATTGTTGATGGTGTTTGGAAGAACGACCCGCTGCGCCCTACCGTGA

ACAACCATGGGAACGAAAACAACCTTATGATTGTCACTTGACCTGCCTGCATCCTTGTAG

TAACTGTGTAGATTATAGATTGTCATCAACAATGATTGGTGCCAACTGATTAGATCGCTT

CTTTCTTCCTTGTAGCCTGTCAGTTTTTGCCGCCTGTCGTTTCTTGATTGTTTTCTAGAG

CCACGCATGACTTGGACAGTGTAGGGTCAGGGTGTTGTCTTTCACCCCGCTGAGATGGGA

GAAGAATATAGCTGTTGGTGTGTGTGTTCTTTCCTTCCCCCTCTTTCTTCTCCCTGGAGA

AGCATAGCGGGGCACTCGAATGCCCCGGTGGCGGTTGGGGGTAGTTCGCCATCGGTGTCT

CGGGTGTGTGTAACAATGTACATATCTGGTGATAGCAAAGTTGTCCGTGGTTAGTTTGTC

AAGGTGGTGGCGTGCCTGTCAGTATGCACGCACTGGTTCTTACTAAGATCCAGCCCGGGA

ACTCATCTGATAGAACAGAGCATGTCAAATGCATTGGTTGGGATTGGTTGGGATAGCTAT

CGGTCGGCAGAAGGTCAGCAGCTCAGGCACAAATACAAAACGCAGTGGAGATGTGAGCCT

CCATTGGGTCGTCACAGTACAGTTTGAAGGCATGCATGCCT

The invention claimed is:

1. A tetraploid or hexaploid wheat plant having at least one non-functional Flo6 gene in an A or B sub-genome of tetraploid wheat or an A, B, or D sub-genome of hexaploid wheat, wherein SEQ ID No. 53, SEQ ID No. 55, and SEQ ID No. 57 each set out the sequence of a functional A, B, or D sub-genome Flo6 gene in wheat, respectively, and wherein the number, weight, or volume of B-type granules in endosperm in grain of the tetraploid or hexaploid wheat plant is reduced compared to endosperm in grain of a wild type tetraploid or hexaploid wheat plant.

2. The plant as claimed in claim 1 which is *Triticum aestivum.*

3. Grain produced from the wheat plant as claimed in claim 1.

4. The grain as claimed in claim 3 which is *Triticum aestivum.*

5. Grain harvested from the wheat plant as claimed in claim 1.

6. A genetically modified Flo6 wheat gene of SEQ ID Nos. 53, 55, or 57, wherein the Flo6 wheat gene is genetically modified to express a non-functional protein in one or more of the A, B, or D sub-genomes of a hexaploid wheat plant or the A or B sub-genomes of a tetraploid wheat plant, such that the number, weight, or volume of B-type granules in endosperm in grain from the hexaploid or tetraploid wheat plant is reduced compared to endosperm in grain of a wild type wheat plant.

7. The genetically modified Flo6 wheat gene as claimed in claim 6, wherein said genetic modification of SEQ ID No. 53 comprises modification of the codons for Trp 291 and/or Trp 400 of SEQ ID No 54 to produce non-functional expression product.

8. The wheat plant as claimed in claim 1 which is a hexaploid wheat plant and has non-functional Flo6 genes in at least two sub-genomes.

9. The wheat plant as claimed in claim 8, wherein the non-functional Flo6 genes are in the A and D sub-genomes.

10. The wheat plant as claimed in claim 1, wherein a FLO6 expression product is reduced in the wheat plant such that the number, weight, or volume of B-type granules in endosperm in grain of the wheat plant is reduced compared to endosperm in grain of a wild type wheat plant.

11. The wheat plant as claimed in claim 1, which has a tetraploid genome and non-functional Flo6 gene in both the A and B sub-genomes.

12. The wheat plant as claimed in claim 1, which has a tetraploid genome and a non-functional Flo6 gene in either the A or B sub-genome, and wherein said FLO6 expression product is reduced such that the number, weight, or volume of B-type granules in endosperm of grain of the wheat plant is reduced compared to endosperm in grain of a wild type wheat plant.

* * * * *